US012128065B2

(12) United States Patent
Pittz

(10) Patent No.: US 12,128,065 B2
(45) Date of Patent: *Oct. 29, 2024

(54) COMPOSITION AND METHODS FOR GENERATING AND SUSTAINING MOLECULAR HYDROGEN ($H_2$) IN AQUEOUS SYSTEMS

(71) Applicant: Azulent, LLC, Greensboro, NC (US)

(72) Inventor: Eugene P. Pittz, Las Vegas, NV (US)

(73) Assignee: Azulent, LLC, Greensboro, NC (US)

( * ) Notice: Subject to any disclaimer, the term of this patent is extended or adjusted under 35 U.S.C. 154(b) by 25 days.

This patent is subject to a terminal disclaimer.

(21) Appl. No.: 17/685,644

(22) Filed: Mar. 3, 2022

(65) Prior Publication Data

US 2022/0323486 A1  Oct. 13, 2022

Related U.S. Application Data

(63) Continuation of application No. 16/736,749, filed on Jan. 7, 2020, now Pat. No. 11,318,160, which is a continuation of application No. PCT/US2019/042833, filed on Jul. 22, 2019.

(60) Provisional application No. 62/764,222, filed on Jul. 23, 2018.

(51) Int. Cl.
| | |
|---|---|
| *A61K 33/00* | (2006.01) |
| *A01K 61/13* | (2017.01) |
| *A01K 63/04* | (2006.01) |
| *A23G 1/42* | (2006.01) |
| *A23L 2/39* | (2006.01) |
| *A23L 19/00* | (2016.01) |
| *A23L 23/00* | (2016.01) |
| *A23L 33/10* | (2016.01) |
| *A61K 9/06* | (2006.01) |
| *A61K 47/02* | (2006.01) |
| *A61K 47/10* | (2017.01) |
| *A61K 47/12* | (2006.01) |
| *A61K 47/38* | (2006.01) |

(52) U.S. Cl.
CPC ............ *A61K 33/00* (2013.01); *A01K 61/13* (2017.01); *A01K 63/042* (2013.01); *A23G 1/426* (2013.01); *A23L 2/39* (2013.01); *A23L 19/09* (2016.08); *A23L 23/00* (2016.08); *A23L 33/10* (2016.08); *A61K 9/06* (2013.01); *A61K 47/02* (2013.01); *A61K 47/10* (2013.01); *A61K 47/12* (2013.01); *A61K 47/38* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,301,723 A * | 1/1967 | Chrisp | C08B 37/0087 |
| | | | 149/69 |
| 5,049,401 A | 9/1991 | Harada et al. | |
| 5,486,364 A | 1/1996 | King et al. | |
| 6,558,652 B2 | 5/2003 | Takata | |
| 6,733,769 B1 | 5/2004 | Ryan et al. | |
| 8,252,141 B2 | 8/2012 | Stigsson et al. | |
| 9,120,672 B2 | 9/2015 | Satoh et al. | |
| 11,318,160 B2 | 5/2022 | Pittz | |
| 2006/0127557 A1 | 6/2006 | Takata | |
| 2007/0172656 A1 | 7/2007 | Congdon | |
| 2008/0292541 A1 | 11/2008 | Kamada et al. | |
| 2010/0008849 A1 | 1/2010 | Martin | |
| 2011/0104048 A1 | 5/2011 | Maury | |
| 2011/0127167 A1 | 6/2011 | Misra et al. | |
| 2012/0263629 A1 | 10/2012 | Satoh et al. | |
| 2013/0011756 A1 | 1/2013 | Weaver et al. | |
| 2015/0258136 A1 | 9/2015 | Lucas | |
| 2016/0113865 A1 | 4/2016 | Kazakevitch et al. | |
| 2016/0296475 A1 * | 10/2016 | White | A61K 9/4808 |
| 2018/0034081 A1 | 2/2018 | Gomez | |
| 2018/0092816 A1 | 4/2018 | Perricone et al. | |

FOREIGN PATENT DOCUMENTS

| | | |
|---|---|---|
| AU | 2007250624 A1 | 11/2007 |
| CA | 2475658 C | 3/2013 |
| CN | 1228706 A | 9/1999 |
| CN | 101573300 A | 11/2009 |
| CN | 102408147 A | 4/2012 |
| CN | 102462694 A | 5/2012 |
| CN | 102892421 A | 1/2013 |
| CN | 107648257 A | 2/2018 |
| EP | 0122624 A2 | 10/1984 |
| EP | 0123235 A2 | 10/1984 |
| ES | 2210585 T3 | 7/2004 |

(Continued)

OTHER PUBLICATIONS

Aoe et al. Effects of Liquid Konjac on Parameters Related to Obesity in Diet-Induced Obese Mice. Bioscience. Biotechnology and Biochemistry 79(7):1141-1146 (2015).
Birketvedt et al. Experiences with Three Different Fiber Supplements in Weight Reduction. Med. Sci. Monitor 11:P15-P18 (2005).
Bu et al. Catalytic microwave pyrolysis of lignocellulosic biomass for fuels and chemicals. Advances in Bioenergy 1:69-123 (2016).
Chua et al. Traditional Uses and Potential Health Benefits of Amorphophallus Konjac. K.Koch ex N.E. Br. J Ethnopharmacol. 128(2):268-278 (2010).
EP Application No. 19841807.1 Extended European Search Report dated Mar. 25, 2022.

(Continued)

Primary Examiner — Patricia Duffy
Assistant Examiner — Garen Gotfredson
(74) Attorney, Agent, or Firm — Mintz Levin Cohn Ferris Glovsky and Popeo, P.C.

(57) ABSTRACT

Provided are compositions, methods, and solutions for generating aqueous glucomannan solutions with hydrogen compositions greater than 100 parts per billion. Said glucomannan solutions have application in nutritional, therapeutic, and energy fields.

18 Claims, 6 Drawing Sheets

(56) References Cited

FOREIGN PATENT DOCUMENTS

| GB | 2457464 A | 8/2009 |
|---|---|---|
| JP | 2004330028 A | 11/2004 |
| JP | 2007077035 A | 3/2007 |
| JP | 2012162429 A | 8/2012 |
| JP | 2013198475 A | 10/2013 |
| JP | 2016108291 A | 6/2016 |
| KR | 20160134609 A | 11/2016 |
| WO | WO-9808523 A1 | 3/1998 |
| WO | WO-0214213 A2 | 2/2002 |
| WO | WO-2008060293 A2 | 5/2008 |
| WO | WO-2009101444 A1 | 8/2009 |
| WO | WO-2013011756 A1 | 1/2013 |
| WO | WO-2015146460 A1 | 10/2015 |
| WO | WO-2015175547 A1 | 11/2015 |
| WO | WO-2018011634 A1 | 1/2018 |
| WO | WO-2018131505 A1 | 7/2018 |
| WO | WO-2020023396 A1 | 1/2020 |

OTHER PUBLICATIONS

Fukuda et al. Inhalation of Hydrogen Gas Suppresses Hepatic Injury Caused by Ischemia/Reperfusion Through Reducing Oxidative Stress. Biochemical and Biophysical Res. Commun. 361(3):670-674 (2007).

Gao et al. Hydrogen-Rich Saline Attenuates Cardiac and Hepatic Injury in Doxorubicin Rat Model by Inhibiting Inflammation and Apoptosis. Mediators Inflammation 2016:1320365 (2016).

General Electric. Size Exclusion Chromatography Principles and Methods. GE Healthcare Life Sciences (2000).

Goodall. Hydrogen Made by the Electrolysis of Water Is Now Cost-Competitive and Gives Us Another Building Block for the Low-Carbon Economy. Carbon Commentary, Carbon Commentary, Available at: https://www.carboncommentary.com/blog/2017/7/5/hydrogen-made-by-the-electrolysis-of-water-is-now-cost-competitive-and-gives-us-another-building-block-for- the-low-carbon-economy (Jul. 5, 2017).

Huang. Molecular hydrogen: a therapeutic antioxidant and beyond. Medical Gas Research 6(4):219-222 (2016).

Ichihara et al. Biological effects and the Underlying Mechanisms of Molecular Hydrogen. A Comprehensive Review of 321 Original Articles. Med. Gas Res. 5:12 (2015).

Ingredients. aloecream.biz, aloecream.biz, www.aloecream.biz/ingredients/ (2013).

Kamimura et al. Molecular Hydrogen Improves Obesity and Diabetes by Inducing Hepatic FGF21 and Stimulating Energy Metabolism in db/db Mice. Obesity 19(7):1396-1403 (2011).

Keithyley et al. Safety and efficacy of glucomannan for weight loss in overweight and moderately obese adults. J Obesity 2013:610908 (2013).

Kim et al. Distribution of glucomannans and xylans in poplar xylem and their changes under tension stress. Planta 236:35-50 (2012).

Lee et al. Antibacterial Activity of Hydrogen-Rich Water Against Oral Bacteria. Int. J. Oral Biol. 38 (2):81-85 (2013).

Li et al. Ultrasonic degradation kinetics and rheological profiles of a food polysaccharide (konjac glucomannan) in water. Food Hydrocolloids 70:14-19 (2017).

Liu et al. High efficiency hydrogen evolution from native biomass electrolysis. Energy Environ. Sci. 9:467-472 (2016).

Liu et al. Supplementary Information for High efficiency hydrogen evolution from native biomass electrolysis. Energy Environ. Sci. 9:467-472 (2016).

Nakamura et al. Mechanisms of microbial hydrogen disposal in the human colon and implications for health and disease. Annu. Rev. Food Sci. Technol. 1:363-395 (2010).

Nakao et al. Effectiveness of Hydrogen Rich Water on Antioxidant Status of Subjects with Potential Metabolic Syndrome—An Open Label Pilot Study. J Clin Biochemistry and Nutrition 46(2):140-149 (2010).

Ohata. Recent Progress Toward Hydrogen Medicine: Potential of Molecular Hydrogen for Preventative and Therapeutic Applications. Curr. Pharm. Des. 17:2241-2252 (2011).

Ohsawa et al. Hydrogen Acts as a Therapeutic Anti-oxidant by Selectively Reducing Cytotoxic Oxygen Radicals. Nature Medicine 13(6):688-694 (2007).

Onakpoya et al. The efficacy of glucomannan supplementation in overweight and obesity: a systematic review and meta-analysis of randomized clinical trials. J Am Coll Nutr. 33(1):70-78 (2014).

PCT/US2019/042833 International Search Report and Written Opinion dated Nov. 20, 2019.

Penders et al. ONOOH does not react with H2: Potential beneficial effects of H2 as an antioxidant by selective reaction with hydroxyl radicals and peroxynitrite. Free Radical Biol Med. 75:191-4 (2014).

Perman. Role of pH in Production of Hydrogen from Carbohydrates by Colonic Bacterial Flora. J. Clin. Invest. 67:643-650 (1981).

Pettersen. Chapter 2: The Chemical Composition of Wood. The Chemistry of Solid Wood 207:57-126 (1984).

Tang et al. Construction and Evaluation of Fibrillar Composite Hydrogel of Collagen/Konjac Glucomannan for Potential Biomedical Applications. Regenerative Biomaterials 5(4):239-250 (2018).

Uan et al. Evolution of Hydrogen from Magnesium Alloy Scraps in Citric Acid—Added Seawater without Catalyst. International J. of Hydrogen Energy 34(15):6137-6142 (2009).

U.S. Appl. No. 16/736,749 Office Action dated Aug. 6, 2021.

U.S. Appl. No. 16/736,749 Office Action dated Dec. 17, 2020.

U.S. Appl. No. 16/736,749 Office Action dated Sep. 25, 2020.

Walsh et al. Effect of Glucomannan on Obese Patients: A Clinical Study. Intl. J. of Obesity 8:289-293 (1984).

Wang et al. Interactions between Carboxymethyl Konjac Glucomannan and Soy Protein Isolate in Blended Films. Carbohydrate Polymers 101:136-145 (2014).

Yu et al. Effects of Concentrations of NaCl and Organic Acid on Generation 0f Hydrogen from Magnesium Metal Scrap. International J. of Hydrogen Energy 37(4):3033-3040 (2012).

Zeng et al. Progress in the study of biological effects of hydrogen on higher plants and its promising application in agriculture. Medical Gas Research 4:15 (2014).

Zhang et al. Anti-inflammatory Effect of Hydrogen-Rich Saline in a Rat Model of Regional Myocardial Ischemia and Reperfusion. International Journal of Cardiology 148(1):91-95 (2011).

Zheng et al. Saturated Hydrogen Saline Protects the Lung Against Oxygen Toxicity. Undersea and Hyperbaric Medicine 37:185-192 (2010).

Zhu et al. Ultrasonic degradation of konjac glucomannan and the effect of freezing combined with alkali treatment on their rheological profiles. Molecules 24(10):1860 (2019).

Zou et al. Hydrogen production from pyrolysis catalytic reforming of cellulose in the presence of K alkali m et al. International Journal of Hydrogen Energy 41(25):10598-10607 (2016).

Constitution et al. (Sep. 2017) "Functional Foods", Chinese Agricultural University Press, 227 (4 pages).

Pan, Daodong (Jan. 2006) "Functional food additives", China Light Industry Press, first edition, 162 (5 pages).

Toake et al. (Jan. 2014) "Gas Biomedicine", Second Military Medical University Press, 1st edition, 71-81 (34 pages).

* cited by examiner

COMPOSITION AND METHODS FOR GENERATING AND SUSTAINING MOLECULAR HYDROGEN ($H_2$) IN AQUEOUS SYSTEMS

CROSS-REFERENCE

This application is a continuation of U.S. patent application Ser. No. 16/736,749 filed Jan. 7, 2020, which is a continuation of International Patent Application No. PCT/US2019/042833 filed on Jul. 22, 2019, which claims the benefit of U.S. Provisional Application No. 62/764,222, filed Jul. 23, 2018, each of which is incorporated herein by reference.

BACKGROUND

The health benefits of administering molecular hydrogen to humans and animals by various routes, including IV, oral, transdermal, and inhalation have been. Initially, molecular hydrogen was believed to function as an antioxidant by direct reaction with hydroxyl radicals and peroxynitrite, while leaving the signaling reactive oxygen species-superoxide and hydrogen peroxide, unchanged.

Molecular hydrogen is used for wellness, anti-aging, as well as prevention and treatment of numerous diseases. Molecular hydrogen is readily absorbed into tissues. The duration of $H_2$ in the body is short-lived, since it readily diffuses in and out of tissues. Sustaining molecular hydrogen in the tissues of humans and animals is needed for increasing the efficacy of molecular hydrogen for reduction of tissue damage, effects on slowing aging and slowing the progression of chronic degenerative diseases as well as for body weight control. A means of generating and retaining molecular hydrogen in the body, in a safe, economic, and consumer-friendly manner, is needed to advance its use as a therapeutic agent.

SUMMARY

Provided herein are methods of generating an aqueous glucomannan solution containing molecular hydrogen, the method comprising: providing a volume of an aqueous solvent; and adding from about 0.00001% w/v to about 7.5% w/v glucomannan and about 0.005% to about 2.0% w/v magnesium metal powder to the aqueous solvent, wherein the generated glucomannan solution has an increased volume which is at least 0.01%, at least 0.1%, at least 1%, at least 10%, or at least 20% greater than the volume of a corresponding glucomannan solution which does not comprise $H_2$; wherein the generated glucomannan solution comprises an initial $H_2$ concentration of greater than about 100 ppb (parts per billion); and wherein, upon exposure of the glucomannan solution to standard temperature and pressure (STP) for 240 minutes after its generation, the glucomannan solution comprises an $H_2$ concentration at least about 50% or at least about 70% of the initial $H_2$ concentration.

Provided herein are methods of generating a glucomannan solution, the method comprising: providing a volume of an aqueous solvent; generating or sequestering $H_2$ in the aqueous solvent; and adding glucomannan to the aqueous solvent, wherein the glucomannan solution has an increased volume which is about 0.01%, at least 0.1%, at least 1%, at least 10%, or at least 20% greater than the volume of a corresponding glucomannan solution which does not comprise $H_2$; wherein the generated glucomannan solution comprises an initial $H_2$ concentration of greater than about 100 ppb (parts per billion); and wherein, upon exposure of the glucomannan solution to standard temperature and pressure (STP) for 240 minutes after its generation, the glucomannan solution retains at least 50% of its original concentration of $H_2$. Further provided are methods, wherein the aqueous solvent comprises water. Further provided are methods, wherein the aqueous solvent is water. Further provided are methods, wherein the generated glucomannan solution has a glucomannan concentration from about 0.00001% w/v to about 7.5% w/v. Further provided are methods, wherein the generated glucomannan solution is a gel. Further provided are methods, wherein the generated glucomannan solution is a flowable liquid. Further provided are methods, wherein the generated glucomannan solution comprises gaseous $H_2$. Further provided are methods, wherein, upon exposure of the glucomannan solution to standard temperature and pressure (STP) for 240 minutes after its generation, the glucomannan solution comprises an $H_2$ concentration at least about 75%, at least about 80%, at least about 85%, at least about 90%, at least about 95%, or at least about 99% of the initial $H_2$ concentration. Further provided are methods, wherein the volume of the generated glucomannan solution comprising $H_2$ is at least 1%, at least 10%, at least 20%, at least 30%, or at least 50% greater than the volume of the aqueous solvent. In some methods provided herein further comprise a step of treating the aqueous solvent with electrolysis, thereby generating $H_2$ in the aqueous solvent, prior to, during, or subsequent to adding the glucomannan to the aqueous solvent. Further provided are methods, wherein the glucomannan solution comprises a base metal. Further provided are methods, wherein the aqueous solvent comprises the base metal. Further provided are methods, wherein a base metal is added to the aqueous solvent prior to the addition of the glucomannan to the aqueous solvent. Further provided are methods, wherein the base metal is selected from the list consisting of lithium, potassium, strontium, calcium, sodium, magnesium metal powder, aluminum, zinc, chromium, manganese, iron, and any combination thereof. Further provided are methods, wherein the base metal is magnesium metal powder. Further provided are methods, wherein the magnesium metal powder is present in the generated glucomannan solution in an amount from about 0.00001% w/v to about 2% w/v. Further provided are methods, wherein the generated glucomannan solution further comprises an organic acid. Further provided are methods, wherein the organic acid is selected from the list consisting of citric acid, malic acid, lactic acid, acetic acid, tartaric acid, succinic acid, phosphoric acid or any combination thereof. Further provided are methods, wherein the citric acid is present in an amount from about 0.1% w/v to about 15% w/v. Further provided are methods, wherein the malic acid is present in an amount from about 1% (w/v) to about 50% w/v. Further provided are methods, wherein the lactic acid is present in an amount from about 1% w/v to about 10% w/v. Further provided are methods, wherein the acetic acid is present in an amount from about 0.5% v/v to about 3% v/v. Further provided are methods, wherein the tartaric acid is present in an amount from about 1% w/v to about 10% w/v. Further provided are methods, wherein the succinic acid is present in an amount from about 1% w/v to about 10% w/v. Further provided are methods, wherein the phosphoric acid is present in an amount from about 1% v/v to about 10% v/v. Some methods provided herein further comprise a step of diffusing $H_2$ in to the aqueous solvent or the glucomannan solution from a pressurized environment. Some methods provided herein further comprise a step of exposing the generated glucomannan solution to electrolysis, thereby generating thin the glucomannan solution. Further provided are methods, wherein the initial $H_2$ concentration is achieved during generation of the glucomannan solution. Further provided are methods, wherein the initial $H_2$ concentration is achieved prior to generation of the glucomannan solution. Further provided are methods, further comprising an isolating step, wherein bubbles in the glucomannan solution smaller than 37 microns are isolated. Further provided are methods, wherein the isolating is by filtration. Further provided are methods, wherein the isolating is by centrifugation. Further provided are methods, wherein the isolating is by size exclusion chromatography.

Provided herein are compositions comprising a glucomannan solution and further comprising hydrogen ($H_2$) at a concentration of greater than about 100 ppb (parts per billion); and wherein, upon exposure of the glucomannan solution to standard temperature and pressure (STP) for 240 minutes, the concentration of hydrogen in the glucomannan solution declines by less than 50% or less than 30%. Further provided herein are compositions, further comprising an aqueous solvent. Further provided herein are compositions, wherein the aqueous solvent is water. Further provided herein are compositions, wherein the concentration of glucomannan in the glucomannan solution is from about 0.00001% w/v to about 7.5% w/v. Further provided herein are compositions, wherein the glucomannan solution is a gel. Further provided herein are compositions, wherein the glucomannan solution is a flowable liquid. Further provided herein are compositions, wherein the $H_2$ is present in the glucomannan solution in a gaseous form. Further provided herein are compositions, wherein the $H_2$ concentration 240 minutes after generation of the glucomannan solution is at least about 75%, at least about 80%, at least about 85%, at least about 90%, at least about 95%, or at least about 99% of the initial $H_2$ concentration. Further provided herein are compositions, wherein the volume of the glucomannan solution comprising $H_2$ is at least 1%, at least 10%, at least 20%, at least 30%, or at least 50% greater than the volume of the aqueous solvent. Further provided herein are compositions, wherein the glucomannan solution comprises a base metal. Further provided herein are compositions, wherein the composition comprises a base metal. Further provided herein are compositions, wherein the aqueous solvent comprises a base metal. Further provided herein are compositions, wherein the base metal is selected from the group consisting of lithium, potassium, strontium, calcium, sodium, magnesium metal powder, aluminum, zinc, chromium, manganese, iron, and any combination thereof. Further provided herein are compositions, wherein the base metal is magnesium metal powder. Further provided herein are compositions, wherein the magnesium metal powder is present in the glucomannan solution in an amount from about 0.00001% w/v to about 2% w/v. Further provided herein are compositions, wherein the glucomannan solution further comprises an organic acid. Further provided herein are compositions, wherein the organic acid is selected from the group consisting of citric acid, malic acid, lactic acid, acetic acid, tartaric acid, succinic acid, phosphoric acid, and any combination thereof. Further provided herein are compositions, wherein the citric acid is present in an amount from about 0.1% w/v to about 15% w/v. Further provided herein are compositions, wherein the malic acid is present in an amount from about 1% w/v to about 50% w/v. Further provided herein are compositions, wherein the lactic acid is present in an amount from about 1% w/v to about 10% w/v. Further provided herein are compositions, wherein the acetic acid is present in an amount from about 0.5% v/v to about 3% v/v. Further provided herein are compositions, wherein the tartaric acid is present in an amount from about 1% w/v to about 10% w/v. Further provided herein are compositions, wherein the succinic acid is present in an amount from about 1% w/v to about 10% w/v. Further provided herein are compositions, wherein the phosphoric acid is present in an amount from about 1% v/v to about 10% v/v. Further provided herein are compositions, wherein the composition is in a capsule or gel.

Provided herein are glucomannan solutions comprising a concentration of glucomannan and hydrogen ($H_2$). Further provided herein are solutions, wherein the hydrogen ($H_2$) is present at a concentration of greater than about 100 ppb (parts per billion) hydrogen ($H_2$). Further provided herein are solutions, wherein upon exposure to standard temperature and pressure (STP) for 240 minutes, the $H_2$ concentration is at least about 70% of the initial $H_2$ concentration as measured in parts per billion (ppb). Further provided herein are solutions, wherein the glucomannan concentration is from about 0.00001% to about 7.5%. Further provided herein are solutions, wherein the solution is a gel. Further provided herein are solutions, wherein the solution is a flowable liquid. Further provided herein are solutions, wherein the $H_2$ is present in a gaseous form. Further provided herein are solutions, wherein, upon exposure of the glucomannan solution to standard temperature and pressure (STP) for 240 minutes, the concentration of hydrogen in the glucomannan solution declines by less than 1%, less than 5%, less than 10%, less than 15%, less than 20%, less than 25%, or less than 30%. as measured in parts per billion (ppb). Further provided herein are solutions, wherein, upon exposure of the glucomannan solution to standard temperature and pressure (STP) for 240 minutes, the concentration of hydrogen in the glucomannan solution is at least 70% of the $H_2$ concentration in the solution prior to the exposure as measured in parts per billion (ppb). Further provided herein are solutions, further comprising a base metal. Further provided herein are solutions, wherein the base metal is selected from the group consisting of lithium, potassium, strontium, calcium, sodium, magnesium metal powder, aluminum, zinc, chromium, manganese, iron, and any combination thereof. Further provided herein are solutions, wherein the base metal is magnesium metal powder. Further provided herein are solutions, wherein the magnesium metal powder is present in the glucomannan solution in an amount from about 0.00001% w/v to about 2% w/v. Further provided herein are solutions, further comprising an organic acid. Further provided herein are solutions, wherein the organic acid is selected from the list consisting of citric acid, malic acid, lactic acid, acetic acid, tartaric acid, succinic acid, phosphoric acid or any combination thereof. Further provided herein are solutions, wherein the citric acid is present in an amount from about 0.1% w/v to about 15% w/v. Further provided herein are solutions, wherein the malic acid is present in an amount from about 1% (w/v) to about 50% w/v. Further provided herein are solutions, wherein the lactic acid is present in an amount from about 1% w/v to about 10% w/v. Further provided herein are solutions, wherein the acetic acid is present in an amount from about 0.5% v/v to about 3% v/v. Further provided herein are solutions, wherein the tartaric acid is present in an amount from about 1% w/v to about 10% w/v. Further provided herein are solutions, wherein the succinic acid is present in an amount from about 1% w/v to about 10% w/v. Further provided herein are solutions, wherein the phosphoric acid is present in an amount from about 1% v/v to about 10% v/v.

Provided herein are methods, compositions, and solutions as described herein, further formulated for oral administration. Provided herein are methods, compositions, and solutions as described herein, further formulated for rectal administration. Further provided are methods, compositions, or solutions, further formulated for oral delivery. Further provided are methods, compositions, or solutions, further formulated for esophageal delivery. Further provided are methods, compositions, or solutions, further formulated for gastric delivery. Further provided are methods, compositions, or solutions, further formulated for duodenal delivery. Further provided are methods, compositions, or solutions, further formulated for delivery to the small intestine. Further provided are methods, compositions, or solutions, further formulated for delivery to the large intestine. Further provided are methods, compositions, or solutions, further formulated for delivery to the colon.

Provided herein are methods, compositions, and solutions as described herein, further formulated for parenteral delivery.

Provided herein are compositions and solutions as described herein, further formulated for a topical dosage form. Further provided herein are compositions and solutions, wherein the topical dosage form is a cream, gel, foam, ointment, lotion, or liquid.

Provided herein is a bandage comprising compositions or solutions as described herein.

Provided herein is a kit for treating a skin condition, comprising: a container comprising a composition or solution described herein; instructions for applying the composition or solution topically to the skin.

Provided herein is a kit for treating a gastrointestinal condition, comprising: a container comprising a composition or solution as described herein; and instructions for oral or rectal administration of the composition or solution.

Provided herein is a kit for treating an inflammatory disease, comprising: a container comprising a composition or solution as described herein; and instructions for administration of the composition or solution to treat the inflammatory disease.

Provided herein is a kit for treating obesity, comprising: a container comprising a composition or solution as described herein; and instructions for oral administration of the composition or solution.

Provided herein are methods for treating a skin condition, comprising administering a composition or solution as described herein to the skin of a subject in need thereof.

Provided herein are methods for treating a gastrointestinal condition, comprising administering a composition or solution as described herein, to a subject in need thereof.

Provided herein are methods for treating an inflammatory condition, comprising administering a composition or solution as described herein, to a subject in need thereof.

Provided herein are methods for treating obesity, comprising administering a composition or solution described herein, to a subject in need thereof.

Provided herein are methods of providing $H_2$ as a nutritional supplement to a subject in need thereof, comprising providing a composition or solution as described herein to a subject in need thereof.

Provided herein are methods of providing $H_2$ to a body or container of water comprising aquatic or plant life, comprising contacting the water with a composition or the solution as described herein.

Provided herein are methods of sequestering $H_2$ from an aqueous solution in need thereof, comprising contacting the aqueous solution with a composition or solution as described herein.

Provided herein are devices comprising a composition or solution as described herein, flowably connected to a water source, allowing contact between the composition described herein and the water source.

Provided herein are compositions comprising a base metal and glucomannan. Further provided are compositions, wherein the base metal is selected from the list consisting of lithium, potassium, strontium, calcium, sodium, magnesium metal powder, aluminum, zinc, chromium, manganese, iron, and any combination thereof. Further provided are compositions, wherein the base metal is magnesium metal powder. Further provided are compositions, further comprising an organic acid. Further provided are compositions, wherein the organic acid is selected from the list consisting of citric acid, malic acid, lactic acid, acetic acid, tartaric acid, succinic acid, phosphoric acid or any combination thereof. Further provided are compositions, wherein the composition is in a powder form. Further provided are compositions, wherein the composition is substantially free of water. Further provided are compositions, wherein the composition is in a capsule or gel.

Provided herein are glucomannan solutions produced by a method as described herein. Provided herein are methods of generating a glucomannan solution, comprising generation of a glucomannan solution that comprises $H_2$. Provided herein are methods of generating a glucomannan solution, comprising adding a magnesium metal powder and glucomannan to an aqueous solvent. Provided herein are methods of generating a glucomannan solution that retains molecular hydrogen longer than a solution without glucomannan, the method comprising: providing a relatively large volume of an aqueous solvent; adding an amount of glucomannan to the aqueous solvent; and generating and/or infusing an amount of molecular hydrogen into the aqueous solvent, wherein the glucomannan solution has a volume from zero to more than 100% greater than the volume of the aqueous solvent, wherein the increase in volume of the glucomannan solution over the aqueous solvent is dependent on the amount of glucomannan and molecular hydrogen in the glucomannan solution, wherein the generated glucomannan solution comprises an initial $H_2$ concentration of greater than about 100 ppb (parts per billion), and wherein, upon exposure of the glucomannan solution to standard temperature and pressure for at least four hours, the glucomannan solution comprises a level of molecular hydrogen greater than a level of molecular hydrogen in a comparable aqueous solution without glucomannan. Further provided herein are methods, wherein the generated glucomannan solution has a glucomannan concentration from about 0.00001% w/v to about 7.5% w/v. Further provided herein are methods, wherein the generated glucomannan solution is a gel. Further provided herein are methods, wherein the generated glucomannan solution is a flowable liquid. Further provided herein are methods, wherein the generated glucomannan solution comprises gaseous $H_2$. Further provided herein are methods, wherein, upon exposure of the glucomannan solution to standard temperature and pressure (STP) for 240 minutes after its generation, the glucomannan solution comprises an $H_2$ concentration at least about 75%, at least about 80%, at least about 85%, at least about 90%, at least about 95%, or at least about 99% of the initial $H_2$ concentration. Further provided herein are methods, wherein the volume of the generated glucomannan solution comprising $H_2$ is at least 1%, at least 10%, at least 20%, at least 30%, or at least 50% greater than the volume of the aqueous solvent. Further provided herein are methods, further comprising a step of treating the aqueous solvent with electrolysis, thereby generating $H_2$ in the aqueous solvent, prior to adding the glucomannan to the aqueous solvent. Further provided herein are methods, wherein the glucomannan solution comprises a base metal. Further provided herein are methods, wherein the base metal is selected from the list consisting of lithium, potassium, strontium, calcium, sodium, magnesium metal powder, aluminum, zinc, chromium, manganese, iron, and any combination thereof. Further provided herein are methods, wherein the base metal is magnesium metal powder. Further provided herein are methods, wherein the magnesium metal powder is present in the generated glucomannan solution in an amount from about 0.00001% w/v to about 2% w/v. Further provided herein are methods, wherein the generated glucomannan solution further comprises an organic acid. Further provided herein are methods, wherein the organic acid is selected from the list consisting of citric acid, malic acid, lactic acid, acetic acid, tartaric acid, succinic acid, phosphoric acid or any combination thereof. Further provided herein are methods, wherein the citric acid is present in an amount from about 0.1% w/v to about 15% w/v. Further provided herein are methods, wherein the malic acid is present in an amount from about 1% (w/v) to about 50% w/v. Further provided herein are methods, wherein the lactic acid is present in an amount from about 1% w/v to about 10% w/v. Further provided herein are methods, wherein the acetic acid is present in an amount from about 0.5% v/v to about 3% v/v. Further provided herein are methods, wherein the tartaric acid is present in an amount from about 1% w/v to about 10% w/v. Further provided herein are methods, wherein the succinic acid is present in an amount from about 1% w/v to about 10% w/v. Further provided herein are methods, wherein the phosphoric acid is present in an amount from about 1% v/v to about 10% v/v. Further provided herein are methods, further comprising a step of diffusing $H_2$ in to the aqueous solvent or the glucomannan solution from a pressurized environment. Further provided herein are methods, further comprising a step of exposing the generated glucomannan solution to electrolysis, thereby generating $H_2$ in the glucomannan solution. Further provided herein are methods, wherein an initial $H_2$ concentration is achieved during generation of the glucomannan solution. Further provided herein are methods, wherein the initial $H_2$ concentration is achieved prior to generation of the glucomannan solution. Further provided herein are methods, further comprising an isolating step, wherein bubbles in the glucomannan solution smaller than 37 microns are isolated. Further provided herein are methods, wherein the isolating is by filtration. Further provided herein are methods, wherein the isolating is by centrifugation. Further provided herein are methods, wherein the isolating is by size exclusion chromatography.

Provided herein are $H_2$-generating compositions comprising: lactic acid; glucomannan; magnesium metal powder; glycerin; and an aqueous solvent. Provided herein are $H_2$-generating compositions comprising: an organic acid; glucomannan; magnesium metal powder; glycerin; and an aqueous solvent. Further provided herein are compositions, wherein the composition is a cream, gel, foam, ointment, lotion, or liquid. Provided herein are, wherein the composition is adapted for application to the skin of a subject. Provided herein are, wherein the composition provides a moisturizing effect to the skin of the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
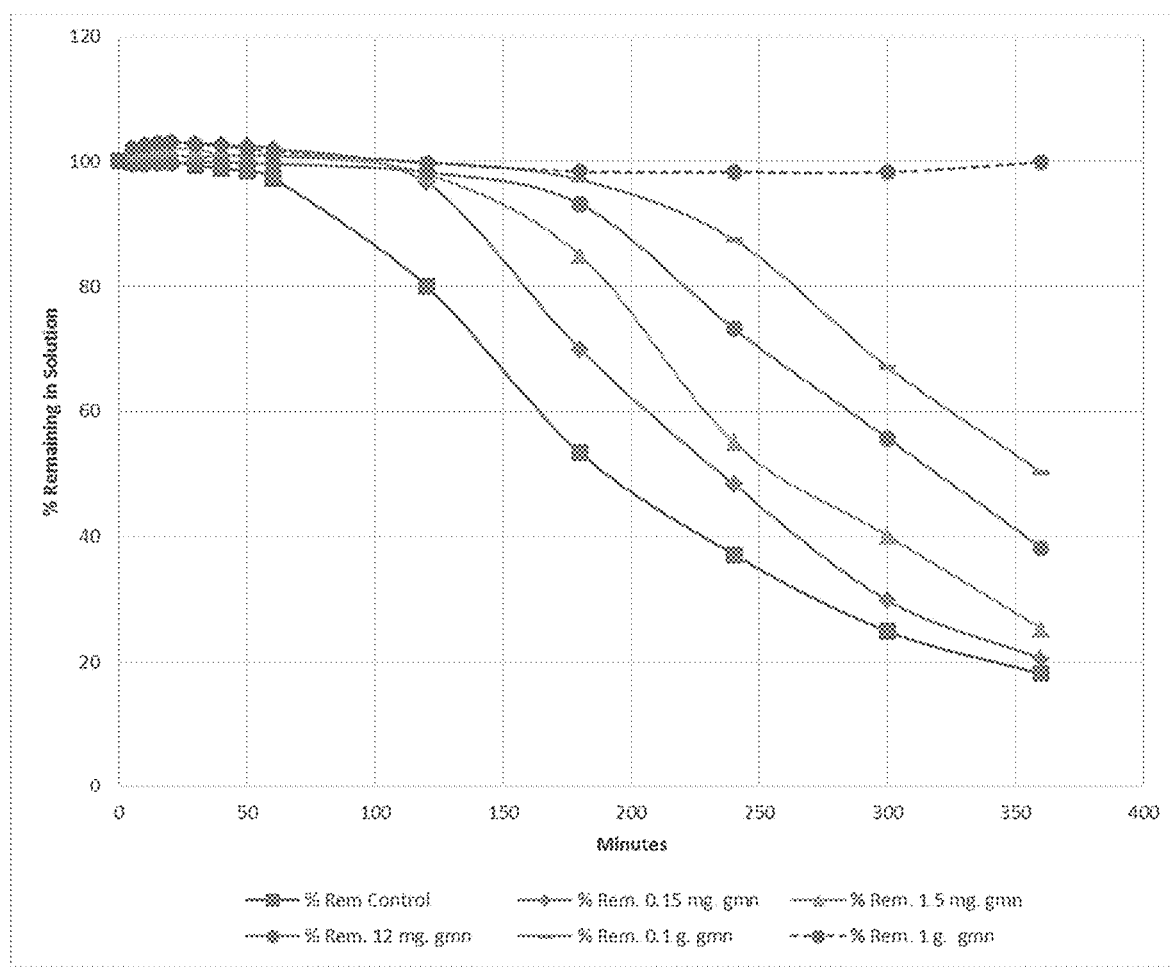
FIG. 1 indicates the time course of molecular hydrogen ($H_2$) depletion from glucomannan solutions.

Provided herein are compositions and methods to generate molecular hydrogen in aqueous compositions. The compositions provided herein maintain levels of molecular hydrogen ($H_2$) within the composition for longer periods of time and release the molecular hydrogen more slowly than in other compositions previously known in the art.

I. GENERATION OF MOLECULAR HYDROGEN

The concentration of hydrogen ($H_2$) is often reported in molarity (moles/liter (M) or millimoles/L (mM)), parts per million (ppm), parts per billion (ppb) or milligrams per liter (mg/L). In dilute concentrations, 1 ppm is about the same as 1 mg/L and they are often used interchangeably. The molar mass of molecular hydrogen is about 2 mg/millimole, 1 mg is approximately equivalent to 0.5 moles, therefore 1 ppm=1 mg/L=0.5 mM.

The solubility of gas dissolved in water is a function of pressure and temperature according to Henry's law:

$C=P/K_H$ where C represents the concentration of the dissolved gas (mol/L), $K_H$ is a constant characteristic of the particular gas (Latm/mol), and P represents the partial pressure of the specific gas above the solution (atm). Given hydrogen ($H_2$) gas constitutes $5.5 \times 10^{-5}$% of atmosphere, and Henry's Constant at 25° C. is 1282.05 1*atm/mol, the concentration of hydrogen in water at 1 atmosphere is $4.29 \times 10^{-7}$ mM, $8.65 \times 10^{-7}$, or $8.65 \times 10^{-4}$ ppb.

Generally known methods of generating molecular hydrogen for health care purposes include: electrolysis of water, reaction of base metals and metal hydrides with water, direct water splitting through vibrating piezoelectric zinc oxide microfibers in aqueous solutions, and pressurizing molecular hydrogen into water in containers resistant to permeation.

In some embodiments described herein, the molecular hydrogen is generated using electrolysis. Several commercial electrolysis devices are available for generating molecular hydrogen from water. These devices are limited in that they require 'purified' water. 'Purified' water is defined here as water that is free of contaminants. Of most concern is the presence of those electrolytes in water that can form deposits on the electrodes of the electrolysis device and render it useless. 'Purified' water can be produced by distillation, reverse osmosis, ion exchange or any method that results in water that is free of, or very low in, ions and organic contaminants. For electrolysis, the pH should be near neutral and free of electrolytes that can degrade the electrodes. Use of electrolytes greatly reduces the lifetime of electrodes. A major disadvantage in using 'purified' water, e.g., distilled water, is the very low output of $H_2$. To increase molecular hydrogen generation from 'purified' water, high voltage, unsafe for consumers, is generally used.

In some embodiments described herein, the molecular hydrogen is generated using electrolysis.

II. GLUCOMANNAN

Konjac glucomannan is derived from the tuber of the *Amorphophallus konjac* plant, which is prevalent in Asian countries including China and Japan. Glucomannan is used in preparing several types of foods. Glucomannan flour contains a variety of insoluble substances as well as water-soluble substances. Glucomannan is a polymer composed of the monosaccharides D-glucose and D-mannose. It forms a highly viscous sol when constituted with water at concentrations of pure glucomannan above 1.0% w/w. It is the only biopolymer currently known to form an aqueous gel at room temperature. The gel forms within a few minutes of mixing with water. U.S. Pat. No. 5,486,364 describes processes for preparing konjac glucomannan and is incorporated herein for such disclosure. In some embodiments, compositions described herein comprise clarified glucomannan that forms a clear sol with water. In some embodiments, compositions described herein comprise rapidly hydratable konjac glucomannan that is characterized by at least a 60% viscosity gain after a 10 minute period. In some embodiments, compositions described herein comprise chemically modified glucomannans.

Glucomannan has been used in Asia, particularly in China, for over 2,000 years in applications for detoxification, tumor suppression, blood stasis alleviation and to treat ailments such as asthma, cough, hernia, breast pain, burns as well as hematological and skin disorders. Glucomannan has additionally been shown to affect body weight reduction in animal and human studies.

In some embodiments described herein, compositions comprise from about 0.0001% w/v to about 15% w/v glucomannan. In some embodiments, compositions comprise from about 0.0001% to about 0.001% glucomannan. In some embodiments, compositions comprise from about 0.001% to about 0.01% glucomannan. In some embodiments, compositions comprise from about 0.01% to about 0.1% glucomannan. In some embodiments, compositions comprise from about 0.1% to about 1.0% glucomannan. In some embodiments, compositions comprise from about 1.0% to about 15% glucomannan.

III. MAGNESIUM METAL POWDER

Several base metals, for example, lithium, potassium, strontium, calcium, sodium, magnesium metal powder, aluminum, zinc, chromium, manganese and iron, when reacting with water, generate molecular hydrogen. Conditions such as temperature, or the presence of acids, bases, and other catalysts can affect the rate of the reaction. Magnesium metal powder is preferred for human consumption due to its wide margin of safety, established health benefits as an essential element and ease of molecular hydrogen generation under room temperature, atmospheric pressure, and mild acidic or basic conditions.

In some embodiments described herein, compositions comprise lithium, potassium, strontium, calcium, sodium, magnesium metal powder, aluminum, zinc, chromium, manganese, iron, or any combination thereof. In some embodiments, compositions comprise lithium. In some embodiments, compositions comprise potassium. In some embodiments, compositions comprise strontium. In some embodiments, compositions comprise calcium. In some embodiments, compositions comprise sodium. In some embodiments, compositions comprise magnesium metal powder. In some embodiments, compositions comprise aluminum. In some embodiments, compositions comprise zinc. In some embodiments, compositions comprise chromium. In some embodiments, compositions comprise iron.

In embodiments described herein, compositions comprise from about 0.001% w/v to about 2% w/v of the base metal. In some embodiments, compositions comprise from about 0.001% w/v to about 0.01% w/v of the base metal. In some embodiments, compositions comprise from about 0.005% w/v to about 0.05% w/v of the base metal. In some embodiments, compositions comprise from about 0.01% w/v to about 0.1% w/v of the base metal. In some embodiments, compositions comprise from about 0.05% w/v to about 0.5% w/v of the base metal. In some embodiments, compositions comprise from about 0.1% w/v to about 1% w/v of the base metal. In some embodiments, compositions comprise from about 0.5% w/v to about 2% w/v of the base metal.

In some embodiments, compositions described herein comprise magnesium metal powder (Mg). In some embodiments, compositions comprise from about 0.001% to w/v to about 2% w/v magnesium metal powder. In some embodiments, compositions comprise from about 0.001% w/v to about 0.01% w/v magnesium metal powder. In some embodiments, compositions comprise from about 0.005% w/v to about 0.05% w/v magnesium metal powder. In some embodiments, compositions comprise from about 0.01% w/v to about 0.1% w/v magnesium metal powder. In some embodiments, compositions comprise from about 0.05% w/v to about 0.5% w/v magnesium metal powder. In some embodiments, compositions comprise from about 0.1% w/v to about 1% w/v magnesium metal powder. In some embodiments, compositions comprise from about 0.5% w/v to about 2% w/v magnesium metal powder.

Organic acids have been shown to be effective in accelerating the generation of molecular hydrogen in the reaction of magnesium metal powder with water. (See, Uan, J-Y. et. al.(2009) J. of Hydrogen Energy 34 (15), 6137-6142, which is incorporated herein for such disclosure). Organic acids can include, without limitation, lactic acid, acetic acid, formic acid, citric acid, oxalic acid, uric acid, malic acid, or any combination thereof. In some embodiments, compositions comprise lactic acid. In some embodiments, compositions comprise acetic acid. In some embodiments, compositions comprise formic acid. In some embodiments, compositions comprise citric acid. In some embodiments, compositions comprise oxalic acid. In some embodiments, compositions comprise uric acid. In some embodiments, compositions comprise malic acid.

IV. COMMERCIAL PRODUCTS CONTAINING MAGNESIUM METAL POWDER

Products based upon magnesium metal powder, are known in the art for generating molecular hydrogen when reacted with water. Such products require acids or catalysts to rapidly generate molecular hydrogen from water. These products do not have a means of sustaining molecular hydrogen in solution or in the body.

V. RATIONALE FOR USE OF MAGNESIUM METAL POWDER

In some embodiments described herein, compositions comprise magnesium metal powder. Magnesium metal powder is safe to use for human and animal consumption. It is stable, readily generates molecular hydrogen, is inexpensive, and is commercially available. When reacting with water, it is converted to Generally Recognized as Safe (GRAS) magnesium hydroxide according the reaction

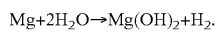
$Mg+2H_2O \rightarrow Mg(OH)_2+H_2$.

Magnesium hydroxide is an OTC drug approved laxative as well as approved as a GRAS food additive and supplement. Magnesium is an essential nutrient involved in over 400 enzymatic reactions in living systems. Magnesium metal reacts with water to produce molecular hydrogen and form magnesium hydroxide. This reaction is thermodynamically favorable, and its reaction rate is pH-dependent. Ionized magnesium in a salt form, as non-limiting examples, citrate, chloride, sulfate, or chelated magnesium, cannot generate molecular hydrogen in an aqueous environment. Further, covalently bound magnesium compounds such as magnesium oxide, magnesium hydroxide, magnesium carbonate cannot generate molecular hydrogen in an aqueous environment. The rate of reaction of magnesium metal powder with water depends on several factors, some of which are discussed below. The surface area of magnesium metal that will be exposed to water is a factor to consider. Basic physical chemistry would predict that the larger the surface area, the faster and more efficient the reaction. This otherwise obvious conclusion is modified by two factors: First, the larger the surface area and smaller the particle size, the more likely that magnesium metal can undergo a spontaneous and explosive reaction with oxygen. Thus, safety is an issue. Secondly, left alone or by a process of reducing the risk of spontaneous reaction with oxygen (or water), a magnesium oxide coat is spontaneously formed on the surface of magnesium metal particles through a process called passivation. Although this coat of magnesium oxide does not greatly reduce the amount of magnesium metal in large particles that can react with water, it potentially can reduce the amount of magnesium in small particles that can react with water. For example, the magnesium oxide coat on nanoparticles may constitute a significant percentage of the magnesium present-reducing the amount of magnesium metal available to react with water. All forms of magnesium metal, including but not limited to powders, pellets, and filings, will have some reactivity with water and oxygen. The point to be taken is that there is a particle size distribution of magnesium metal powder that is optimally reactive and safe to handle under Good Manufacturing Practice (GMP) conditions. Magnesium metal powder is generally available at up to 99.999% purity, with aluminum being the main impurity.

The size distribution of magnesium metal powder used in the studies described herein was determined using Fieldmaster® Sieves of 35, 60, 120, and 230 Mesh, corresponding, respectively to 500, 250, 125 and 63 microns. The size distribution was found to be: 0.7% equal to or greater than 500 microns; 1.2% 250-500 microns; 9.3% 125-250 microns; 38.2% at 63-125 microns, and 50.9% smaller than 63 microns.

VI. MAGNESIUM METAL POWDER PLUS GLUCOMANNAN POWDER

The reaction rate of magnesium metal powder with water in the presence of glucomannan is described herein, and depends on several factors, including pH and the presence of catalysts. For forming gels using magnesium metal powder-glucomannan complexes, a fast rate of molecular hydrogen production is not necessarily desirable. That is, more molecular hydrogen will be sequestered in the gel if the gel is formed before a significant percentage of the available molecular hydrogen is generated.

As is well known in the art, variation of pH from neutrality can accelerate the reaction of magnesium metal with water. Acidic conditions can include any organic or inorganic acid that lowers the pH below 7.0. Included are gastric fluids, acidic foods, and acidic aquatic environments. Examples of acids and/or their salts that can be used include citric acid, malic acid, adipic acid, fumaric acid, succinic acid, ascorbic acid, iso-ascorbic acid, salicylic acid, phosphoric acid, potassium sorbate and sodium bisulfite. Examples of antioxidants, that are salts of acids, include sodium ascorbate and potassium ascorbate. On the alkaline side, magnesium oxide, magnesium hydroxide, potassium and sodium hydroxide can be used to increase the pH to alkaline conditions. Combinations of these agents can be used to control the rates of reaction of magnesium metal in aqueous glucomannan at conditions that generate $H_2$ in solutions and gels.

In some embodiments described herein, compositions comprise an acid or antioxidant catalyst. In some embodiments, the compositions are formulated for oral administration for gastric delivery. In some embodiments, the oral formulation comprises capsules, powder, tablets or another delivery vehicle. In some embodiments, the composition formulation for gastric delivery utilizes the acidity of stomach fluid to catalyze the reaction of magnesium metal or a magnesium hydride with water to form the molecular hydrogen-rich solution or a viscous solution or a gel. Also, when adding a magnesium metal powder-glucomannan formulation to acidic products, such as tea or acidic beverages, the acidity of the product is more than sufficient to catalyze the reaction of water with magnesium metal powder to generate molecular hydrogen. In some embodiments, the composition comprises a base, for example, sodium bicarbonate, to modulate the reaction.

It has been found that when combining magnesium metal powder and glucomannan and mixing with water—that a hydrogen-rich solution, viscous solution or expansive gel with unexpected high sustainability of molecular hydrogen is created. Depending on the concentrations of magnesium metal powder and glucomannan, the pH and activity of water—the resulting solutions and gel-like structures display the following novel properties:

1. In a closed plastic container, at ambient temperature, molecular hydrogen remains in glucomannan solutions and gels, at a level of up to 60% of the original molecular hydrogen content—for over 39 days. (Ref: Table 3).
2. In a closed plastic container, at 1-4 degrees centigrade, molecular hydrogen remains in a glucomannan gel, at a level of up to 51% of the original $H_2$ content—for over 73 days. (Ref: Table 6)
3. In an open plastic container, at room temperature, molecular hydrogen remains in 0.15 to 1,000 mg/100 mL non-gelling, low viscosity aqueous solutions of glucomannan, at a level of up to 99% of the original $H_2$ content—for over 15 days. (Ref: Table 14)
4. In an open plastic container, at room temperature, molecular hydrogen remains in viscous glucomannan solutions, at a level of up to 50% of the original molecular hydrogen content—for over 15 days. (Ref: FIG. 1, Table 14).
5. When magnesium metal powder reacts with water in the presence of 1-10% glucomannan, it generates molecular hydrogen which expands the resultant aqueous gel by up to 83% v/v—depending on the pH and concentration of the constituents. (Ref: Table 2).
6. $H_2$ sequestration by magnesium metal powder-glucomannan gels creates aqueous gels of various density and porosity thereby affecting a desirable 'fluffy' texture-depending of the concentration of the basic constituents. (Ref: Tables 1 and 10).
7. Great tasting, 'fluffy' textured, nutritious aqueous magnesium metal powder-glucomannan gels, with health benefits, can be created by incorporating one or more of the following into the gels: sweeteners, flavoring agents, natural fruit and vegetable powders, tea powders, protein powders, vitamin powders, probiotic powders, prebiotics, drugs and nutritional supplements. (Ref: Tables 8 and 10).
8. Glucomannan, in aqueous solution, increases the yield of molecular hydrogen generation by affecting removal of the passivation coat of magnesium oxide from the surface of magnesium metal. (Ref: Table 14, FIG. 1).
9. Exposing aqueous solutions or gels of glucomannan to molecular hydrogen allows the sequestration of molecular hydrogen by glucomannan. (Ref: Table 15, FIG. 2).
10. Long lasting $H_2$ microbubble stability in non-viscous magnesium metal powder-glucomannan solutions, in an open system, at room temperature.
11. Creation of $H_2$ sustained release gels, of various rates of release, for nutrients, drugs and beneficial environmental factors, including $H_2$.

Furthermore, it has been conceived that the resulting molecular hydrogen-glucomannan gels and viscous solutions can be utilized to:

1. Provide extended, long lasting delivery of molecular hydrogen to the body of mammals through its persistence in the gastrointestinal tract and other tissues—such as skin;
2. Use of this biotechnology to produce hydrogen-rich magnesium metal powder-glucomannan gels that are low calorie, good tasting, filling, and long lasting due to floating and expanding in the upper G-I tract—properties that are useful for augmentation of fasting, anti-inflammatory, and weight control programs.
3. Provide molecular hydrogen-generating capsules or tablets, taken orally, that support weight control and fasting regimens by forming an expanded, floating gel in the aqueous acidic environment of the stomach—while reducing the inflammatory complications of obesity.
4. Provide extended, long lasting delivery of molecular hydrogen ($H_2$) to the oral cavity of humans and animals to treat plaque build-up, gingivitis, periodontal disease, and other inflammatory conditions of the oral cavity, esophagus and stomach.
5. $H_2$ generating magnesium metal powder-glucomannan gels that act as a sustained drug-delivery system in the upper G-I tract—for drugs that need to be held in the stomach for an extended period or need to be slowly released into the systemic circulation. Molecular hydrogen release will act synergistically with some of these drugs. Drugs that can eradicate Helicobacter pylori from the upper G-I Tract, treat and prevent gastric and duodenal ulcers, treat GERD are of most interest. Gel delivery of bismuth subsalicylate, with and without other drugs to treat G-I afflictions and infections is of interest.
6. Act as an extended release system for topical delivery of molecular hydrogen to dermal tissues for treatment of infections and inflammatory diseases.
7. Drugs delivered topically, for an extended time—or need to be slowly released into the systemic circulation. Hydrogen release will act synergistically with some of these drugs.
8. Enhanced growth and seed germination for aquatic plant, crustacean and fish life by providing a sustained release gel system for both molecular hydrogen and nutrients into aquatic systems.
9. Enhanced growth rates for farming of insects by providing a sustained release gel system for both molecular hydrogen and nutrients needed for accelerated growth.
10. Act both as a generator and storage vehicle for molecular hydrogen that can be used as a fuel, when harvested from the gel.

VII. MAGNESIUM METAL POWDER-GLUCOMANNAN GELS WITH EXCIPIENTS AND FUNCTIONAL AGENTS

In some embodiments described herein, compositions comprise additional excipients or functional agents. Excipients or functional agent included in some compositions described herein comprise sweeteners, flavoring agents, natural fruit and vegetable powders, tea powders, protein powders, vitamin powders, probiotic powders, anti-caking agents, preservatives, prebiotics, nutritional supplements, drugs, and food colorings.

In some embodiments, compositions comprise sweeteners, alone or in combination, including, but not limited to, acesulfame, aspartame, saccharin, sucralose, sucrose, monk fruit, glucose, fructose, xylitol, mannitol, glycerin, maltodextrin, inulin, and erythritol. Compositions described herein may contain sweeteners, alone or in combination, in a concentration of from about 0.1 to about 20% w/w of the composition. Compositions described herein may contain sweeteners, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, from about 0.1% to about 5%, from about 1% to about 10%, from about 5% to about 15%, or from about 10% to about 20%, or from about 0.1% to about 20% w/w of the composition.

In some embodiments, compositions comprise flavoring agents, alone or in combination, including, but not limited to, natural lemon powder, citric acid, malic acid, hydroxycitric acid, tartaric acid, adipic acid, vanillin, chocolate, cherry, pomegranate, raspberry, and strawberry flavoring. Compositions described herein may contain flavoring agents, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, about 35%, about 40%, about 45%, about 50%, from about 0.1% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, or from about 0.1% to about 50% w/w of the composition.

In some embodiments, compositions comprise water extracts of natural fruit powders, alone or in combination, including, but not limited to, bilberry, lemon, blueberry, cranberry, cinnamon, ginger, lemon balm, vanilla, pumpkin seed and strawberry. Compositions described herein may contain water extracts of natural fruit powders, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, about 35%, about 40%, about 45%, about 50%, from about 0.1% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, or from about 0.1% to about 50% w/w of the composition.

In some embodiments, compositions comprise water extracts of natural vegetable powders, alone or in combination, including, but not limited to, carrot juice, spinach, broccoli, sweet potato and white willow bark powder. Compositions described herein may contain water extracts of natural vegetable powders, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, about 35%, about 40%, about 45%, about 50%, from about 0.1% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, or from about 0.1% to about 50% w/w of the composition.

In some embodiments, compositions comprise herbal tea water extract powders, alone or in combination, including, but not limited to, white tea, green tea, Red Gush Chai, Matcha, Maca, Kombucha, Turmeric, Dandelion, Ginger, Lemon Ginger, Oolong, Rooibos, Fennell, Nettle Leaf, Peppermint, Echinacea, Valerian, Cinnamon Berry, Chamomile and Lavender tea. Compositions described herein may contain herbal tea water extract powders, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, about 35%, about 40%, about 45%, about 50%, about 55%, about 60%, about 65%, about 70%, from about 0.1% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, or from about 0.1% to about 70% w/w of the composition.

In some embodiments, compositions comprise protein powders, alone or in combination, including, but are not limited to, non-fat milk, 1% fat milk, 2% fat milk, whole milk, goat milk, rice milk, almond milk, soy milk, coconut, pea protein and brown rice protein. Compositions described herein may contain protein powders, alone or in combination, in a concentration of about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, about 35%, about 40%, about 45%, about 50%, from about 0.2% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, or from about 0.2% to about 50% w/w of the composition.

In some embodiments, compositions comprise vitamins or minerals, alone or in combination, including, but are not limited to, vitamin A, vitamin C, calcium, iron, vitamin D3, vitamin E, thiamin, riboflavin, niacin, vitamin B6, Folate, vitamin B12, biotin, pantothenic acid, phosphorous, iodine, magnesium metal powder, zinc, selenium, copper, manganese and chromium. Compositions described herein may contain vitamins or minerals, alone or in combination, in an amount of about 5%, about 6%, about 7%, about 8%, about 9%, about 10%, about 12%, about 14%, about 16%, about 18%, about 20%, %, about 25%, about 30%, about 35%, about 40%, about 45%, about 50%, about 55%, about 60%, about 65%, about 70%, about 75%, about 80%, about 85%, about 90%, about 95%, about 100%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 100%, or from about 5% to about 100% of the RDI (Required Daily Intake) for a healthy adult human.

In some embodiments, compositions comprise probiotics, alone or in combination, including, but not limited to *Bacillus coagulans, Bacillus subtilis, Bacillus infantis, Lac-*

*tobacillus longum, Lactobacillus casei, Lactobacillus acidophilus* and *Bifidobacterium*. Compositions described herein may contain probiotics, alone or in combination, in an amount of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, from about 0.1% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, or from about 0.1% to about 10% w/w of the composition.

In some embodiments, compositions comprise anti-caking agents, alone or in combination, including, but not limited to, calcium phosphate tribasic, calcium silicate, sodium alginate, cellulose, microcrystalline cellulose, xanthan gum, magnesium carbonate, magnesium oxide, magnesium silicate, and magnesium sulfate. Compositions described herein may contain anti-caking agents, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, from about 0.1% to about 2%, from about 0.5% to about 3%, from about 1% to about 4%, from about 2% to about 5%, or from about 0.1% to about 5% w/w of the composition.

In some embodiments, compositions comprise preservatives, alone or in combination, including, but not limited to, ascorbic acid, calcium ascorbate, erythorbic acid, sodium ascorbate, sodium erythorbate, benzoic acid, calcium sorbate, potassium sorbate, sorbic acid, citric acid, L-cysteine, lecithin, tartaric acid and tocopherols. Compositions described herein may contain preservatives, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, from about 0.1% to about 4%, from about 1% to about 7%, from about 3% to about 10%, or from about 0.1% to about 10% w/w of the composition.

In some embodiments, compositions comprise prebiotics, alone or in combination, including, but not limited to, psyllium, rice hulks, chicory root, dandelion greens, apples, bananas, artichokes, leeks, and asparagus. Compositions described herein may contain prebiotics, alone or in combination, in a concentration of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, about 35%, about 40%, about 45%, about 50%, about 55%, about 60%, about 65%, about 70%, about 75%, from about 0.1% to about 5%, from about 1% to about 10%, from about 5% to about 15%, or from about 10% to about 20%, from about 15% to about 25%, from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, from about 65% to about 75%, or from about 0.1% to about 75% w/w of the composition.

In some embodiments, compositions comprise nutritional supplements, alone or in combination, including, but not limited to, L-arginine, L-ornithine, 5-hydroxytryptophan, acetyl L-tyrosine, acetyl-L carnitine, alpha-lipoic acid, ashwagandha, bacopa, berbine, betaine, biotin, choline, creatine, curcumin, fish oil, flaxseed oil, ginger, ginseng, jiaogulan, kelp, manganese, methyl folate, N-acetyl-cysteine, nattokinase, niacin, quercetin, resveratrol, L-theanine, valerian root, vinpocetine and melatonin. Compositions described herein may contain nutritional supplements, alone or in combination, in a concentration of about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 12%, about 14%, about 16%, about 18%, about 20%, %, about 25%, about 30%, from about 0.01% to about 0.5%, from about 0.1% to about 5%, from about 1% to about 10%, from about 5% to about 15%, or from about 10% to about 20%, from about 15% to about 25%, from about 20% to about 30%, or from about 0.01% to about 30% w/w of the composition.

In some embodiments, compositions comprise over the counter (OTC) and prescription (Rx) drugs, alone or in combination, including, but not limited to salicylic acid, trans-retinoic acid, the alpha-hydroxy acids (e.g., lactic acid), benzoyl peroxide, bismuth subsalicylate, metronidazole, tetracycline, erythromycin, proton pump inhibitors, misoprostol, antibiotics, anti-fungal drugs, anti-inflammatories, or antacids. Compositions described herein may contain over the counter (OTC) and prescription (Rx) drugs, alone or in combination, in an amount of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 15%, about 20%, from about 0.1% to about 5%, from about 1% to about 10%, from about 5% to about 15%, from about 10% to about 20%, or from about 0.1% to about 20% w/w of the composition.

In some embodiments, compositions comprise food colorings, alone or in combination, including, but not limited to FD&C Blue #1, FD&C Blue #2, FD&C Green #3, FD&C Red #3, FD&C Yellow #5, FD&C Yellow #6, riboflavin, annatto, carmine, elderberry juice powder, lycopene, or turmeric. Compositions described herein may contain food colorings, alone or in combination, in an amount of about 0.001 ppm, about 0.002 ppm, about 0.003 ppm, about 0.004 ppm, about 0.005 ppm, about 0.006 ppm, about 0.007 ppm, about 0.008 ppm, about 0.009 ppm, about 0.01 ppm, about 0.02 ppm, about 0.03 ppm, about 0.04 ppm, about 0.05 ppm, about 0.06 ppm, about 0.07 ppm, about 0.08 ppm, about 0.09 ppm, about 0.1 ppm, about 0.2 ppm, about 0.3 ppm, about 0.4 ppm, about 0.5 ppm, about 0.6 ppm, about 0.7 ppm, about 0.8 ppm, about 0.9 ppm, about 1 ppm, about 2 ppm, about 3 ppm, about 4 ppm, about 5 ppm, about 6 ppm, about 7 ppm, about 8 ppm, about 9 ppm, about 10 ppm, about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, from about 0.001 ppm to about 0.05 ppm, from about 0.05 ppm to about 0.1 ppm, from about 0.1 ppm to about 0.5 ppm, from about 0.5 ppm to about 1 ppm, from about 0.5 ppm to about 5 ppm, from about 1 ppm to about 10 ppm, from about 5 ppm to about 50 ppm, from about 50 ppm to about 200 ppm, from about 100 ppm to about 500 ppm, or from about 0.001 ppm to about 500 ppm w/w of the composition.

VIII. FORMATION AND CHARACTERISTICS OF MOLECULAR HYDROGEN GENERATING AND SUSTAINING GLUCOMANNAN GELS

It has been unexpectedly found that when magnesium metal powder is combined with glucomannan powder in a powder formulation and then mixed with water, a gel is created that has some novel properties, including generating, holding, and sustaining large volumes of molecular hydrogen for an extended period of time. The resultant gels have low density and high porosity, as noted by observing the molecular hydrogen 'bubble' content and measuring the dissolved molecular hydrogen. These characteristics allow for formulating gels that are nutritious and have a desirable texture as a food as well as other applications. There are health benefits such as use as an adjunct to weight control and fasting regimens. The effect of retaining large quantities of molecular hydrogen in glucomannan gels is non-obvious since it is shown that generation of carbon dioxide in a glucomannan gel does not retain that gas in the gel nor change its density (See Rows 2-5, Table 1). Also, preparing control aqueous glucomannan gels in air (i.e., with 20% oxygen), i.e., glucomannan without magnesium metal powder in air does not retain gas bubbles of expand the aqueous glucomannan gel.

TABLE 1

Effect of $CO_2$ or $H_2$ gas generation on glucomannan gel density

| Row | Formulas in 000 Capsules/Aq. Acetic Acid | Gel mL | Head mL | Total mL | $H_2$ ppm | Final pH | Gel/g gmn | Capsules |
|---|---|---|---|---|---|---|---|---|
| | Potassium Bicarbonate Study | | | | | | | |
| 1 | 0.1 g Mg | 0.0 | 37.6 | 37.6 | 0.7 | 3.4 | 0.0 | 1 |
| 2 | 0.1 g K bicarbonate. + 2.0 g gmn | 13.4 | 0.0 | 13.4 | 0.0 | 3.3 | 6.7 | 3 |
| 3 | 0.2 g K bicarbonate. + 2.0 g gmn | 21.6 | 9.3 | 30.9 | 0.0 | 3.2 | 10.8 | 3 |
| 4 | 0.4 g K bicarbonate. + 2.0 g gmn | 11.0 | 10.3 | 21.3 | 0.0 | 3.4 | 5.5 | 4 |
| 5 | 0.8 g K bicarbonate. + 2.0 g gmn | 11.4 | 14.3 | 25.7 | 0.0 | 3.7 | 7.2 | 4 |
| | 0.1 g Magnesium Metal Powder Study | | | | | | | |
| 6 | 1.6 g gmn | 18.8 | 0.0 | 18.8 | 0.0 | 2.9 | 11.8 | 3 |
| 7 | 0.1 g Mg + 0.8 g K bicarbonate, 2.0 g gmn | 45.5 | 39.4 | 84.9 | 1.3 | 3.9 | 22.8 | 3 |
| 9 | 0.05 g Mg + 1.6 g gmn | 49.2 | 14.2 | 63.4 | 0.6 | 3.4 | 30.8 | 2 |
| 8 | 0.1 g Mg + 3.0 g gmn | 75.1 | 22.7 | 97.8 | 0.8 | 3.4 | 25.0 | 5 |
| 10 | 0.15 g Mg + 4.0 g gmn | 132.7 | 25.4 | 158.1 | 2.2 | 3.7 | 33.2 | 7 |
| | Glucomannan Reduction of Passivation | | | | | | | |
| 11 | 0.1 g Mg + 0.2 g gmn | 17.6 | 26.9 | 43.0 | 1.0 | 3.4 | 88.0 | 1 |
| 12 | 0.1 g Mg + 0.4 g gmn | 24.4 | 25.4 | 49.8 | 0.9 | 3.4 | 61.0 | 1 |
| 13 | 0.1 g Mg + 0.8 g gmn | 41.6 | 28.8 | 70.4 | 1.2 | 3.3 | 52.0 | 2 |
| 14 | 0.1 g Mg + 1.6 g gmn | 73.4 | 22.5 | 95.9 | 1.5 | 3.5 | 45.9 | 3 |
| 15 | 0.1 g Mg + 1.6 g gmn (Repeat) | 73.3 | 25.7 | 99.0 | 1.0 | 3.4 | 45.8 | 3 |

Abbreviations
$H_2$: Molecular Hydrogen
Mg: Magnesium metal powder
gmn: Konjac glucomannan
K—potassium
Gel Vol. Volume occupied by glucomannan gel
Headspace: Volume (mL) of $H_2$ gas displacing water in the headspace of the sealed 500 mL bottle.
Total Vol.: Volume occupied by the glucomannan gel and headspace volume.

As listed in Table 2 and Table 3, formulas were prepared containing 0 to 207 mg of crude magnesium metal powder (Mg), 0 to 8.0 grams of konjac root glucomannan and 0 to 7 grams of citric acid. As listed in Table 4, powders containing magnesium metal, glucomannan (gmn), and citric acid were prepared using a gravimetric method.

TABLE 2

Effect of Varying Components of Magnesium Metal Powder - Glucomannan Formulations

| Row | Formulas/100 mL DW Vary Magnesium Metal Powder | Gel Dens. g/mL | $H_2$ mL | mL $H_2$/ mg Mg | Total Gel (mL) | Bubble Gel Vol. |
|---|---|---|---|---|---|---|
| 1 | 4.0 g gmn + 5.0 g CA(Reference) | 0.994 | xxxxx | xxxx | 112.8 | 0.0 |
| 2 | 11 mg Mg + 4.0 g gmn + 5.0 g CA | 0.825 | 16.6 | 1.51 | 129.4 | 129.4 |
| 3 | 24 mg Mg + 4.0 g gmn + 5.0 g CA | 0.751 | 29.9 | 1.25 | 142.7 | 142.7 |
| 4 | 42 mg Mg + 4.0 g gmn + 5.0 g CA | 0.734 | 32.8 | 0.78 | 146.0 | 146.0 |
| 5 | 63 mg Mg + 4.0 g gmn + 5.0 g CA | 0.704 | 39.8 | 0.63 | 152.6 | 152.6 |
| 6 | 207 mg Mg + 4.0 g gmn + 5.0 g CA | 0.547 | 83.0 | 0.40 | 195.8 | 195.8 |

TABLE 2-continued

Effect of Varying Components of Magnesium Metal Powder - Glucomannan Formulations

| | Vary Citric Acid (CA) | Gel Dens. g/mL | $H_2$ mL | mL $H_2$/ g CA | Total Gel (mL) | Bubble Gel Vol. |
|---|---|---|---|---|---|---|
| 7 | 4.0 g gmn (Ref.) | 0.879 | xxxxx | xxxxx | 112.8 | 0 |
| 8 | 0.1 g Mg + 4.0 g gmn | 0.879 | 3.3 | xxxxx | 116.1 | 116.1 |
| 9 | 4.0 g gmn + 0.5 g CA (Ref.) | 0.969 | xxxxx | xxxxx | 116.1 | 0 |
| 10 | 0.1 g Mg + 4.0 g gmn + 0.5 g CA | 0.735 | 23.3 | 46.6 | 139.4 | 139.4 |
| 11 | 4.0 g gmn + 1.0 g CA (Ref.) | 0.861 | xxxxx | xxxxx | 119.5 | 0 |
| 12 | 0.1 g Mg + 4.0 g gmn + 1.0 g CA | 0.690 | 29.8 | 29.8 | 149.3 | 149.3 |
| 13 | 4.0 g gmn + 2.0 g CA (Ref.) | 0.954 | xxxxx | xxxxx | 119.5 | 0 |
| 14 | 0.1 g Mg + 4.0 g gmn + 2.0 g CA | 0.682 | 33.1 | 16.6 | 152.6 | 152.6 |
| 15 | 4.0 g gmn + 4.0 g CA (Ref.) | 0.913 | xxxxx | xxxxx | 116.1 | 0 |
| 16 | 0.1 g Mg + 4.0 g gmn + 4.0 g CA | 0.624 | 53.1 | 13.3 | 169.2 | 169.2 |
| 17 | 8.0 g gmn + 7.0 g CA (Ref.) | 0.986 | xxxxx | xxxxx | 116.1 | 0 |
| 18 | 0.1 g Mg + 8.0 g gmn + 7.0 g CA | 0.640 | 59.8 | 8.5 | 175.9 | 175.9 |

| | Vary Glucomannan (gmn) | Gel Dens. g/mL | $H_2$ mL | mL $H_2$/ g gmn | Total Gel (mL) | Bubble Gel Vol. |
|---|---|---|---|---|---|---|
| 19 | 0.5 g gmn + 5.0 g CA/DW (Ref.) | 0.916 | xxx | xxx | 112.8 | 0 |
| 20 | 0.1 g Mg + 0.5 g gmn + 5.0 g CA/DW | 0.677 | 39.8 | 79.6 | 152.6 | 59.7 |
| 21 | 1.0 g gmn + 5.0 g CA/DW (Ref.) | 0.916 | xxx | xxx | 112.8 | 0 |
| 22 | 0.1 g Mg + 1.0 g gmn + 5.0 g CA/DW | 0.710 | 33.2 | 33.2 | 146.0 | 146.0 |
| 23 | 2.0 g gmn + 5.0 g CA/DW (Ref.) | 0.854 | xxx | xxx | 122.8 | 0 |
| 24 | 0.1 g Mg + 2.0 g gmn + 5.0 g CA/DW | 0.787 | 9.9 | 5.0 | 132.7 | 132.7 |
| 25 | 3.0 g gmn + 5.0 g CA/DW (Ref.) | 0.842 | xxx | xxx | 126.0 | 0 |
| 26 | 0.1 g Mg + 3.0 g gmn + 5.0 g CA/DW | 0.778 | 10.1 | 3.4 | 136.1 | 136.1 |
| 27 | 4.0 g gmn + 5.0 g CA/DW (Ref.) | 0.895 | xxx | xxx | 119.5 | 0 |
| 28 | 0.1 g Mg + 4.0 g gmn + 5.0 g CA/DW | 0.648 | 36.5 | 9.1 | 156.0 | 156.0 |
| 29 | 6.0 g gmn + 5.0 g CA/DW (Ref.) | 0.943 | xxx | xxx | 114.5 | 0 |
| 30 | 0.1 g Mg + 6.0 g gmn + 5.0 g CA/DW | 0.762 | 28.2 | 4.7 | 142.7 | 142.7 |
| 31 | 8.0 g gmn + 5.0 g CA/DW (Ref.) | 0.985 | xxx | xxx | 112.8 | 0 |
| 32 | 0.1 g Mg + 8.0 g gmn + 5.0 g CA/DW | 0.668 | 53.1 | 6.6 | 165.9 | 165.9 |
| 33 | 8.0 g gmn + 7.0 g CA/DW (Ref.) | 0.986 | xxx | xxx | 114.5 | 0 |
| 34 | 0.1 g Mg + 8.0 g gmn + 7.0 g CA/DW | 0.640 | 61.4 | 7.7 | 175.9 | 175.9 |

Abbreviations
Mg: magnesium metal powder
gmn: glucomannan
CA: citric acid
DW: distilled water
Dens: Density;
Vol.: Volume

TABLE 3

Room Temperature (23 C.) Stability of Molecular Hydrogen ($H_2$) in Magnesium Metal Powder - Glucomannan Gels

| Study Extended from Table 2 Formulas/100 mL DW | BGV 1-Hr. | BGV 53-Hr. | BGV 108-Hr. | BGV 180-Hr. | BGV 204-Hr. | BGV 261-Hr. |
|---|---|---|---|---|---|---|
| 1 4.0 g gmn + 5.0 g CA(Reference) | xxxx | xxxx | xxxx | xxxx | xxxx | xxxx |
| 2 24 mg Mg + 4.0 g gmn + 5.0 g CA | 142.7 | 92.9 | 13.3 | xxxx | xxxx | xxxx |
| 3 42 mg Mg + 4.0 g gmn + 5.0 g CA | 146.0 | 106.2 | 19.9 | xxxx | xxxx | xxxx |
| 4 63 mg Mg + 4.0 g gmn + 5.0 g CA | 152.6 | 96.2 | 29.9 | xxxx | xxxx | xxxx |
| 5 207 mg Mg + 4.0 g gmn + 5.0 g CA | 195.8 | 192.4 | 175.9 | 179.2 | 165.9 | 132.7 |
| 6 0.1 g Mg + 4.0 g gmn | 116.1 | 126.1 | 0.0 | xxxx | xxxx | xxxx |
| 7 0.1 g Mg + 4.0 g gmn + 0.5 g CA | 139.4 | 142.7 | 0.0 | xxxx | xxxx | xxxx |
| 8 0.1 g Mg + 4.0 g gmn + 1.0 g CA | 149.3 | 149.3 | 145.6 | 132.7 | 89.6 | 68.00 |
| 9 0.1 g Mg + 4.0 g gmn + 2.0 g CA | 152.6 | 152.6 | 132.7 | 102.9 | 86.3 | 64.7 |
| 10 0.1 g Mg + 4.0 g gmn + 4.0 g CA | 169.2 | 149.3 | 132.7 | 116.1 | 109.5 | 97.9 |

| Formulas/100 mL DW | BGV 285-Hr. | BGV 321-Hr. | BGV 492-Hr. | BGV 696-Hr. | BGV 936-Hr. |
|---|---|---|---|---|---|
| 1 4.0 g gmn + 5.0 g CA(Reference) | xxxx | xxxx | xxxx | xxxx | xxxx |
| 2 24 mg Mg + 4.0 g gmn + 5.0 g CA | xxxx | xxxx | xxxx | xxxx | xxxx |
| 3 42 mg Mg + 4.0 g gmn + 5.0 g CA | xxxx | xxxx | xxxx | xxxx | xxxx |
| 4 63 mg Mg + 4.0 g gmn + 5.0 g CA | xxxx | xxxx | xxxx | xxxx | xxxx |
| 5 207 mg Mg + 4.0 g gmn + 5.0 g CA | 43.1 | xxxx | xxxx | xxxx | xxxx |
| 6 0.1 g Mg + 4.0 g gmn | xxxx | xxxx | xxxx | xxxx | xxxx |

TABLE 3-continued

Room Temperature (23 C.) Stability of Molecular Hydrogen
($H_2$) in Magnesium Metal Powder - Glucomannan Gels

| | | | | | | |
|---|---|---|---|---|---|---|
| 7 | 0.1 g Mg + 4.0 g gmn + 0.5 g CA | xxxx | xxxx | xxxx | xxxx | xxxx |
| 8 | 0.1 g Mg + 4.0 g gmn + 1.0 g CA | 0.0 | xxxx | xxxx | xxxx | xxxx |
| 9 | 0.1 g Mg + 4.0 g gmn + 2.0 g CA | 0.0 | xxxx | xxxx | xxxx | xxxx |
| 10 | 0.1 g Mg + 4.0 g gmn + 4.0 g CA | 96.2 | 96.2 | 76.3 | 56.4 | 59.7 |

Abbreviations:
BGV—Bubble Gel Volume;
gmn—glucomannan;
DW—distilled water;
CA—citric acid;
mL—milliliters;
Tot.—Total;
mg—milligrams;
Hr.—Hour;
Mg—magnesium metal powder

TABLE 4

Time Course of Molecular Hydrogen ($H_2$) Generation in Magnesium Metal
Powder (Mg) - Glucomannan $H_2$ Gels with Antioxidants and Acids

| Row | Powder Formulas mixed with 100 mL Distilled Water (DW) | Gel Wt. (g) | Dens. g/mL | 1 hour Gel Vol. (mL) | 1 hour Bubble Vol. (mL) | 1 hour Gas Vol. (mL) | 6 hour Gel Vol. (mL) | 6 hour Bubble Vol. (mL) | 6 hour Gas Vol. (mL) |
|---|---|---|---|---|---|---|---|---|---|
| 1 | 0.5 g ascorbic acid + 4 g gmn. | 101.8 | 0.852 | 119.5 | xxxxxx | xxxxxx | 119.5 | xxxxxx | xxxxxx |
| 2 | 0.1 g Mg. + 0.5 g ascorbic acid + 4 g gmn. | 102.3 | 0.752 | 136.0 | 136.0 | 16.5 | 156.0 | 156.0 | 36.5 |
| 3 | 0.5 g Na ascorbate + 0.5 g K citrate + 4 g gmn. | 102.5 | 0.870 | 119.5 | xxxxxx | xxxxxx | 116.1 | xxxxxx | xxxxxx |
| 4 | 0.1 g Mg + 0.5 g Na ascorbate + 0.5 g K citrate + 4 g gmn. | 102.2 | 0.751 | 136.0 | 136.0 | 16.5 | 152.6 | 152.6 | 36.5 |
| 5 | 0.5 g isoascorbic acid + 4 g gmn. | 102.1 | 0.867 | 119.5 | xxxxxx | xxxxxx | 112.8 | xxxxxx | xxxxxx |
| 6 | 0.1 g Mg + 0.5 g isoascorbic acid + 4 g gmn. | 101.8 | 0.731 | 139.4 | 139.4 | 19.9 | 142.7 | 142.7 | 29.9 |
| 7 | 0.5 g Na ascorbate + 4 g gmn. | 101.9 | 0.853 | 119.5 | xxxxxx | xxxxxx | 119.5 | xxxxxx | xxxxxx |
| 8 | 0.1 g Mg + 0.5 g Na ascorbate + 4 g gmn. | 102.3 | 0.856 | 119.5 | 119.5 | 0.0 | 129.4 | 129.4 | 9.9 |
| 9 | 0.5 g salicylic acid + 4 g gmn. | 101.6 | 0.862 | 119.5 | xxxxxx | xxxxxx | 117.8 | xxxxxx | xxxxxx |
| 10 | 0.1 g Mg + 0.5 g salicylic acid + 4 g gmn. | 101.9 | 0.660 | 154.3 | 154.3 | 34.8 | 152.6 | 152.6 | 34.8 |
| 11 | 0.5 g Na bisulfite + 4 g gmn. | 102.2 | 0.856 | 119.5 | xxxxxx | xxxxxx | 116.1 | xxxxxx | xxxxxx |
| 12 | 0.1 g + 0.5 g Na bisulfite + 4 g gmn. | 102.2 | 0.655 | 156.00 | 156.00 | 36.5 | 152.6 | 152.6 | 36.5 |

Abbreviations:
gmn—glucomannan;
DW—distilled water;
Mg—magnesium metal powder;
Dens.—density;
mL—milliliters;
$H_2$—molecular hydrogen;
mg—milligrams;
K—Potassium;
Na—sodium;
Vol.—volume As listed in Table 4, powders were prepared from 0 to 0.1 gram magnesium metal powder, 4 grams of glucomannan and 0.5 grams of ascorbic acid or 0.5 grams of sodium ascorbate plus 0.5 grams of potassium citrate or 0.5 grams of isoascorbic acid or 0.5 grams of salicylic acid or 0.5 grams of sodium bisulfite.

Gels were prepared, at 22-25 degrees centigrade, by taring the powders into empty 239 mL Arrowhead® water bottles, then adding 100 mL of distilled water (DW), mixing vigorously by shaking until the gel formed as indicated by perception of increased viscosity. Gels start to form 15-30 seconds after starting to mix the formulas with water. The bottles were then tightly capped.

After allowing the gels to settle, the total weights of the gel plus the weight of the bottle were gravimetrically determined. Bottles were found to weigh 10.3 grams. Thus, the weight of the gels was determined by subtracting the weight of a bottle from the total weight of the gel plus the bottle. The volume of the gels was calculated based upon the fact that the Arrowhead® bottle volume in contact with the gel is a cylinder. The measurement of the volume of a cylinder is the height of the gel, in centimeters (cm.) times the area of the base of the bottle that was determined to be 33.18 square cm. The height of the gels was measured with a 0.05 cm. graduated ruler. The density of the gels was determined by dividing the weight of the gel by its calculated volume.

Bubbly gel volumes (BGV) were determined by measuring the length (gel height) of the bubbly gel and multiplying by the 33.18 sq. cm. area.

The volume occupied by molecular hydrogen is calculated by subtracting the BGV from the control gel volume that does not contain magnesium metal powder, i.e., those control gels that do not generate molecular hydrogen as indicated as "Reference" in Table 2.

IX. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a," "an," and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The term "probiotic" means live microorganisms intended to provide health benefits when consumed, generally by improving or restoring the gut flora.

The term "prebiotic" means compounds in food that induce the growth or activity of beneficial microorganisms such as bacteria and fungi.

The term "sustainability" is defined herein as the ability to hold $H_2$ in gels or solutions over the short—term.

The term "stability" is defined as the ability to hold $H_2$ in a gel over the longer-term, i.e., longer than 24 hours.

The section headings used herein are for organizational purposes only and are not to be construed as limiting the subject matter described.

X. SPECIFIC EMBODIMENTS

Certain specific embodiments are envisioned which include:

1. A glucomannan solution comprising a concentration of glucomannan and hydrogen ($H_2$), comprising an organic acid, wherein the organic acid is selected from the list consisting of citric acid, malic acid, lactic acid, acetic acid, tartaric acid, succinic acid, phosphoric acid or any combination thereof.
2. The solution of claim 1, wherein the hydrogen ($H_2$) is present at a concentration of greater than about 100 ppb (parts per billion) hydrogen ($H_2$).
3. The solution of claim 1, wherein the volume of the glucomannan solution comprising a concentration of glucomannan and hydrogen ($H_2$) is at least 0.01%, at least 0.1%, at least 1%, at least 10%, or at least 20% greater than the volume of a corresponding glucomannan solution which does not comprise $H_2$.
4. The solution of claim 1, wherein upon exposure to standard temperature and pressure (STP) for 240 minutes, the $H_2$ concentration is at least about 70% of the initial $H_2$ concentration as measured in parts per billion (ppb).
5. The solution of claim 1, wherein the glucomannan concentration is from about 0.00001% to about 7.5%.
6. The solution of claim 1, wherein the solution is a gel.

7. The solution of claim 1, wherein the solution is a flowable liquid.
8. The solution of claim 1, wherein the $H_2$ is present in a gaseous form.
9. The solution of claim 1, wherein, upon exposure of the glucomannan solution to standard temperature and pressure (STP) for 240 minutes, the concentration of hydrogen in the glucomannan solution declines by less than 1%, less than 5%, less than 10%, less than 15%, less than 20%, less than 25%, or less than 30%. as measured in parts per billion (ppb).
10. The solution of claim 9, wherein, upon exposure of the glucomannan solution to standard temperature and pressure (STP) for 240 minutes, the concentration of hydrogen in the glucomannan solution is at least 70% of the $H_2$ concentration in the solution prior to the exposure as measured in parts per billion (ppb).
11. The solution of claim 1, further comprising a base metal.
12. The solution of claim 11, wherein the base metal is selected from the group consisting of lithium, potassium, strontium, calcium, sodium, magnesium metal powder, aluminum, zinc, chromium, manganese, iron, and any combination thereof.
13. The solution of claim 12, wherein the base metal is magnesium metal powder.
14. The solution of claim 13, wherein the magnesium metal powder is present in the glucomannan solution in an amount from about 0.00001% w/v to about 2% w/v.
15. The solution of claim 1, wherein the citric acid is present in an amount from about 0.1% w/v to about 15% w/v.
16. The solution of claim 1, wherein the malic acid is present in an amount from about 1% (w/v) to about 50% w/v.
17. The solution of claim 1, wherein the lactic acid is present in an amount from about 1% w/v to about 10% w/v.
18. The solution of claim 1, further comprising an aqueous solvent.
19. An $H_2$-generating composition comprising:
lactic acid;
glucomannan;
magnesium metal powder;
glycerin; and
an aqueous solvent.
20. The composition of claim 19, wherein the composition is a cream, gel, foam, ointment, lotion, or liquid.
21. The composition of claim 19, wherein the composition is adapted for application to the skin of a subject.
22. The composition of claim 21, wherein the composition provides a moisturizing effect to the skin of the subject.
23. A bandage comprising the composition of claim 21.

XI. EXAMPLES

The following examples are included for illustrative purposes only and are not intended to limit the scope of the invention.
Example 1: Effect on Molecular Hydrogen Content of Varying Gel Components
1. Gel Preparation
The gel formulations presented in Table 2 were prepared by first placing the glucomannan, magnesium metal and/or citric acid powders in 8-ounce plastic cups. Then, 100 mL of distilled water was added. Contents mixed by hand with a utensil, until the gel started to form—in less than two minutes.

2. Effects of Varying Magnesium Metal Powder

The results presented in Table 2 show the effects on gel parameters of varying the components of the gels. The results presented in Rows 1 to 6 show the effect varying the magnesium metal powder concentration (Mg) on Gel Density (Column 3), and molecular hydrogen ($H_2$) volume in the gel (Column 4). $H_2$ volume in the gel is calculated by subtracting the volume of the control gel, without Mg (see Row 1) from the gels containing 11 to 207 mg magnesium metal powder (Mg). For example, in Column 6, the gel volume of the control gel in Row 1 is subtracted from the test gel volume seen in Row 2; again, the gel volume of the control gel in Row 1 is subtracted from the test gel volume in Row 3, etc.

The results indicate that $H_2$ in the gel increases with the amount of Mg in the formulation (Column 4). Analysis of the results in Column 5 indicates that the $H_2$ per milligram of Mg in the formulations decreases as the concentration of Mg increases in the gel. Thus, the efficiency of $H_2$ generation or capture of $H_2$/mg of Mg in the gel decreases with increasing Mg in the formulation. Observation indicates that for the $H_2$-generating gels, bubbles were evenly dispersed from bottom to top of the gels affecting a uniform perception of bubble porosity. Bubbles are not seen in the control gel (Row 1).

3. Effects of Varying Citric Acid

The results presented in Rows 7-18 of Table 2 demonstrate the effect of varying the concentration of citric acid (CA) on gel density and molecular hydrogen ($H_2$) retention in the gel. The odd numbers are the control gels—without magnesium metal powder (Mg). The control gel density is always greater than that of the experimental gels. The $H_2$ in the gels is calculated by subtracting the odd numbers (i.e., controls) from the even number formulations, as described above. Analysis of the results indicate that $H_2$ in the gel increases with the amount of citric acid in the formulation. Analysis of the results in Column 5 indicates that the $H_2$ per milligram of citric acid in the formulation decreases as the concentration of citric acid increases in the gel. Thus, the efficiency of generation of $H_2$ in the gel decreases with increasing citric acid in the formulation.

4. Effects of Varying Glucomannan

The results presented in Rows 19-34 of Table 2 show the effect of varying the concentration of glucomannan (gmn) on gel density and $H_2$ in the gel. The odd numbers are the control gels—without Mg. Density in the control gels is always greater than that of the experimental gels. The $H_2$ in the gels in calculated by subtracting the odd numbers (controls) from the even number formulations. Analysis of the results indicate that the $H_2$ calculated to be in the gel does not always increase with an increasing amount of glucomannan in the formulation. At the lowest dose of gmn tested—as indicated in Rows 19 and 20, the Bubble Gel Volume (BGV) shown in Column 7, is markedly less than the Total Gel Volume (Column 6)—indicating a lesser ability of the lowest concentration of gmn to generate $H_2$ or to hold $H_2$ within the gel. In contrast, for higher concentrations of gmn (Rows 22, 24, 26, 28, 30, 32, 34) the Bubble Gel Volume (BGV)(Column 7) is equal to the Total Gel Volume (Column 6). The 2- and 3-gram/100 mL glucomannan gels appear to hold less $H_2$ than the 1-gram/100 mL glucomannan gel. This appears to be an artifact due to their control gels having a larger Total Gel Volume. However, as will be shown, below, gels with a higher concentration of glucomannan hold $H_2$ for a longer period of time.

5. Discussion of the Results in Table 2

Analysis of the results in Table 2 indicate that increasing the concentration of magnesium metal powder (Mg) and citric acid (CA) in the gel formulations increases the amount of molecular hydrogen ($H_2$) in the gel while decreasing the efficiency of generation and/or capture of $H_2$ in the gel. Citric acid is known to have a strong effect on removal of the passivation coat of magnesium oxide from magnesium metal (See, Uan, J-Y. et. al.(2009) J. of Hydrogen Energy 34 (15), 6137-6142). Altering the concentration of gmn in the gels presents a more complex $H_2$ response. The complex interactions between Mg, water, gmn, and citric acid regarding gel density may help to explain this anomalous behavior.

The information presented in Table 2 may be used in designing gels for different purposes. For example, one application may require fast, large volume release of $H_2$ from the gel. If so, a low concentration of gmn (e.g., 0.5-1 g/100 mL) and high concentrations of Mg (60-200 mg/100 mL) and an acidic pH would be suggested.

Cost of generating gels, particularly for a specific application, must be taken into consideration. The cost of magnesium metal powder and organic acids are inexpensive, while the cost of glucomannan per kilogram is much more expensive.

Another important consideration for food applications is taste. Taste can be modified by addition of excipients and functional agents to the magnesium metal powder-glucomannan gels.

Example 2: Effect of Exemplary Antioxidants and Acids on Molecular Hydrogen ($H_2$) Generation in Aqueous Magnesium Metal Powder (Mg)-Glucomannan (gmn) Gels Gel preparation was performed as described in Example 1. The results in Table 4 show the effect of incorporating exemplary antioxidants, salts of antioxidants or exemplary acids on: aqueous magnesium metal powder—glucomannan gel formation; gel density and the volume of $H_2$ in the gels. Evaluations at one-hour and at six-hours after gel formation are shown.

For all but one gel formula, i.e., that containing 0.5 grams of sodium ascorbate, (See Table 4, Rows 7 and 8), densities of the control gels at the 1-hour evaluation (Table 4, Rows 1, 3, 5, 9, 11) were higher, as found for those gels tested versus the control gels as shown in Table 2. Thus, at the 1-hour evaluation, 0.5 g sodium ascorbate/100 mL DW in the 0.1 magnesium metal powder-glucomannan gel does not produce an amount of $H_2$ that would lower the gel density. In contrast, at the 6-hour evaluation, it was found that 9.9 mL of $H_2$ was present in this gel. Thus, 0.5 g sodium ascorbate/100 mL DW in a magnesium metal powder—glucomannan gel slowly produces gas that is retained in the gel over the 1 to 6-hour period. This slower process of $H_2$ generation may have an advantage in situations where gel formation takes place faster than $H_2$ generation. That is, a higher percentage of $H_2$ can be sequestered in the gel.

Analyzing the 1 to 6-hour time course for $H_2$ generation in gels containing 0.5 g ascorbic acid (Table 4, Rows 1, 2); or 0.5 g sodium ascorbate plus 0.5 g of potassium citrate (Rows 3, 4); or 0.5 g isoascorbic acid (Rows 5, 6), it is observed that $H_2$ volume sustained in the gel is between 16.5 and 19.9 mL at the one hour evaluation. It rises to between 29.9 and 36.5 mL at the 6-hour evaluation. Knowledge of this slow generation and sequestration of $H_2$ in the gel is useful for trapping the maximum amount of $H_2$ in the gel. That is, the gel can be formed before appreciable $H_2$ is generated and escapes to the environment. Once the gel is formed, the additional $H_2$ generated will be trapped for an extended period.

In contrast, magnesium metal powder—glucomannan gel containing either 0.5 g salicylic acid or 0.5 g sodium bisulfate reach their maximum $H_2$ volume in the gel at 1 hour post gel formation. Like citric and other hydroxy acids, these acids affect fast generation of $H_2$ in the gels.

Example 3: Effect of Some Acids on the Generation of Molecular Hydrogen in Magnesium Metal Powder (Mg)-Glucomannan (gmn) Gels The results shown in Table 5 demonstrate the effects of some organic acids and one inorganic acid on the generation of molecular hydrogen ($H_2$) in magnesium metal powder (Mg)-glucomannan (gmn) aqueous gels. For this set of results, dry 296 mL empty water bottles were used. The empty bottles, with caps, weigh 9.6 g. The weight of the gels was determined by subtracting the weight of the empty bottle from the total weight. The area of the circumference of the bottle is 30.19 square cm (i.e., 6.2 cm. diameter). Thus, volumes of the gels were calculated by 30.19 square cm.—multiplied by the height of the gels, in cm.

TABLE 5

Effect of Acids on Generation of Molecular Hydrogen ($H_2$) in Magnesium Metal Powder (Mg) - Glucomannan (gmn) Gels

| Row | Test Formulas/100 mL DW | Dens. g/mL | Gas mL | Bubbly Gel (mL) | Tot Gel mL | pH unit |
|---|---|---|---|---|---|---|
| 1 | 4.0 g gmn + 4 g lactic acid/DW | 0.974 | 0 | 0.0 | 108.7 | 3.16 |
| 2 | 0.1 g Mg + 4.0 g gmn + 4.0 g lactic acid/DW | 0.762 | 30.2 | 138.9 | 138.9 | |
| 3 | 4.0 g gmn + 4.0 g tartaric acid/DW | 0.974 | 0 | 0.0 | 108.7 | 1.62 |
| 4 | 0.1 g Mg + 4.0 g gmn + 4.0 g tartaric acid/DW | 0.712 | 33.2 | 141.9 | 141.9 | |
| 5 | 4.0 g gmn + 4 g succinic acid/DW | 1.027 | 0 | 0.0 | 102.7 | 2.14 |
| 6 | 0.1 g Mg + 4.0 g gmn + 4.0 g succinic acid/DW | 0.744 | 39.2 | 141.9 | 141.9 | |
| 7 | 4.0 g gmn + 4.8 mL 85% phosphoric acid/DW | 1.088 | 0 | 0.0 | 96.6 | 0.98 |
| 8 | 0.1 g Mg + 4.0 g gmn + 4.8 mL 85% phosphoric acid/DW | 0.880 | 24.2 | 120.8 | 120.8 | |
| 9 | 4.0 g gmn + 4.0 g malic acid/DW | 0.997 | 0 | 0.0 | 105.7 | 1.81 |
| 10 | 0.1 g Mg + 4.0 g gmn + 40 g malic acid/DW | 0.712 | 42.2 | 147.9 | 147.9 | |
| 11 | 0.1 g Mg + 4.0 g gmn + 4.0 g malic acid/LVVWD | 0.730 | 39.6 | 144.9 | 144.9 | |
| 12 | 0.1 g Mg + 4.0 g gmn + 4.0 g malic acid/ROW | 0.751 | 34.7 | 140.4 | 140.4 | |
| 13 | 0.1 g Mg + 4.0 g gmn + 4.0 g malic acid/SW | 0.752 | 34.7 | 140.4 | 140.4 | |

Abbreviations: gmn—glucomannan; DW—distilled water; SW—soft water; ROW—Reverse Osmosis Water; LVVWD—Las Vegas City Water; Tot.—Total; $H_2$—molecular hydrogen; Mg—magnesium metal powder; g—grams; Dens.—density; mL—milliliters.

The results in Columns 3 and 4, respectively, show the effects on gel density and $H_2$ gas volume due to incubating the different acids, mixed into magnesium metal powder-glucomannan gel powders, and then mixed with water. The odd numbered formulations 1, 3, 5, 7 and 9 are controls—without Mg. The even numbered gels, as well as 11, 12 and 13 each contain 0.1 g of Mg.

The results listed in Column 3 of Table 5 show clearly that the densities of the gels generated with Mg present in the gel, have much lower densities relative to their controls—without Mg present. This lowering of the density is due to the presence of large numbers of $H_2$ bubbles and dissolved $H_2$-in the gel.

Column 4 of Table 5 lists the volume of $H_2$ gas that is present in each gel. The volumes of $H_2$ are based upon the difference in the volume of the Mg containing gels and their controls without Mg (Rows 1, 3, 5, 7 and 9). The volume of $H_2$ in the gels range from 24.2 mL for the phosphoric acid containing gel to 42.2 mL for the malic acid containing gel generated with distilled water. Although all types of water used for preparing magnesium metal powder-glucomannan gels readily generates $H_2$, use of distilled water appears to be the most effective at generating $H_2$ (See Rows 10-13).

Thus, all the acids tested affect the content of $H_2$ in the gels and expansion of the volume of gels. The difference in the amount of $H_2$ in the gels depends on the nature of the acid, the concentration thereof, and the pH of the composition. Comparing the $H_2$ in the gels shown in Table 5 with that generated by a comparable amount of citric acid, (See Table 2, Row 16) citric acid is a more potent effector of $H_2$ in the Mg-glucomannan gels.

Example 4: Room Temperature Stability of Molecular Hydrogen ($H_2$) in Magnesium Metal Powder (Mg)-glucomannan (gmn) Gels Longer term studies were carried out to determine the time course of loss of $H_2$ from magnesium metal powder-glucomannan gels. Here, we define sustainability as the ability to hold $H_2$ in gels or solutions over the short-term. We define stability as the ability to hold $H_2$ in the gels over the longer-term, i.e., longer than 24 hours.

Stability of molecular hydrogen ($H_2$) in the magnesium metal powder-glucomannan gels is estimated by measuring the extent that a particular gel will maintain its bubble gel volume (BGV)—over time.

For this Stability Study, some of the test samples shown in Table 2 were studied for up to 936 hours (39 days). Comparing the results in Rows 1-5 of Table 3, it is seen that as the concentration of Mg in the gels is increased, the longer the visible bubbles (BGV) last in the gels. Comparing the rate of drop of the BGV, it appears that the highest concentration of Mg (207 mg) is more effective at maintaining $H_2$ bubbles in the gel. That is, by 108 hours of stability testing, the gels containing respectively, 24, 42, and 63 mg of Mg have lost, respectively, 91.0, 86.4, and 80.4% of their bubble gel volume. In contrast, the gel containing 207 mg of Mg lost only 10.2% of its bubbly gel volume (BGV). The gel containing 207 mg Mg maintained 68% of its BGV up to 261 hours (10.9 days)—after gel preparation. Thus, there may be a synergistic effect of Mg in maintaining BGV in glucomannan formulations. It is possible that an interaction of Mg and/or magnesium hydroxide takes place with the $H_2$ bubble complex in the glucomannan gel. Also, an interaction of Mg particles with $H_2$ microbubbles in the gel, would tend to keep the $H_2$ bubbles from escaping from the gel.

Comparing the results in Rows 6-10 of Table 3, it is seen that as the concentration of citric acid increases, the stability of $H_2$ bubbles in the gel (BGV) increases. Thus, it has been unexpectedly found that citric acid increases the stability of $H_2$ in aqueous Mg-glucomannan formulations.

Example 5: Refrigerated Study of Molecular Hydrogen ($H_2$) Stability in Aqueous Magnesium Metal Powder-Glucomannan Gels 1. Experimental A study was carried out to determine the stability of $H_2$ in a magnesium metal powder-glucomannan gel under refrigerated conditions (1-4 deg. C.). A batch consisting of 1.1 g of crude magnesium metal powder (Mg), 44.0 g of Best Naturals® konjac glucomannan powder and 5.5 g of citric acid was prepared and mixed thoroughly. Aliquots of 9.1 g of the batch of powder were added to 5 empty 237 mL plastic bottles. Thereafter, 100 mL of distilled water was added to each bottle. The bottles were tightly capped and shaken vigorously while the gels formed. Bottles labeled #6-10 were designated for the refrigerated stability study. After the gels formed, a line was drawn on the bottle where the gel—air interface formed, thereby delineating the height of the gel. Knowing the area of the base of the bottle as 33.18 square cm, the volume of the gels was calculated, i.e., from the volume of a cylinder. Initially, the entire volume of the gels contained numerous bubbles, of diverse sizes—from top to bottom of the bottle. The volume of gel containing bubbles was designated as the Bubble Gel Volume (BGV). It was observed that the bubbles diffused up from the bottom of the gel with the passage of time. It is observed that the gels become depleted of $H_2$ bubbles—from bottom-to-top of the gel, as time passes. The change in the BGV, with time, was determined by measuring the length of the gel that still contained bubbles and multiplying times the circumference of the bottle to obtain the remaining BGV. To gain access to the gel at completion of the time course of the experiment, the top section of the plastic bottle was cut off exposing the gel for measurements of dissolved $H_2$. Dissolved $H_2$, in the gels, was measured with the Trustlex® Molecular Hydrogen ($H_2$) meter, without the guard that protects the electrode. The guard is removed since it would deny access of the Trustlex® electrode to the gel.

2. Results

The time course of results is shown in Table 6. As shown in Column 2, there is a progressive, slow reduction in BGV—with time. At Day 73, the last day of the Study, the gel retained 51.1% of the baseline BGV. $H_2$ measurements, at that time, indicated that there was 250 ppb dissolved $H_2$ in the Gel.

TABLE 6

Refrigerated (1-4 C.) Study on the Stability of Molecular Hydrogen in a Magnesium Metal Powder - Glucomannan Gel

| Day | BGV | % Change in BGV | Dissolved $H_2$ ppb |
|---|---|---|---|
| 0 | 169.3 | xxxx | NM |
| 2 | 163.9 | −3.2 | NM |
| 13 | 148.7 | −9.1 | NM |
| 29 | 148.7 | −9.1 | 432 |
| 41 | 132.7 | −21.6 | 459 |
| 50 | 119.5 | −29.4 | 400 |
| 62 | 124.5 | −26.5 | 379 |
| 73 | 86.6 | −48.9 | 250 |

Abbreviations
BGV—Bubble Gel Volume
ppb—parts per billion molecular hydrogen ($H_2$)
NM—Not measured This remarkable retention of $H_2$ in the Mg-gmn gel was unexpected. $H_2$ is the universe's smallest molecule and it is thought to be able to rapidly diffuse through most materials. A plastic container should not provide a long-term barrier to $H_2$ diffusion. Rather, there is a stabilization of both $H_2$ in bubbles and dissolved $H_2$ in the magnesium metal powder-glucomannan gel.

There are interesting applications of longer term, low temperature, storage of $H_2$ gels. For example, there are applications in the refrigerated food category. $H_2$-rich, Mg-gmn viscous solutions and gels can be formulated into various food products—including gels. Such products could be manufactured and stored, for extended periods of time, by manufacturers or consumers.

Example 6: Some Special Properties of Magnesium Metal Powder-Glucomannan Complexes 1. Molecular Hydrogen, but not Carbon Dioxide is Retained in Glucomannan Gels a. Introduction A study was carried out to compare the effects of potassium bicarbonate—which generates carbon dioxide gas ($CO_2$) in acidic solutions, and magnesium metal powder—which generates molecular hydrogen ($H_2$) in acidic solution—on glucomannan gel volume. The '000' capsules containing the ingredients were immersed in aqueous 1.25% acetic derived from vinegar in sealed bottles. This study was done: 1) to determine if the effect of $H_2$ on increasing gel volume is unique to use of a hydrogen-generating system; 2) to determine the effects on these gas producing agents on both gel volume and headspace volume in a closed system; 3) to have the closed system serve as a model for gel behavior in the upper gastrointestinal tract; 4) to determine the effect of increasing concentrations of glucomannan on gel volume expansion.

b. Experimental

Formulations, as listed in Table 1, were prepared by mixing the powder ingredients and then manually filling vegetarian "000" Vcaps® capsules obtained by Cap-M-Quik.com. Different numbers of capsules were used to accommodate the volume of each powder formulation (See Column 9 of Table 1). Diluted vinegar (1.25% acetic acid), in separate 2500 mL lots, was prepared by mixing 625 mL white vinegar (5% acetic acid) with 1875 mL of distilled water (DW). Great Value® purified water bottles were emptied and dried before use. When these bottles are filled and topped off, they hold 540 mL of liquid.

Both magnesium metal powder (Mg)-glucomannan capsules, and potassium bicarbonate-glucomannan capsules were tared before being added to the empty bottles. The weight of the empty capsules was accounted for. Thereafter, the bottles were 'topped off' with the 1.25% acetic acid solution and tightly capped. The time of starting the experiment was recorded. The contents were periodically mixed by rotating the bottles by hand. Experiments were carried out at 23 C.

$H_2$ Blue®, a methylene blue-platinum catalyst titration method, used as instructed by the manufacturer ($H_2$ Sciences.com), was employed to estimate dissolved $H_2$ in ppm. One drop of test solution is equivalent to 0.1 ppm $H_2$. For example, if it takes 5 drops of the test solution to turn six mL of a solution blue, then the solution contains 0.5 ppm $H_2$. Testing was performed in a 20 mL graduated plastic vial. The pH measurements were taken with an EXTECH® ExStik® PH100 pH meter that was periodically calibrated.

Generation of $H_2$ gas from magnesium metal powder reacting with dilute vinegar and generation of carbon dioxide ($CO_2$), from potassium bicarbonate reacting with dilute vinegar, in the sealed bottles creates a headspace. The volume of the 1.25% acetic acid liquid displaced by the gases generating the headspace in the bottles was measured as follows: At completion of the study, there was a displacement of liquid on the top of the sealed bottles, i.e., the headspace. A marker pen was then used to delineate the length and circumference of the headspace. The marker pen was also used to delineate the length and circumference of the gel in each bottle. After emptying and rinsing the bottles, leaving the caps in place, a scissors was used to 'cut out' and save the plastic section of the bottle representing the headspace plus the plastic section of the bottle previously containing the gel. The bottle cap remained in place as a base to retain liquid in the upper portion of the 'cut out' section of the bottle. A gravimetric procedure was used to determine the amount of solution in the 'cut out' section of the bottle. That is, after weighing the empty plastic piece representing the headspace plus the gel, distilled water was added to the plastic section representing the headspace unit plus the gel—until water totally filled the headspace container. Water contained in the section representing the headspace was weighed and recorded. The upper plastic section representing the headspace was then cut away leaving the section representing the gel. The same gravimetric procedure was used to determine the volume occupied by the gel.

c. Results

Table 1, Rows 1-15, displays the 15 formulations tested. The capsules were placed in the plastic bottles, topped off with 540 mL of the 1.25% acetic acid solution and capped tightly. Incubation time was 5 hours. It should be noted that the 000 capsules readily dissolve in the aqueous 1.25% acidic acid solution.

Effect of Potassium Bicarbonate

The result in Row 1 of Table 1 shows that addition of the capsule containing 0.1 g Mg, without glucomannan, does not result in gel formation—as expected. However, it generates $H_2$ gas pressure thereby creating a 37.6 mL of headspace. It also produces 0.7 ppm of molecular hydrogen ($H_2$) that is dissolved in the 1.25% acetic acid solution. Thus, in this system, $H_2$ can exist in both the headspace and be dissolved in the aqueous acidic solution.

The results in Rows 2-5 of Table 1 show formulations containing 2 grams of glucomannan (gmn) and different concentrations of potassium bicarbonate—which generates carbon dioxide ($CO_2$) in this acidic solution. Potassium bicarbonate was tested with glucomannan to determine if the resultant generation of $CO_2$ could alter gel formation and affect gel expansion. The results show that incubating the glucomannan-containing formulations with increasing doses of potassium bicarbonate, generates a head space of 0.0-14.3 mL in a dose-response manner (See Rows 2-5, Column 4). In contrast, a 1.6 g glucomannan formulation, without $CO_2$-producing potassium bicarbonate, does not produce a head space (See Row 6 of Table 1). The total volume i.e., head space plus gel volume affected by potassium bicarbonate (Rows 2-5, Column 5), is 13.4-30.9 mL. The gels alone, containing potassium bicarbonate, range from 11.0 to 21.6 mL—where gel volume does not increase with potassium bicarbonate content. Column 8 lists the efficiency of gel formation, i.e., the volume of gel produced per gram of glucomannan. The efficiency of this group ranges from 5.5 to 10.8 mL of gel per gram of glucomannan. There is a lack of a dose-response relationship in affecting gel volume per gram of glucomannan—when tested with potassium bicarbonate. The concentration of potassium bicarbonate in the gel (See Rows 2-5, Column 3 and 8) is not related to the volume of gel formation. The formulation containing 1.6 g of glucomannan (Row 6, Column 2), without potassium bicarbonate, is slightly more efficient at gel formation than the glucomannan gels that contain potassium bicarbonate. (Rows 2-5, Column 8). Therefore, potassium bicarbonate and, in turn, $CO_2$ does not expand glucomannan gels. These observations on glucomannan-potassium bicarbonate compositions in aqueous acidic environments supports the hypothesis that there is a strong interaction between $H_2$ generation from magnesium metal powder and glucomannan resulting in the expansion of glucomannan gels that is a unique property of generating $H_2$ in glucomannan solutions and gels. That is, generation of any gas in aqueous-glucomannan gels will not expand the gel volume—as found for $H_2$.

d. Effect of Magnesium Metal Powder

The results in Rows 7-15, Column 2 of Table 1 show magnesium metal powder-glucomannan (Mg-gmn) formulations, in 000 capsules. These capsules were added to 1.25% acetic acid, as a stomach acid model, as discussed above. Magnesium metal powder was combined with glucomannan, in capsules, to determine its effect on gel formation as well as to determine the generation of molecular hydrogen ($H_2$) in this aqueous acidic solution. The results in Column 4 show that glucomannan formulations containing magnesium metal powder (Mg) generate a head space of between 14.2 and 39.4 mL. The formulation that generates the 14.2 mL headspace contains the lowest concentration of Mg (0.05 g) while the formulation that generates the largest head space contains both Mg (0.1 g) and potassium bicarbonate (0.8 g). Thus, both Mg and potassium bicarbonate contribute to the head space volume. The gels produced by the Mg containing glucomannan formulations range from 17.6-132.7 mL (Column 4). Increasing both magnesium metal powder and glucomannan leads to increased gel volume. The efficiency of gel formation is inversely related to the glucomannan concentration, where the lowest concentration of gmn (0.2 g), in the presence of 0.1 g Mg, generates the most gel/gram of glucomannan. It is of interest that addition of 0.8 g potassium bicarbonate reduces the efficiency of generation of gel volume by magnesium metal powder (Row 7). This shows that the reaction of magnesium metal powder with water in the glucomannan—1.25% acetic acid solution generates an expanded gel volume larger than would be anticipated from previous results. This generation of expanded gel volume involves the sequestering of bubbly molecular hydrogen in the gel and the presence of dissolved molecular hydrogen in the gel.

e. Removal of the Passivation of Magnesium Metal Powder by Glucomannan

Comparing the results in Row 6 of Table 1 with those of Rows 11-15 of Table 1, it is seen that the increasing concentration of glucomannan increases gel volume (Column 3) in a dose—response manner. Since, as shown in Row 6, without magnesium metal powder, the highest concentration of glucomannan studied, i.e., 1.6 g, has a gel volume of 18.8 mL (See Row 6, Column 3). Comparing this volume to the 73.4 mL gel volume generated by the 1.6 g glucomannan plus 0.1 g magnesium metal powder, the effect on generation molecular hydrogen in the gel is obvious. Thus, the generation of $H_2$ by 0.1 g magnesium metal powder in the glucomannan gel has an effect of increasing gel volume by 390%. Further, comparing the results in Rows 1-15 of Table 1, it can be seen that there is a dose-response relationship in increasing gel volume by increasing the concentration of glucomannan. This effect must be due to increasing molecular hydrogen in the gel, since all but one of these formulations has much lower concentrations of glucomannan than the control displayed in Row 6 of Table 1. These results point to a direct interaction between glucomannan and magnesium metal powder in the aqueous acidic solution—in promoting the generation of molecular hydrogen in the resultant gels. This interaction is best explained by glucomannan having the ability to catalyze the removal of the magnesium oxide passivation coat from the surface of magnesium metal powder particles.

Further, results shown here and in Table 14 and FIG. 1 demonstrate that glucomannan, without citric acid, can affect the removal of the passivation coat of magnesium oxide from magnesium metal powder.

f. Discussion

Generation of molecular hydrogen ($H_2$), in an acidic solution mimicking stomach acid, takes place when glucomannan is combined with magnesium metal powder (Mg). This effect is observed by comparing the generation of 0.7 ppm $H_2$ by 0.1 g magnesium metal powder—without glucomannan (See Row 1, Table 1)—with the formulations containing 0.1 Mg with 0.2-4.0 g of glucomannan—which generates 0.8 to 1.5 ppm of dissolved molecular hydrogen (See Rows 7-15, Table 1).

There has been a failure of weight loss treatments and programs to stop the progression of the obesity epidemic. Also, there is lack of effective and safe weight loss drugs. Obesity is only the 'tip of the iceberg'. A newly uncovered inflammatory component of obesity is now known to lead to serious diseases, including Type 2 diabetes, cardiovascular disease, cancer, Alzheimer's disease, fatty liver disease and several autoimmune diseases. Thus, there is a need for a safe and effective product that treats both the cause of obesity and the inflammatory component that affects the associated diseases—listed above.

Molecular hydrogen ($H_2$)-generating magnesium metal powder (Mg)-glucomannan formulations delivered to the stomach by capsule, tablet or other pharmaceutical dosage forms, can create satiety by generating a feeling of fullness for 4-8 hours, while reducing obesity associated inflammation due to the generation and sustained release of anti-inflammatory molecular hydrogen.

Example 7: Effect of Ingestion of Magnesium Metal Powder ($M_2$)-Glucomannan (gmn) Capsules on Satiety A subject experienced hunger sometime between early lunch (around 9:30 AM) and dinner (around 5:30 PM). He would snack on 'junk food' before dinner and found he was gaining unwanted weight.

It was suggested that when feeling hungry that he consumed a 7% magnesium metal powder-93% glucomannan powder mixture, encased in capsules where each capsule contained 0.4 grams powder per capsule.

In the first trial, he started feeling hungry at about 2:30 PM. He took one 7% Mg-93% gmn capsule with an 8 oz. glass of water and was able to avoid snacking until 4:40 PM, upon which he 'broke down' and snacked.

In the second trial, he again started feeling hungry about 2:00 PM. He took three of the 7% Mg-93% gmn capsules with a 12 oz. glass of water. He was able to avoid snacking and ate his dinner on time. He did not experience any adverse events from taking the 7% Mg-93% gmn capsules.

In the third trial, he again started feeling hungry about 2:00 PM. He took 6 of the 7% Mg-93% gmn capsules with about 15 oz. of water. He experienced a feeling of fullness within five minutes. He was able to avoid snacking. He could finish the main course of his dinner, but refused desert, which he normally ate. The only side effect was a feeling of fullness. It did not alter his sleeping or bowel movement patterns.

Example 8: Development of a Hydrogen-Rich, Low Calorie Lemon Gel

There is a need for a snack or desert that will substitute for high calorie foods, provide a feeling of fullness—thereby supporting weight control and fasting regimens.

sweetness, tartness, texture, color and lemon flavor. The initial formulation and taste testing studies which resulted in the elimination of some ingredients are not displayed here.

Table 7 displays the results of the last three sequential studies involved in the process of development of the gel.

TABLE 7

Development of a Low Calorie, Hydrogen - Rich Lemon Gel Based Upon Magnesium Metal Powder and Glucomannan

| # | Formulas/100 mL Distilled Water (DW) | Sweetness | Tartness | Texture | Comments | 1-Hr Vol. Inc. (mL) |
|---|---|---|---|---|---|---|
| | Study 6218 | | | | | |
| 1 | 8 mg Mg + 4.0 gmn + 0.8 g Stevia + 0.5 g LF + 0.3 g Na ascorbate | 2 | 5 | 10 | No LF, not sweet | −5.6 |
| 2 | 16 mg Mg + 4.0 gmn + 0.8 g Stevia + 0.5 g LF + 0.3 g Na ascorbate | 2 | 5 | 10 | No LF, not sweet | 5.6 |
| 3 | 47 mg Mg + 4.0 gmn + 0.9 g Stevia + 0.5 g LF + 0.3 g Na ascorbate | 3 | 5 | 10 | Better than 1 & 2 | 11.3 |
| 4 | 79 mg Mg + 4.0 gmn + 0.7 g Stevia + 0.5 g LF + 0.3 g Na ascorbate | 3 | 5 | 10 | Same as 3 | 14.4 |
| 5 | 40 mg Mg + 4.0 gmn + 0.9 g Stevia + 0.7 g LF + 0.3 g Na ascorbate | 3 | 5 | 10 | Little LF, not sweet | 11.3 |
| 6 | 39 mg Mg + 4.0 gmn + 0.8 g Stevia + 1.0 g LF + 0.3 g Na ascorbate | 3 | 4 | 10 | Little LF, starchy | 14.4 |
| 7 | 38 mg Mg + 4.0 gmn + 0.8 g Stevia + 1.0 g LF + 0.2 g isoascorbic acid | 2 | 5 | 10 | Bitter, not sweet | 17.0 |
| 8 | 45 mg Mg + 4.0 gmn + 0.8 g Stevia + 1.0 g LF + 0.4 g isoascorbic acid | 1 | 7 | 10 | Bitter, not sweet | 22.6 |
| 9 | 41 mg Mg + 4.0 gmn + 0.8 g Stevia + 1.0 g LF + 0.2 g malic acid | 1 | 7 | 10 | Bitter, not sweet | 11.3 |
| 10 | 43 mg Mg + 4.0 gmn + 0.8 g Stevia + 1.0 g LF + 0.4 g malic acid | 4 | 7 | 10 | Bitter, not sweet | 19.8 |
| 11 | 44 mg Mg + 4.0 gmn + 1.0 g Stevia + 1.0 g LF + 0.2 g ascorbic acid | 3 | 4 | 10 | No LF, not sweet | 25.5 |
| 12 | 35 mg Mg + 4.0 gmn + 0.8 g Stevia + 1.0 g LF + 0.4 g ascorbic acid | 2 | 7 | 10 | No LF, not sweet | 19.8 |
| | Study 6318 | | | | | |
| 1 | 53 mg Mg + 4.0 g gmn + 1.5 g Stevia + 2.0 g LF + 0.4 g Na ascorbate | 7 | 7 | 10 | slight after-taste | 11.3 |
| 2 | 50 mg Mg + 4.0 g gmn + 1.5 g Stevia + 3.0 g LF + 0.4 g Na ascorbate | 5 | 5 | 10 | off-taste | 8.5 |
| 3 | 54 mg Mg + 4.0 g gmn + 3.0 g Stevia + 2.0 g LF + 0.4 g Na ascorbate | 7 | 7 | 10 | creamy, off-taste | 8.5 |
| 4 | 51 mg Mg + 4.0 g gmn + 3.0 g Stevia + 3.0 g LF + 0.4 g Na ascorbate | 8 | 8 | 10 | Best of Group | 5.7 |
| 5 | 51 mg Mg + 4.0 g gmn + 4.0 g Stevia + 4.0 g LF + 0.4 g Na ascorbate | xxxx | xxxx | xxxx | off-taste | 14.2 |
| | Study 6418** | | | | | |
| 1 | 31 mg Mg*. + 4.0 g gmn + 0.4 g NaAscorbate + 3.0 g stevia + 3.0 g LF | 10 | 7 | 10 | sight off-taste | 19.8 |
| 2 | 32 mg Mg*. + 4.0 g gmn + 0.4 g NaAscorbate + 3.1 g stevia + 3.1 g LF | 10 | 7 | 10 | slight off-flavor | 17.0 |
| 3 | 33 mg Mg*. + 4.0 g gmn + 0.4 g NaAscorbate + 3.2 g stevia + 3.2 g LF | 10 | 9 | 10 | Best Taste | 22.6 |

Abbreviations
gmn—glucomannan
LF—Lemon Flavor
No LF—no lemon flavor perceived by the taste test
Mg*—63 micron (230 Mesh) Lot of magnesium metal powder
**0.72 mg FD&C Yellow # 5 is in the 100 mL DW added for color.

A delicious tasting, 5 calorie lemon gel, retaining molecular hydrogen ($H_2$) and expanding in volume, thereby giving a feeling of fullness, was the objective of a product development program. Development took place by a process of variation of the levels of magnesium metal powder (Mg) and glucomannan (gmn), along with testing D-L malic acid, ascorbic acid, iso-ascorbic acid and the natural sweetener-stevia, a natural lemon flavor powder (BioFinest®) and FDC Yellow #6. Several low-calorie versions of gels were prepared and tested for volume expansion of the gel due to $H_2$, 1. Study 6218

Rows 1-12 of Study 6218 in Table 7, display twelve powder formulations with variation, of Mg, stevia, lemon flavor (LF), Na ascorbate, isoascorbic acid, malic acid and ascorbic acid. After addition of 100 mL distilled water and mixing, the solutions start to gel within 30-60 seconds. Within an hour, an experienced dietitian evaluated the resulting gels, on a scale of 1 (bad) to 10 (excellent) for sweetness, tartness and texture.

All gels had an outstanding texture, being light and uniquely fluffy. However, none of the gels had an acceptable taste (Columns 3 and 4). There was an insufficient amount of sweetness. The gels shown in Rows 2-12 expanded in volume by 5.6-25.5 mL after standing for at least an hour. The volume of the gel displayed in Row 1, with the lowest concentration of Mg, contracted by 5.6 mL—probably due to an interaction of Mg with glucomannan. Otherwise, there is a dose-response relationship for increase in gel volume with increasing Mg content. (See Rows 1-4 of Study 6218). Addition of more Mg generates more $H_2$-thereby affecting gel expansion and 'fluffiness'. Although isoascorbic acid, ascorbic acid, and malic acid in the lemon-flavored formulation led to significant volume expansion of the gels (Rows 7-10), they imparted a bitter, "off" taste at the concentrations tested.

2. Study 6318

Analysis of the results of Study 6218 led to the design and testing of the formulations listed under Study 6318 of Table 7. As a result of Study 6218, it was determined that Na ascorbate did not impart a bitter taste as found with testing the organic acids. An additional amount of stevia was added to enhance sweetness. Also, an additional amount of lemon-flavored powder (LF) was added to enhance the lemon flavor. Magnesium metal powder was tested at 50-54 mg/100 mL.

It was found that none of the 5 gels listed in Rows 1-5 of Study 6318 scored above an 8 for sweetness and tartness. The texture was excellent. The gel shown in Row 4 was judged to be best. All 5 gels increased in gel volume upon standing for one hour or more.

3. Study 6418

It was determined that based upon the results for Gel #4 of Study 6318 that slightly more sweetness and lemon flavor were needed. A lower dose of Mg was used. This magnesium metal powder was the 63-micron (230 Mesh) fraction of the Lot of magnesium metal powder used in previous studies. It is designated in Table 7 as Mg*. Of the three gel formulas displayed in Rows 1-3 of Study 6418, #3 was judged qualitatively to be best. This gel had the highest level of both stevia and the lemon flavor. All three gels increased in volume upon standing.

The results demonstrate that it is possible to create a delicious tasting, textured, hydrogen-rich lemon gel based upon glucomannan and magnesium metal powder. This hydrogen rich lemon gel should be helpful to weight management and intermittent fasting regimens.

Lemon and chocolate hydrogen-rich gels have been prepared and have been used to control food cravings in-between meals.

Example 9: Transforming Marketed Lemon-Flavored Powders, for Drinks, into Delicious Molecular Hydrogen-Generating and Sustaining Gels 1. Introduction It has been found that magnesium metal powder (Mg)-glucomannan (gmn) formulations can be used to transform marketed drinks into gels with a desirable taste and texture. Of particular interest here, is turning marketed low-calorie flavored powders designed to make beverages into low calorie hydrogen-rich gels that can be used to augment weight loss and fasting programs. That is, drink making powders formulated with the addition of Mg and gmn-transforms aqueous drinks into hydrogen-rich gels, with an expanded volume, that are perceived as 'filling' and having a desirable and unique 'fluffy' texture.

TABLE 8

Molecular Hydrogen Gels Containing Marketed Lemon Flavored Drink Powders

| # | Formula/100 mL Distilled Water (DW) | Taste | Comments | 1-Hr Vol. Inc. (mL) | 4-Hr Vol. Inc. (mL) |
|---|---|---|---|---|---|
| | Study 6518 | | | | |
| 1 | 24 mg Mg* + 4.0 g gmn + 1.7 g Crystal Light | 9 | Acceptable, Good | 8.5 | 11.2 |
| 2 | 22 mg Mg* + 4.0 g gmn + 2.5 g Crystal Light | 10 | Acceptable, better than 1 | 11.4 | 5.7 |
| 3 | 41 mg Mg* + 4.0 g gmn + 1.7 g Crystal Light | 9 | Acceptable | 14.2 | 17.0 |
| 4 | 40 mg Mg* + 4.0 g gmn + 2.5 g Crystal Light | 10 | Best Gel, best flavor | 11.3 | 14.2 |
| 5 | 20 mg Mg* + 4.0 g gmn + 0.8 g Crystal Light | 7 | Not acceptable, weak flavor | 2.8 | 16.9 |
| 6 | 42 mg Mg* + 4.0 g gmn + 0.8 g Crystal Light | 8 | OK, but weak flavor, color | 5.7 | 19.6 |
| | Study 6618 | | | | |
| 1 | 43 mg Mg* + 4.0 g gmn + 2.5 g Crystal Light (2012) | 10 | Excellent Tartness | 22.6 | 31.1 |
| 2 | 44 mg Mg* + 4.0 g gmn + 2.5 g Crystal Light (2020) | 10 | Very Good Tartness | 22.6 | 31.1 |
| 3 | 44 mg Mg* + 4.0 g gmn + 2.5 g Wyler's Light Lemonade | 10 | Very Good Tartness | 22.6 | 28.3 |
| 4 | 42 mg Mg* + 4.0 g gmn + 2.5 g Great Value Lemonade | 9 | Tartness not as good | 20.0 | 31.1 |
| 5 | 4.0 g gmn + 2.5 g Crystal Light (2020) | 10 | Excellent Tartness | 0.0 | 0.0 |
| | Study 61218 | | | | |
| 1 | 40 mg Mg* + 4 g gmn + 2.5 g + True Lemon ® | 8 | Needs more lemon taste | 11.4 | 11.4 |

Abbreviations
Mg* 63 micron(230 Mesh) Lot of magnesium metal powder
gmn glucomannan
Vol Volume
Taste rated 1—awful; 10—Excellent 2. Experimental The results presented in Table 8 outline the development and testing of molecular hydrogen ($H_2$)-rich lemon gels produced from marketed lemon-flavored drink powders. The gels were developed by addition of glucomannan and Mg to the lemon-flavored powder. 100 mL of water was then added to the 4.8-6.6 g of powders and mixed for less than 2-minutes—until a 'fluffy' gel formed. For these studies, 63-micron (230 Mesh) magnesium metal powder (Mg*.) was used. Gels were evaluated for organoleptic properties, i.e., sweetness, tartness and texture. These organoleptic properties were grouped under 'Taste' in Column 3 of Table 8. All gels containing Mg-gmn had unique desirable, light, 'fluffy' texture. They were also evaluated for their potential to expand after standing for periods of one-hour and four-hours. Volume increase measurements were made as described previously.

3. Results

The results presented in Rows 1-6 of Table 8 of Study 6518 show the effect of varying concentrations of Mg* and/or gmn on the taste and volume change of various doses of Crystal Light® Natural Lemonade. The gel formed from the ingredients displayed in Row #4, i.e., 40 mg Mg*+4.0 g gmn+2.5 g Crystal Light® Natural Lemonade was judged to be the best tasting gel. It contained 3.1 times the recommended dose for making Crystal Light® Natural Lemonade drinks. All formulations containing Mg*-gmn, affected an expansion of gel volume—upon standing. This phenomenon indicated that the gels retained much of the $H_2$ that was generated. Much of the $H_2$ was retained as gas bubbles. Mg* continued to react with water, in the gel, and generated $H_2$ over the 5-hour time frame studied (Compare Columns 5 & 6 of Table 8). This extended reactivity of Mg* with water was indicative of glucomannan's ability to affect the removal of the passivation coat of magnesium oxide from Mg*. As noted previously, the expansion of the gels provided for a highly desirable 'fluffy' texture.

The results in Rows 1-5 of Table 8 of Study 6618 showed the effects of addition 42-44 mg Mg* and 4.0 g of gmn powders to the various lemon-flavored marketed brands and mixing with 100 mL of distilled water (DW). The organoleptic properties and time course of volume expansion of the lemon gels was determined. Here, volume expansion was measured relative to that of the 4 g gmn+2.5 g Crystal Light® control gel (See Row #5, Study 6618). The organoleptic properties of all gels, except #4, met with approval by the dietitian. All gels containing 42-44 mg of Mg* showed marked expansion of the gels—relative to the control gel (in Row #5). Gels 1-4 showed expansion between 1- and 4-hours after preparation. The control gel (Row #5), without Mg*, did not expand after preparation. Thus, this study confirms the need for the generation of $H_2$ to expand the gels.

Example 10: Time Course of Loss of Dissolved Molecular Hydrogen ($H_2$) from a Mg*-gmn Gel The results presented in Table 9 show the time course of change in dissolved $H_2$ when left to stand in an open container at 23 C. Measurements were taken with the $H_2$ Trustlex® meter. This Gel is generated from 40 mg Mg*+4.0 g gmn+2.5 g Crystal Light® powders mixed with 100 mL of distilled water. A 5-hour time delay took place before measurements were taken. The results show that at 5-hours post gel production (zero time of measurement), 709 ppb $H_2$ remains in the gel. Over the course of the next 535 minutes (about 9 hours), the $H_2$ drops to 410 ppb, or retains 57.8% its $H_2$. Thus, in an open container, Mg-gmn gels retain dissolved $H_2$ for extended periods of time. These results support the presence of a strong interaction of the Mg*-gmn containing gel with $H_2$.

TABLE 9

Time Course of Loss of Dissolved Molecular Hydrogen ($H_2$) from a Magnesium Metal Powder (Mg*) - Glucomannan Gel in an 'Open Cup' Study**

| Minutes | ppb $H_2$ | % $H_2$ Remaining |
|---|---|---|
| 0 | 709 | xxxx |
| 10 | 712 | 100.0 |
| 15 | 690 | 97.3 |
| 25 | 599 | 84.5 |
| 85 | 454 | 64.0 |
| 160 | 455 | 64.2 |
| 195 | 444 | 62.6 |
| 300 | 435 | 61.4 |
| 360 | 436 | 61.5 |
| 420 | 431 | 60.7 |
| 535 | 410 | 57.8 |

Abbreviations
Mg* 63 micron(230 Mesh) Lot of magnesium metal powder
ppb parts per billion molecular hydrogen
**Started 5-Hours after Gel formation.
gmn glucomannan Example 11: Production and Analysis of Molecular Hydrogen ($H_2$) Rich Gels of Different Flavors 1. Introduction This Example illustrates the utility and flexibility of the embodiments described herein: The magnesium metal powder (Mg)-glucomannan (gmn) formulations are effective at transforming powders designed to produce beverages into low or no calorie hydrogen-rich, expansive gels that can be used for diet deserts and snacks.

2. Experimental

Each of 10 different Crystal Light® flavors, 2.5 g/serving, were individually mixed with 40 mg Mg* and 4.0 g of glucomannan to create 10 different powder formulations. To initiate gel formation, 100 mL of distilled water was added to an 8 oz. plastic cup containing each formulation and mixed for 60-90 seconds to complete gel formation. After one hour, the gel height was measured and the gel volume calculated, as described above. The gel volume increase, above the control without Mg*, was determined by subtracting the control gel volume from the experimental gel volume. The gels were evaluated for sweetness, texture, tartness, and acceptance by an experienced dietitian.

3. Results

In Column 3 of Table 10 are shown the volume increases due to incubation of the test gels for one-hour. Gel expansion was measured—relative to a control gel containing 4.0 g of gmn+2.5 g of Crystal Light® in 100 mL of distilled water. All test gel volumes increased by 14.2-25.5%. i.e., by 14.2-25.5 mL. These values reflect molecular hydrogen ($H_2$) being entrapped in the gel as both dissolved molecular hydrogen and $H_2$ bubbles. The variability of the increase in volumes for the different gels is due to differences in pH and the concentrations of components of the assorted flavors.

TABLE 10

Preparation of Hydrogen-Rich Gels using Magnesium Metal Powder (Mg*) Plus Glucomannan (gmn) Plus Crystal Light ® Flavors - added to 100 mL Distilled Water (DW)

| # | Formulas Containing 40 mg Mg* + 4.0 g gmn Mixed with 100 mL of Distilled Water | Gel ** Inc. (mL) | Sweet | Texture | Tartness | Accept |
|---|---|---|---|---|---|---|
| 1 | 2.5 g CL - Peach Mango Green Tea<br>Comment: Good | 17.0 | OK | Good | NI | YES |
| 2 | 2.5 g CL - Lemonade<br>Comment: Good | 19.8 | OK | NI | 0K | YES |
| 3 | 2.5 g CL - Peach Iced Tea (Black Tea)<br>Comment: Good | 17.0 | OK | NI | 0K | YES |
| 4 | 2.5 g CL - Grape with Caffeine<br>Comment: Good | 25.5 | OK | NI | NI | YES |

TABLE 10-continued

Preparation of Hydrogen-Rich Gels using Magnesium Metal Powder (Mg*) Plus Glucomannan (gmn) Plus Crystal Light ® Flavors - added to 100 mL Distilled Water (DW)

| # | Formulas Containing 40 mg Mg* + 4.0 g gmn Mixed with 100 mL of Distilled Water | Gel ** Inc. (mL) | Sweet | Texture | Tartness | Accept |
|---|---|---|---|---|---|---|
| 5 | 2.5 g CL - Wild Strawberry with Caffeine<br>Comment: Good | 25.5 | OK | NI | OK | YES |
| 6 | 2.5 g CL - Classic Orange<br>Comment: Good | 22.6 | NS | NI | OK | YES |
| 7 | 2.5 g CL - Fruit Punch<br>Comment: Too dense | 14.2 | OK | NI | NI | NO |
| 8 | 4 g gmn + 2.5 g CL - Pink Lemonade<br>Comment: Good | 19.8 | OK | OK | OK | YES |
| 9 | 2.5 g CL - Lemon Iced Tea<br>Comment: Off Color | 19.8 | TS | NI | NI | NO |
| 10 | 2.5 g CL - Raspberry Lemonade<br>Comment: Too dense | 25.5 | NS | NI | NI | NO |

Abbreviations
CL Crystal Light ®
Mg*—230 Mesh Lot of magnesium metal powder.
gmn glucomannan
** Gel volume increase - relative to the control 4.0 g gmn + 2.5 g CL/100 mL DW Gel
Evaluations
TS Too Sweet, reduce the sweetener
NS Needs sweetness - add
OK Excellent sweetness or tartness
NI Needs improvement in sweetness or tartness Reviewing the results in Columns 4-7, it is observed that eight of ten of the gels were judged to be acceptable—meaning they were delicious and had the desired 'fluffy' texture. Means of improving the organoleptic properties of those gels that were 'not acceptable' was readily identified and delineated in Column 4-7 of Table 10.

4. Discussion

These results attest to the flexibility of the embodiments described herein in creating good tasting gel products that are healthful to the consumer for both weight control as well as preventing and treating obesity associated-inflammation.

Essentially, any food or drink product that contains water, or is intended to contain water, can be formulated with the magnesium metal powder-glucomannan biotechnology—to generate and release molecular hydrogen and expand the gel volume.

Additional ingredients can be added either before or after forming the magnesium metal powder-glucomannan gels. Health-promoting ingredients are of most—but not exclusive interest.

Example 12: Chocolate Smoothie

A chocolate smoothie 'control' was prepared with the following ingredients:
  300 mL of Great Value® (Walmart) fat-free milk;
  5.1 grams of Hershey® Coca Natural Unsweetened;
  3.0 grams of Sweet Leaf® stevia with inulin, a prebiotic;
  Calorie content—about 100 calories.

Preparation, at 15 C, took place in a 600 mL Magic Bullet® container by adding the ingredients to the 600 mL container and mixing at high speed for 30 seconds. Then, the mixture was allowed to settle for 5 minutes. It was observed that a non-bubbly liquid-bubbly liquid phase separation takes place at 5 minutes. Therefore, the solution was mixed each time before viscosity measurements took place.

Viscosity measurements were made using an Elcometer® Shell 6 231005047 viscosity cup. The measurement consists of the time needed for the solution to completely flow through the cup. Increased viscosity results in a slower flow rate. The time needed for the above solution to pass through the viscosity cup was 24.1 seconds (N=5).

After viscosity measurements were taken, the above formulation was modified by addition of:
  3.0 grams of glucomannan;
  0.11 grams of crude magnesium metal powder;
  1.0 gram of sodium ascorbate; and
  1.1 gram of potassium citrate.

Preparation, at 20 C, took place in a 600 mL Magic Bullet® container by adding the ingredients to the 600 mL container and mixing at high speed for 30 seconds. Then, the mixture was allowed to settle for 5 minutes. It was observed that no phase separation took place. However, the solution was mixed each time before viscosity measurements took place.

Viscosity measurements took place over a 30-minute time frame. The average time for the formulation to clear the viscosity cup was 49.2 seconds (N=10). Thus, addition of the Mg-gmn formulation more than doubled the viscosity of the original formulation. During the viscosity measurements, it was observed that the time for the formulation to pass through the cup increased after each viscosity measurement indicating that the viscosity increased with time. Therefore, the modified formulation should be allowed to settle for 30 minutes, or more, before consumption.

Approximately one hour after preparation, the hydrogen content and pH of the modified formulation was measured. The molecular hydrogen Cmeasurement with the Trustlex® $H_2$ Meter demonstrated that 168 ppb $H_2$ was still present in the formulation at a pH of 7.10. Expert taste testers agreed that the modified formulation tasted very good and has a nice texture.

The formulation was frozen in a freezer overnight. After microwaving the formulation for 70 seconds, it was consumed. The taste and texture were considered acceptable.

For practical purposes, the Mg-gmn hydrogen formulations can be added to the food ingredients and mixed. The mixture can be consumed immediately. Hydrogen will be generated for an extended period in the 'gut' from the Mg in the mixture.

It should be noted that the Mg-gmn formulations will generate $H_2$ in several types of drinks. These drinks include soft drinks, fruit juices, milk and milk substitutes, smoothies, alcoholic beverages, soups and several types of water.

Example 13: Blueberry Protein Breakfast Smoothie

A sweetened blueberry and whey protein breakfast 'control' smoothie was prepared with the following ingredients:
- 300 mL reverse osmosis water;
- 3 grams of stevia (PJURE®);
- 42.5 grams of frozen blueberries (Great Value® Whole Blueberries);
- 21 grams of EAS® 100% Whey Protein.
- About 100 calories.

Preparation, at 23 C, took place in a 600 mL Magic Bullet® container by adding the ingredients to the 600 mL container and mixing at high speed for 30 seconds. Then, the mixture was allowed to settle for 5 minutes. The volume was transferred to a 600 mL graduated beaker and estimated to be 525 mL. Then, 100 mL of the formulation was removed, and 425 mL of the formulation was returned to the 600 mL Magic Bullet® for additional mixing with Mg-gmn.

Two grams of a formulation containing 4.65% magnesium metal powder, 2.33% glucomannan, 2.33% maltodextrin, 23.3% isoascorbic acid and 46.5% potassium citrate was added to the 600 mL Magic bullet container holding the 425 mL of formulation. Mixing took place for 30 seconds, followed by a 5-minute period of settling and allowing Mg to react with water in the Magic Bullet® container. The volume was then transferred to a 600 mL graduated beaker and measured to be 525 mL. Thus, there was a 100 mL, or 23.5% gain in volume after addition of 2 grams of the formulation containing Mg, gmn and excipients. A large quantity of gas bubbles was seen to be dispersed throughout the thixotropic formulation. Thus, as much as 98 mL molecular hydrogen ($H_2$) is present in the bubbly phase of the gel.

To test for release of $H_2$ from the bubble phase of the formulation and/or for latent generation of $H_2$ in the gel, the presence of available $H_2$ in the formulation was tested using the Trustlex® $H_2$ Meter. 50 mL of the final formulation was placed in an 80 mL plastic cup. Measurements of $H_2$ were periodically taken while immersing the $H_2$ meter in the formulation (23 C) for approximately 5 hours. The results are as follows: from 0 to 10 minutes, there was zero $H_2$ detected by the Meter; after 20 minutes, $H_2$ rose to 21 ppb; after one hour, $H_2$ level increased to 234 ppb; at 2.5 hours $H_2$ level was 441 ppb; by 3 hours $H_2$ level was 920 ppb; at about 4.25 hours $H_2$ level was 1031 ppb; and by 5 hours $H_2$ level had decreased to 1017 ppb.

Thus, this breakfast smoothie containing magnesium metal powder, glucomannan, and catalytic excipients provides an extended generation and release of molecular hydrogen. When ingested, the consumer will be provided with a continued release of $H_2$, in the gastrointestinal tract, for five or more hours.

Example 14: Lemon Flavored Vegetarian Protein Powdered Drink

A lemon flavored organic vegetarian citrus 'control' drink was prepared with the following ingredients:
- 300 mL of reverse osmosis water;
- 10.0 grams Nutra® protein powder blend Greens;
- 1.5 grams of BioFest® Lemon Powder
- Calorie content is about 20 calories.

Preparation, at 15 C, took place in a 600 mL Magic Bullet® container by adding the ingredients to the 600 mL container and mixing at high speed for 30 seconds. Then, the mixture was allowed to settle for 5 minutes. The formulation was mixed each time before viscosity measurements took place.

Viscosity measurements were made using an Elcometer® Shell 6 231005047 viscosity cup. The measurement consists of recording the time needed for the solution to completely flow through the cup. The average time needed for the above solution to pass through the viscosity cup was 4.0 seconds (N=5).

After viscosity measurements were taken, the above formulation was modified by addition of:
- 2.0 grams of glucomannan;
- 0.204 grams of magnesium metal powder;
- 4.1 grams of citric acid; and
- 4.5 grams of maltodextrin.

Preparation, at 20 C, took place in a 600 mL Magic Bullet® container by adding the ingredients to the 600 mL container and mixing at high speed for 30 seconds. Then, the mixture was allowed to settle for 5 minutes. It was observed that no phase separation took place. However, the solution was mixed each time before viscosity measurements took place.

Viscosity measurements took place over a 30 minute period. The average time for the formulation to clear the viscosity cup was 18.3 seconds (N=5). Thus, addition of the Mg-gmn formulation increased the viscosity of the original formulation by more than a factor of four. However, this modification resulted in a flowable liquid and not a gel. Taste testing indicated that this vegetarian formulation had a strong but pleasant texture and citrus taste.

Example 15: $H_2$-Rich, Thickened Tomato Soup

Soup is an appropriate vehicle for delivering $H_2$ systemically. For soups with a pH below 7, there is no need to add an $H_2$-generating acid or antioxidant. Otherwise, some combination of isoascorbic acid and sodium or potassium citrate could be added to facilitate the reaction of Mg with water.

Briefly, 100 mL of commercially available tomato soup was microwaved to provide a temperature of 92 C for the soup. Then, 52 mg of Mg* (63-micron particle size) was added to the soup and stirred for 15 seconds. Next, 1 g of glucomannan was added and stirred for 60 seconds—thickening the soup into a rich texture. The soup mixture was allowed to cool to 55 C. The Trustlex® $H_2$ Meter indicated that the soup contained 907 ppm $H_2$. The pH was 4.38. The soup was then consumed and found to be palatably acceptable.

Example 16: Scale-up for Production and Manufacturing

1. Introduction

All of the above examples have described the preparation and testing of unit doses of powdered formulations containing magnesium metal powder and glucomannan plus other beneficial ingredients that add flavor, sweetness and other desirable attributes. For 'in use' testing by a large number of consumers, as well as for commercial manufacturing, it is necessary to prepare much larger batches that can be packaged in unit dose packets or in large, e.g., 100-10,000 g containers—where unit doses can be dispensed, for example, with scoops.

2. Experimental

An excellent tasting low-calorie lemon flavored powder, proven to gel and sustain molecular hydrogen, when mixed with water, was developed. Thus, it was ready for an 'in use' test. A batch containing 90-unit doses was determined to be needed. The weight of a unit dose was found to be 5.835 grams. A 3% w/w overage was built into the batch. Konjac glucomannan was from Best Naturals®; malic acid, maltodextrin, aspartame were from Bulk Supplements; anhydrous magnesium sulfate was from Sigma-Aldrich; 230 Mesh magnesium metal powder (Mg*) was prepared from a batch of crude magnesium metal powder (from China); mixed tocopherols, 45%, were from Profood Products Outlet; FD & C Yellow #5 Dye was from Flavors and Colors.com. A 2L VH-2 dry powder blending, and mixing machine was obtained from RumeiShopping (China). The ingredients of the formulation were placed in the VH-2 mixer and mixed at a setting of 250 (i.e., 15 rotations per minute) for 30-minutes before being packaged in a sterile plastic container.

3. Results

The formula, containing the grams of each ingredient that was prepared and each ingredient's functionality are shown in Table 11.

TABLE 11

Scale - up of a Powder Mixture for Making a Molecular Hydrogen Generating and Sustaining Gel

| Ingredient | Grams | Function |
|---|---|---|
| Konjac glucomannan | 278.430 | gelling, $H_2$ sequestration |
| malic acid | 136.103 | Flavoring agent, acidifier |
| maltodextrin | 92.716 | sweetener, bulking agent |
| magnesium sulfate - anhydrous | 9.234 | desiccant, anti-caking |
| aspartame | 7.729 | sweetener |
| 230 Mesh Magnesium Metal Powder Powder | 5.529 | Generate $H_2$ |
| acesulfame | 3.759 | sweetener |
| mixed tocopherols | 4.599 | anti-oxidant, freshener |
| FD&C Yellow # 5 | 0.464 | Coloring agent |
| Total | 538.563 | |

A unit dose, i.e., 5.835 grams, of the batch, was delivered to an empty 8-ounce plastic cup. Thereafter, 100 mL of distilled water was added and mixed with a spoon. Within 120 seconds, a gel formed and expanded by 25% within an hour, demonstrating the generation and sequestration of molecular hydrogen. The gel was judged to have excellent organoleptic properties—including taste, tartness, and texture. Thereafter, it was entered into an 'in use' test.

4. Discussion

The results demonstrate the feasibility of scaling up formulations containing magnesium metal powder and glucomannan for generating and sustaining molecular hydrogen.

Example 17: Oral Health: Treatment Gingivitis with a $H_2$-Chlorhexidine in a Magnesium metal powder-Glucomannan Gel It is well known that gingivitis (i.e., gum inflammation) leads to periodontal disease. It is the leading cause of tooth loss in both humans and animals. Older dogs and cats are particularly susceptible to periodontal disease.

Drugs, such as chlorhexidine, an anti-microbial, and anti-inflammatories (NSAIDS) have been used in the oral cavity to reduce inflammation affecting gingivitis and resultant periodontal disease. These treatments have been only partially effective. There is a need for both better sustained delivery systems of antimicrobials and for more effective, longer lasting anti-inflammatory therapies. Studies attest to the antibacterial activity of molecular hydrogen water against oral bacteria.

A gel containing 0.12% chlorhexidine gluconate and 22.1% molecular hydrogen($H_2$), a potent anti-inflammatory and antioxidant, was prepared: Three mL of Hibiclens® (4% w/v chlorhexidine) was diluted to 0.12% with 97 mL of distilled water. The solution was then added to an 8 oz. plastic cup containing 99 mg of crude magnesium metal powder and 4.0 g of glucomannan powder. Mixing took place for about 30 seconds, at which time a gel started to form. A line was placed at the top of the gel to delineate its height in the cup at that time. The gel was allowed to expand overnight. Thereafter, a second line was placed on the top of the gel where there was a new gel height. The volume of $H_2$ in the gel was calculated by multiplying the difference, in centimeters, between the two lines times the area of the base of the cup (i.e., 28.3 square cm.). The volume of hydrogen was calculated to be 28.3 mL. Thus, the total volume of the gel, after expansion is 128.3 mL, resulting in a concentration of $H_2$ of 22.1% in the gel.

An N=1, Phase 1 therapeutic trial was carried out. The subject periodically develops gingivitis and has a history of periodontal disease despite good oral hygiene. Thirty-five mL of the gel was placed in the oral cavity with a spoon and then spread over the surface of the gums and teeth with the subject's tongue. The subject found the taste much more acceptable compared to other therapies, for example, a therapeutic oral rinse. The gel was retained in the oral cavity for ten minutes. Symptoms associated with gingivitis, such as sensitive gums, was ameliorated within twelve hours.

The gel can be applied to the gums by other means such as use of a tongue depressor, a regular toothbrush, an electric toothbrush or any other appropriate means. If the gums are sensitive, application with a 'Q' Tip may be preferred. Regardless, the gel should be retained in the oral cavity for as long as possible. Chlorhexidine and $H_2$ will diffuse between the teeth. Ten minutes is recommended. Then, it can be washed out with water or mouthwash. Hydrogen peroxide should not be used since it reacts with $H_2$ and deactivates it.

It was determined that this product is of utility for veterinary oral care for older animals (e.g., dogs and cats) since it is substantive to the oral cavity. Dogs and cats are subject to tooth loss due gingivitis resulting in periodontal disease. The gel can be administered to animals in an analogous manner as done for humans. An alternative method of delivery consists of incorporating a 'treat' into the gel. For example, a gel was prepared as described above, with the addition of 2% peanut powder. The gel was readily taken into the oral cavity where a significant amount stuck to the gums and teeth, thereby delivering chlorhexidine and $H_2$ to the gums for an extended period.

Compositions as described herein could alternatively be formulated in to a toothpaste for delivery to the oral cavity and gums.

Example 18: Gastrointestinal Diseases: Sustained Release of $H_2$ and Bismuth Subsalicylate from a Magnesium Metal Powder-Glucomannan Gel There are diseases and conditions of the upper gastrointestinal tract where sustained delivery of both effective drugs and $H_2$ would have an advantage over current treatments. Compositions described herein provide effective treatment of conditions such as gastritis; gastric and duodenal ulcers, gastroesophageal reflux disease (GERD), Helicobacter pylori infection, bacterial overgrowth, yeast overgrowth, heartburn, indigestion, upset stomach and nausea. Non-limiting examples of drugs that could be delivered from hydrogen-rich Mg-gmn gels are proton pump inhibitors, misoprostol, $H_2$ receptor antagonists, antibiotics, antifungals, anti-inflammatories, antacids, bismuth subsalicylate, or any combination thereof. These drugs alone or in some combinations, at therapeutic doses, can be incorporated into aqueous Mg-gmn gels.

As an example, 50 mg Mg* plus 4 g of glucomannan were mixed and added to a solution containing 30 mL of a solution containing 1.050 g bismuth subsalicylate and 70 mL of distilled water. The mixture was stirred for 60 seconds, at which point the resultant solution gelled. A line was drawn to mark the gel height. The initial height was 5.3 cm indicating a gel volume of 179.4 mL. The weight of the gel was 107.89 g implying a density of 0.602 g/mL. Comparably speaking, this is a low density-relative to previously tested 4% gmn-—20 mg Mg* gels (See Table 2). The gel was allowed set for 3 hours. The height of the gel was determined to be 5.6 cm. with a gel volume of 185.8 mL and a density of 0.581 g/mL. The $H_2$ content of the gel, as measured with the Trustlex $H_2$ Meter was 1405 ppb at a pH of 7.25. The low density of this gel, at outset, and its high $H_2$ content, demonstrates that copious amounts of $H_2$ was generated at the outset of mixing and gelling of the gel. (NB: Letting the gel set for more than a few minutes is not necessary since the gel will continue to generate $H_2$ in the stomach for a prolonged period).

Subsequent oral administration of the mixture described above to a subject experiencing acute heartburn resulted in resolution of symptoms with no discernible side effects.

Example 19: Mg-glucomannan to treat of Helicobacter pylori infection

Bismuth subsalicylate, in combination with antibiotics (250 mg of metronidazole and 500 mg of tetracycline) has been used to eradicate Helicobacter pylori infections. 250 mg metronidazole, 500 mg tetracycline, and 1.055 g bismuth subsalicylate are incorporated into a Mg*-gmn formulation. Such a formulation could be marketed as tablets, capsules or a powder. A gel could be formed in a glass of water—by adding the formulation and mixing and then ingesting the gel. Alternatively, the patient could ingest a capsule (or tablet) containing the formulation followed by an 8 to 16-ounce glass of water. The gel will spontaneously and rapidly form in the stomach and it will 'float' affecting a long retention time in the stomach. Long lasting, i.e., 5 to 10-hour delivery of $H_2$ and the drugs should be achieved.

An example formula for treatment if Helicobacter pylori and bacterial overgrowth provided in a dosage of six '000' capsules is:
  1.0 g bismuth subsalicylate
  250 mg of metronidazole
  500 mg of tetracycline
  3.0 g glucomannan
  50 mg of 63-micron magnesium metal powder Alternatively, the above formula can be mixed with water in a 12-ounce glass that will spontaneously form a gel, within 5-minutes—that can be ingested without side effects.

Example 20: Treatment of Skin Disorders with Molecular Hydrogen-Salicylic Acid in a Magnesium Metal Powder-Glucomannan Gel Until now, there was no practical manner for sustained topical delivery of $H_2$ to the integument.

An anti-acne, keratolytic preparation consisting of 54 mg Mg* (63-micron particle size), 2 g salicylic acid, 2 g konjac root glucomannan in 100 mL distilled water was prepared in a plastic cup by mixing the components for 45 seconds while a gel formed. The gel was allowed to set overnight. The volume expansion of the gel was found to be 34.0 mL or 34%. Therefore, the expanded gel contains 34 mL of $H_2$. The pH of the gel was found to be 3.34.

Two 'quarter'-sized areas (4.15 square cm.) were delineated on the hair clipped skin of the right forearm of a male subject. One site served as an untreated control while the other site was treated topically with 0.24 g/square cm. of the gel. The gel was spread over the site with a tongue depressor in a continuous layer. The $H_2$ in the gel, on the skin surface, was determined with the Trustlex® $H_2$ Meter—without the Protective Guard. Removing the Protective Guard allowed for direct contact of the Trustlex® electrode with the skin surface. Thus, the concentration of $H_2$ being delivered to the skin surface can be determined. The presence of salicylic acid on the skin surface and in the stratum corneum was observed with a Wood's Light (UVA). Salicylic acid fluoresces in the UVA, allowing it to be seen on the skin surface under UV light. Tape stripping (3M Scotch Tape) the skin on the site allows for determining the layers of stratum corneum penetrated by salicylic acid. That is, each tape strip of the salicylic acid-treated site represents a layer of stratum corneum penetrated by salicylic acid.

It was found that, after washing off the remaining gel from the skin site, it took ten tape strippings of the treated site to remove the visible presence of the UVA fluorescence. Thus, the gel delivered salicylic acid through 9-10 layers of stratum corneum, close to the lowest layers of the stratum corneum of forearm skin.

The time course of change in $H_2$ on the skin surface after application of the $H_2$-rich gel, was followed. At baseline, it was determined that 432 ppb $H_2$ was in contact with the skin surface. Within 10 minutes 250 ppb $H_2$ was detected at the skin surface. At 20 minutes 167 ppb $H_2$ was detected at the skin surface. At 30 minutes, it had dropped to zero. It is assumed that a substantial portion of the $H_2$ in contact with the skin surface was absorbed into the skin. Also, once water has evaporated from the skin surface, it is no longer available to react with Mg to generate $H_2$. The stratum corneum, the top barrier of the skin, is hydrophobic. $H_2$ is also hydrophobic. Thermodynamically, hydrophobic entities associate with each other, in an aqueous environment. This shows the composition as described above can deliver both $H_2$ and salicylic acid to the integument. Mg-gmn gels containing numerous drugs, alone or in combination are feasible for treating various skin afflictions.

Non-limiting examples of skin diseases and conditions that can be treated and drugs that can be incorporated into $H_2$ Generating Mg-gmn skin care products are:
  aging skin: alpha-hydroxy acids, antioxidants, ascorbic acid, trans-retinoic acid;
  acne: doxycycline, lymecycline, minocycline, erythromycin, trimethoprim, cotrimoxazole, salicylic acid, trans-retinoic acid;
  dry, flaky or thickened skin: alpha-hydroxy acids, salicylic acid, glycerin;
  allergic contact dermatitis: corticosteroids, topical antihistamines;
  atopic dermatitis: corticosteroids, antihistamines;
  psoriasis: salicylic acid, corticosteroids, coal tar, immunosuppressants;
  sunburn: topical anesthetics, aloe vera, NSAIDS;
  bruising: arnica, vitamin E, vitamin C;
  irritated skin: glycerin, cholesterol sulfate;
  fungal infections: clotrimazole, econazole, miconazole, terbinafine, fluconazole, ketoconazole, amphotericin;
  corns and callouses high dose salicylic acid;
  combinations of the drugs listed above for complex diseases; or
  dermatology preparations, containing abundant $H_2$ need special preparation and/or packaging.

In some embodiments, solids containing Mg and glucomannan must be in a separate compartment from water. They would be mixed 'in situ' in unit-dose packages. The lotion or gel generated would contain abundant $H_2$ for about a week. A preservative, such as sodium adipate, may be added.

An alternative means of stabilization for marketing would be to generate $H_2$ within the formulation, by mixing liquid and solid phases during manufacturing and sterilizing. This product would then be packaged in a sealed aluminum container that can give it a shelf life of over a year. It is best packaged in small doses that would last the consumer about a week.

Example 22: $H_2$ Moisturizing Gel for Dry, Aging skin

As skin ages normally or from environmental damage, it is subject to sub-chronic inflammation and hyperproliferation which affects difficulty in holding moisture. A moisturizing product that will reduce sub chronic inflammation without drugs that cause irritating side effects, is needed.

The following $H_2$-generating moisturizing skin lotion was prepared:

3.0 g lactic acid;
1.5 g glucomannan;
51 mg Mg* (63 micron);
20 mL glycerin
80 mL distilled water For preparation, glycerin and distilled water were mixed and added to the remaining ingredients in an 8 oz. container and mixed for 60 seconds until the contents were dissolved. A lotion resulted. The lotion was allowed to stand at 23 C for one hour. The Trustlex $H_2$ Meter indicated that the lotion contained 815 ppb $H_2$ at a pH of 3.86.

Two quarter-sized areas (4.15 square cm.) were delineated on the hair clipped skin of the right forearm of a subject. One site served as an untreated control site while the other site was treated topically with 0.15 g/square cm. of the lotion. The lotion was spread over the site, with a tongue depressor, as a generous layer of lotion. $H_2$ on the skin surface, was determined with the Trustlex® $H_2$ Meter without the Protective Guard. Removing the Protective Guard allowed for direct contact of the Trustlex® electrode with the skin. The electrode was wetted with distilled water before touching the skin surface.

The time course of change in $H_2$ on the skin surface is shown in Table 12. At baseline, the $H_2$ on the skin surface was 804 ppb, close to that in the lotion (i.e., 814 ppb). As time progressed, the $H_2$ on the surface of the skin fluctuated and did not show a progressive loss, as expected, up to 60 minutes. Thereafter, $H_2$ measurements on the skin surface showed the presence of significant $H_2$ up to 210 minutes.

TABLE 12

Time Course of Change in $H_2$ on Skin Surface after Application of a $H_2$-Rich Anti-aging Moisturizing Lotion

| Time (Min. | Treated* $H_2$ ppb | Untreated $H_2$ ppb |
| --- | --- | --- |
| 0 | 804 | 0 |
| 5 | 756 | 0 |
| 10 | 917 | 0 |
| 15 | 327 | 0 |
| 20 | 351 | 0 |
| 30 | 330 | 0 |
| 60 | 791 | 0 |
| 120 | 169 | 0 |
| 210 | 247 | 0 |
| 360 | 0 | 0 |

*Treated with 51 mg Mg*(63 microns), 3.0 g lactic acid, 1.5 g glucomannan, 20 g glycerin and 80 g distilled water, $H_2$ = 815 ppb, pH = 3.86.
Skin Surface pH = 4.57.

This level of persistence of $H_2$ on the skin surface was surprising and unexpected. The lotion rapidly loses most of its water as it dries on the skin surface. Bubbles disappear. Only a thin layer of product remains on the skin surface. However, such persistence may be explained by:

Mg*, deposited on the skin surface by the lotion, continues to react with water held on the skin surface by the hydroscopic effect of glycerin and lactic acid;

As noted in previous Examples, $H_2$ has an affinity for glucomannan. Therefore, glucomannan may contribute to $H_2$ persistence on skin;

The stratum corneum has a reservoir effect for hydrophobic molecules. $H_2$ is hydrophobic. It may contribute to the $H_2$ detected on the skin surface due to back diffusion of $H_2$ from the stratum corneum.

Example 23: Sustained Delivery of $H_2$ to a Model Aquarium or Fish Farm

It has previously been demonstrated that molecular hydrogen ($H_2$) can promote the health and growth of both animal and plant life (1, 14). Aquatic life in the form of plants, invertebrates (e.g., shrimp, crabs, etc.) and fish should also benefit from the antioxidant and enhanced bioavailability effects of $H_2$ in an aqueous environment. Plants, fish, insects and all invertebrates, like higher animals, have mitochondria. $H_2$ is known to reduce the toxic reactive oxygen species (ROS), i.e., hydroxyl radical and peroxynitrite produced by mitochondria. These promoters of inflammation affect the consumption of energy that could otherwise be used for growth and fighting disease.

An experiment was designed to determine if a magnesium metal powder (Mg)-glucomannan(gmn) gel that generates $H_2$ can deliver and sustain $H_2$ in a model aquarium or aquatic farm. For the model aquarium or fish farm, 9.95 grams of Fisher® phosphate buffered saline (PBS) in 1,000 mL of distilled water was prepared. The pH was 7.6.

For preparing the gel, 0.1 g of crude magnesium metal powder (Mg), 0.5 g of ascorbic acid and 4 g of glucomannan were mixed into 100 mL of distilled water (DW)—until the gel started to form. The $H_2$ concentration in the gel was determined to be 1501 ppb—using the Trustlex® $H_2$ Meter, at a pH of 8.4. The gel expanded in height by 0.9 cm. Thus, the volume of $H_2$ in the gel is 25.5 mL or 25.5% of the original 100 mL volume.

After the baseline reading, the 125 mL gel was placed in the 1,000 mL PBS solution representing the aquarium or fish farm. Being less dense than water, the gel floated on top of the 1,000 mL beaker. The PBS was constantly circulated, at 23 C, by stirring with a 1 in. magnetic stirring bar at the lowest power setting on the magnetic stirrer.

The results are shown in Table 13. At baseline, there was found to be 0 ppb $H_2$ in the PBS solution, at a pH of 7.6. After 15 minutes, the $H_2$ in the PBS remained at 0 ppb, at a pH of 7.6. By 4.7 hours, there was 562 ppb $H_2$ in the PBS, at a pH of 7.7. At 13.8 hours, $H_2$ in the PBS had risen to 691 ppb, at a pH of 7.7. As time progressed, there was an accumulation of small white debris in the PBS. This accumulation appeared to be a product of shedding gmn particles from the floating gel. Upon cessation of stirring, this material tended to float to the top of the beaker—near the gel supporting the notion that it is gmn particles. At 28.3 hours, the $H_2$ in the PBS had risen to 1245 ppb at pH 7.6. Thereafter, the $H_2$ in the PBS was sustained at a level of 1202 ppb, pH 7.3 until 109 hours. At 123 hours there was 1165 ppb $H_2$, pH 6.8. The pH drop probably indicates bacterial growth in the simulated tank.

TABLE 13

Test System for Delivery of Molecular
Hydrogen ($H_2$) to Aquatic Life

| Time (Hrs.). | ppb $H_2$ in PBS | pH Units |
|---|---|---|
| 0 | 0 | 7.6 |
| 0.25 | 0 | 7.6 |
| 4.7 | 562 | 7.7 |
| 13.8 | 691 | 7.7 |
| 28.3 | 1245 | 7.6 |
| 86.0 | 1234 | 7.3 |
| 109.0 | 1202 | 7.3 |
| 123.0 | 1165 | 6.8 |

This experiment demonstrates the feasibility of delivering $H_2$ to an aquarium or aquatic farm. It also points to routine steps that must be taken to insure the maintenance of water quality in an aquarium or fish tank. These maintenance steps include those that would normally be carried out without addition of the gel: filtration of excess particles out of the tank, include antibacterial and anti-algae agents that are compatible with the aquatic life in the tank. If proper maintenance is carried out, the water should be acceptable for 2-4 weeks.

For situations when the body of water contained in the tank is larger than 20:1 tank to gel ratio, fish or invertebrate meal can be incorporated into the gel. This maneuver should attract fish or invertebrates to the gel where they will consume a higher level of $H_2$.

The applications foreseen for this method of delivery of $H_2$ to aqueous systems, of such, include:

home aquariums containing aquatic plants, fish, turtles, invertebrates;
crustacean and mollusk, oyster farms;
fish farms including catfish, tilapia, salmon and carp; or
farming aquatic plants including rice, algaculture seaweed and ornamental plant farming.

Of importance, is the potential of $H_2$ delivery to aquatic systems to increase the yield of aquatic food to feed the world's growing population and to protect the environment against over-fishing and destruction of aquatic plant life.

Example 24: Molecular Hydrogen-Rich Magnesium Metal Powder-Glucomannan Gels for Increasing Insect Yields As the world's population increases beyond 7,650,000,000, it becomes increasingly difficult to provide complete nutritional food, particularly in the form of complete protein and associated amino acids. There is increasing interest in farming insect populations to feed the growing masses. Insects are an excellent source of complete protein, vitamin B12, vitamin A and riboflavin. They reproduce and grow rapidly and eat almost anything. They are particularly attracted to necrotic life forms, rotting food and feces. Thus, they are 'natural' cleaners of the environment. Crickets, cockroaches, grasshoppers, beetles, moths, etc. are now being farmed for both human and animal consumption.

Insect food can also serve as food for lower animals, including poultry and fish farming.

Farming of insects has several advantages over the farming animals, such as cattle and chickens, including reduced feed per yield of protein, greater nutritional efficiency, less concern about epidemics in an insect population compared to an animal population, lower greenhouse gas emissions and lower land usage.

Although insects breed and grow rapidly, a technology that would increase protein and nutritional yield would be of economic benefit to both insect farmers and nutritionally deficient populations. Since molecular hydrogen has been shown to increase reproduction and growth in many life forms (1, 14), mainly through its antioxidant effects thereby reducing mitochondrial reactive oxygen species, there is no good reason to doubt its growth promoting effects in insect populations. Insect cells are powered by mitochondria.

A prototype insect farming system was modeled to determine if wildtype insects would be attracted to a molecular hydrogen ($H_2$) gel that was prepared in an 8 oz. plastic cup. The gel was formulated as follows: 51 mg of Mg plus 4 g of glucomannan and 5 g of fructose were mixed in an 8 oz. plastic cup. Next, 100 mL of white vinegar (5% acetic acid) was added to the cup and the contents mixed with a tongue depressor until the gel formed. The height of the gel was delineated with a blue line drawn with a marking pen. The gel was allowed to stand for one hour for the gel to form and evolve $H_2$. The new gel height was again delineated with a marking pen. The $H_2$ content of the gel was then measured by immersing the unguarded Trustlex® electrode into the gel. The $H_2$ content of the gel was found to be 800 ppb at a pH of 3.35. The plastic cup containing the gel was placed outside of the laboratory in a garden like atmosphere. The temperature ranged from 90-105 F. Over the course of 24-hours, the gel was observed for the presence of insects. Bees, flies, fruit flies, ants and other un-identified insects appeared to be attracted to the gel.

The purpose of placing insect food, in this example, fructose and acetic acid, in the $H_2$-rich gmn gel, is to attract insects to the gel thereby exposing the insects to a high dose level of $H_2$. As the insects ingest both the insect food and the glucomannan, they will come into close contact with $H_2$ which will be both ingested and absorbed into their body parts that are in contact with the gel.

The example gel illustrated here, is not optimized for the most efficient delivery of $H_2$ for insect farming. Cost of the gel is important, since it must be lower than the value of the increased yield of the nutritional benefit of this biotechnology. To this effect, costs can be minimized by:

use of acidic food waste or acetic acid waste (0.25-7%) rather than high quality acetic acid for acidification;
use a minimum dose of glucomannan (e.g., 1.5-2.5%) alone or in combination with low dose maltodextrin (e.g., 0.5%);
use 10-100 mg of crude magnesium metal powder (Mg); and
water can be any water free of toxic metals, plasticizers, endocrine disrupters and pesticides.

Example 25: Effect of Glucomannan on Generation and Sustaining Molecular Hydrogen ($H_2$) in Aqueous Solutions—Bellow the Gelling Concentration 5. Introduction A study was carried out, in an open 'to the air' container, to determine if low levels of glucomannan (gmn), below the gelation concentration, combined with magnesium metal powder (Mg*) can increase the sustainability of $H_2$ in Mg*-gmn aqueous solutions—relative to Mg* solutions—without glucomannan.

6. Experimental

Crystal Light® powder was used since previous experiments (Examples 10 and 11 above) have demonstrated the effectiveness of the aqueous Crystal Light® media in supporting $H_2$ generation from Mg-gmn formulations.

Crystal Light® Natural Lemonade powder was mixed with all test powders, including the control without glucomannan. All formulations tested contained 40 mg of 63-micron (230 Mesh) magnesium metal powder (Mg*) and 1.9 g of Crystal Light® Natural Lemonade (CL). Crystal Light®

Lemonade contains citric acid, potassium citrate, sodium citrate, aspartame, magnesium oxide, maltodextrin, acesulfame potassium, soy lecithin, artificial color FD&C Yellow #5, BHA and less than 2% natural flavor.

Six different test solutions were prepared containing 0.0, 0.15, 1.5, 12, 100 and 1,000 mg of glucomannan (gmn). The Mg*-gmn plus CL powders were combined and mixed. The formulations were then mixed with 100 mL distilled water (DW) in a 250 mL glass beaker. Close to two-minute mixings took place. Immediately after mixing, measurements of molecular hydrogen ($H_2$) took place by immersing the Trustlex® $H_2$ Meter, without its guard cup, in the test solution until a steady reading was reached. Removing the guard cup allows un-impeded contact of the Trustlex® electrode with the gel.

Viscosity measurements on the control and test solutions took place with a #6 Zahn Viscosity Cup for testing the viscosity of Newtonian liquids. It can be used to measure the time, in seconds, for the test solutions to flow out of the cup that is filled to its capacity.

7. Results

The results are shown in Table 14 and FIG. 1. In Column 2 of Table 14 are displayed the time points at which $H_2$ measurements were taken—starting right after two minutes of stirring a mixture.

from aqueous solution. This persistence of $H_2$ in Mg*-generated $H_2$ solutions is attributed to continued generation of $H_2$, for a period of time after Mg* is mixed with water.

After one hour, there is a faster rate of loss of dissolved $H_2$ from the control solution so that at 6-hours post preparation, only 18% of the original amount of dissolved $H_2$ remains. Thus, it appears that there are two phases as is observed by analyzing FIG. 1: A 'Steady State Phase' where dissolved $H_2$ is generated at approximately the same rate that it is lost to the environment, and a 'Depletion Phase', when dissolved $H_2$ is lost to the environment at a faster rate than can be replaced by a reaction of the unreacted Mg* with water.

9. Test Formulations

Formulations all containing 40 mg Mg*+1.9 g CL and also containing respectively, 0.15, 1.5, 12, 100 mg and 1.0 g glucomannan mixed with 100 mL of distilled water—were tested. At these low concentrations of gmn, viscous gels are not formed. The results presented in Columns 5, 7, 9, 11 and 13 show the ppb of dissolved molecular hydrogen ($H_2$) remaining in solution—as a function of time. It is observed that there is a dose-response relationship where glucomannan extends the 'Steady State' Phase, beyond the 60-minute cut-off time found for the control solution—without glucomannan in the formulation. This phenomenon is seen by

TABLE 14

Time Course of Loss of Dissolved Molecular Hydrogen from Solutions Containing Various Non-Gelling Levels of Glucomannan

| 1 Row | 2 Time Min. | 3 gmn 0 $H_2$ ppb | 4 % Rem | 5 gmn 0.15 mg $H_2$ ppb | 6 % Rem. | 7 gmn 1.5 mg $H_2$ ppb | 8 % Rem. | 9 gmn 12 mg $H_2$ ppb | 10 % Rem. | 11 gmn 0.1 g $H_2$ ppb | 12 % Rem | 13 gmn 1 g $H_2$ ppb | 14 % Rem. |
|---|---|---|---|---|---|---|---|---|---|---|---|---|---|
| 1 | 0 | 807 | 100 | 785 | 100 | 800 | 100 | 808 | 100 | 784 | 100 | 803 | 100 |
| 2 | 5 | 806 | 99.9 | 798 | 101.7 | 808 | 101.0 | 804 | 99.5 | 789 | 101 | 820 | 102 |
| 3 | 10 | 812 | 100.6 | 804 | 102.4 | 809 | 101.0 | 804 | 99.5 | 790 | 101 | 824 | 103 |
| 4 | 15 | 814 | 100.9 | 805 | 102.6 | 812 | 102.0 | 806 | 99.8 | 790 | 101 | 826 | 103 |
| 5 | 20 | 808 | 100.1 | 809 | 103.1 | 814 | 102.0 | 806 | 99.8 | 793 | 101 | 828 | 103 |
| 6 | 30 | 802 | 99.4 | 808 | 1029 | 812 | 102.0 | 806 | 99.8 | 789 | 101 | 825 | 103 |
| 7 | 40 | 798 | 98.9 | 806 | 102.7 | 810 | 101.0 | 807 | 99.9 | 792 | 101 | 823 | 103 |
| 8 | 50 | 794 | 98.4 | 804 | 102.4 | xxx | xxx | 806 | 99.7 | 791 | 101 | 819 | 102.0 |
| 9 | 60 | 786 | 97.4 | 802 | 102.1 | 808 | 1.01 | 805 | 99.6 | 791 | 101 | 816 | 102 |
| 10 | 120 | 646 | 80.0 | 758 | 96.6 | 784 | 98.0 | 790 | 98.3 | 783 | 99.9 | 802 | 99.8 |
| 11 | 180 | 431 | 53.4 | 549 | 69.9 | 680 | 85.0 | 753 | 93.2 | 761 | 97.1 | 790 | 98.4 |
| 12 | 240 | 299 | 37.1 | 379 | 48.3 | 440 | 55.0 | 592 | 73.3 | 686 | 87.5 | 789 | 98.3 |
| 13 | 300 | 201 | 24.9 | 234 | 29.8 | 321 | 40.1 | 450 | 55.7 | 526 | 67.1 | 789 | 98.3 |
| 14 | 360 | 146 | 18.1 | 161 | 20.5 | 202 | 25.3 | 309 | 38.2 | 394 | 50.3 | 802 | 99.9 |
| Visc. (sec.) | | 1.2 | | xxx | | xxx | | 1.1 | | 1.7 | | 23.0 | |

Abbreviations
% Rem. % dissolved $H_2$ remaining in solution - as measured with the Trustlex $H_2$ Meter.
Visc. Viscosity
Min. Minutes
ppb parts per billion
$H_2$ molecular hydrogen
gmn glucomannan
g gram
mg milligram
sec. seconds 8. Control Formulation Columns 3 and 4 of Table 14 show respectively, the parts per billion (ppb) and percent of dissolved $H_2$ remaining in solution due to generation in the control formulation (i.e., 40 mg Mg*+1.9 g CL—without glucomannan). It is observed that there is an almost steady state level of $H_2$ in solution up to one-hour after starting measurements. This phenomenon is clearly depicted in FIG. 1. This result, at first glance, is surprising, since experience in generating $H_2$ by electrolysis of water has shown a much more rapid rate of loss of $H_2$ observing the results presented in FIG. 1. Even at the lowest concentration of glucomannan tested (1.5 ppm), the 'Steady State' Phase is shifted from lasting 1-hour to close to 2-hours. Formulations containing higher concentrations of gmn progressively increase the length of the 'Steady State' Phase as can be seen by analyzing the results in Columns 3-14 of Table 14 and FIG. 1. The results presented in Columns 13 and 14 of Table 14 and FIG. 1—show that the 40 mg Mg*+1.9 g CL formulation containing 1.0 g of gmn/100 mL DW extends the 'Steady State' Phase to 360 minutes (6-hours)—and perhaps well beyond the 6-hour time course of this Study. In fact, previously described studies (See Examples 4 and 5, above) attest to the long-term stability of $H_2$ in Mg-gmn gels. However, as tested here, 40 mg of Mg*+1.9 g CL formulations containing, respectively, 0.15, 1.5, 12 and 100 mg of gmn/100 mL DW extend the 'Steady State' Phase without appreciably increasing the viscosity or forming a gel. The 40 mg Mg*+1.9 g CL formulation containing 1.0 g of gmn/100 mL DW modestly increases the viscosity, forming a viscous solution but does not form a viscous gel.

10. Discussion

Reviewing the results of the 1 to 6-hour time frame as depicted in Table 14 and FIG. 1, it is observed that the 'Steady State' Phase progressively increases while the 'Depletion Phase' progressively decreases as the concentration of glucomannan is increased in the 40 mg Mg*+1.9 g CL formulations. For the formulations containing 0.15 mg to up to 1.0 g of gmn, this remarkable stabilization of $H_2$ in the solutions cannot be due to a gelation effect. In an attempt to understand the mechanism by which 'below gelling concentrations' of glucomannan sustain $H_2$ in 40 mg Mg*+1.9 g CL aqueous solutions, the following possibilities are considered:

gmn slows down the reaction of Mg* with water which generates $H_2$;

gmn has an affinity for $H_2$ which slows down its loss to the environment from solution;

gmn stabilizes $H_2$ bubbles, in solution, thereby slowing down the rate of loss from solution; or gmn sustains the generation of $H_2$ in solution by removing the passivation coat of magnesium oxide that is naturally found on magnesium metal powder particles that have been exposed to oxygen.

Analysis of the data can eliminate possibility '1' above. By observing the results for the control solution in Columns 3-4, relative to the results for the test solutions in Columns 5-14, it is seen that the initial rate of reaction for producing $H_2$ is approximately equal to that of the test solutions (See Row 1). Therefore, glucomannan does not slow down the depletion of Mg and resultant $H_2$ production.

The idea that $H_2$ has an affinity for gmn is more than worthy of consideration. Copious visible bubbles are initially present in solution due to the generation of $H_2$ by magnesium metal powder. Stabilization of these bubbles in solution should create a reservoir of $H_2$ for dynamic exchange with dissolved $H_2$. This phenomenon should lead to increased stabilization of $H_2$ in solution—compared to solutions containing dissolved $H_2$-without microbubbles. Accepting that $H_2$ has an affinity for gmn, it is reasonable to assume that non-gelling gmn molecules and complexes would be attracted to the $H_2$ bubble-water interface forming more stable bubbles.

As discussed in Example 7, glucomannan can possibly catalyze the removal of the passivation coat of magnesium oxide from magnesium metal powder particles, thereby increasing the efficiency of molecular hydrogen production. This mechanism can also play a role in sustaining molecular hydrogen in solutions containing glucomannan.

In summary, there are three mechanisms by which glucomannan can increase the sustainability of molecular hydrogen in aqueous magnesium metal powder solutions.

Example 26: Electrolysis Study: Sequestration of Molecular Hydrogen ($H_2$) by Glucomannan 11. Introduction To test if there is an attractive interaction between $H_2$ and glucomannan, in aqueous solution—in the absence of magnesium metal powder, an independent method of generating $H_2$ in glucomannan solution was sought. Electrolysis of water is a well-known means of generating $H_2$ in solution. The reaction, at the electrodes, breaks down water into $H_2$ and O2. As discussed in the Background Section, above, water free of electrolytes, is needed to prevent chemical reactions that shorten the 'life' of the electrodes. Use of water free of electrolytes, such as distilled water, will generate $H_2$, but at a much slower rate than in the presence of electrolytes.

It was decided to use electrolysis for generating $H_2$ in the presence and absence of gmn. For this purpose, the loss of $H_2$ from solutions after electrolysis of neat distilled water as compared to the electrolysis of distilled water containing 120 ppm glucomannan—was performed.

12. Experimental

Five hundred ml of distilled water containing 62 mg of gmn was prepared in a 500 mL glass beaker by mixing and then heating to 65C to insure gmn solubility. The mixture was then allowed to cool to room temperature (23 C). Electrolysis of water took place in a 460 mL GX-H11 electrolysis bottle from Yongkang Gomax Ind. & Trade Co., Yogkang City, China. The bottle has a working current of 1 Amp. with a DC12V/5V power supply. Electrolysis studies of both distilled water and 120 ppm gmn, in distilled water, were repeated.

13. Results

The time course of the electrolysis results is shown in Table 15. Column 1 shows the time points of measurements after the start of the study. The results in Column 2 show the ppb of $H_2$ generated at each time point after completion of 6 minutes of electrolysis of distilled water (DW). Only 27 ppb of $H_2$ is present at the outset. As shown in Column 3 and depicted in FIG. 2, at one-hour after completion of electrolysis, no detectable $H_2$ remained in the electrolyzed solution. This is in accord with previous observations that electrolysis of DW has a low yield of $H_2$ which depends on the time course of the applied voltage—which is constant for the studies described here.

TABLE 15

Effect of Glucomannan (gmn) on Molecular Hydrogen ($H_2$) Generation by Electrolysis in Distilled Water (DW)

| Time min. | DW (N = 3) ppb $H_2$ | % Change | gmn (N = 2) ppb $H_2$ | % Change |
| --- | --- | --- | --- | --- |
| 0 | 27 | 0 | 197 | 0 |
| 5 | 20 | −26 | 235 | 19 |
| 10 | 18 | −33 | 241 | 22 |
| 20 | 17 | −37 | 243 | 23 |
| 40 | 4 | −85 | 223 | 13 |
| 60 | 0 | −100 | 207 | 8 |
| 120 | xxx | xxx | 155 | −21 |
| 180 | xxx | xxx | 103 | −48 |
| 240 | xxx | xxx | 45 | −77 |

Figure 2:
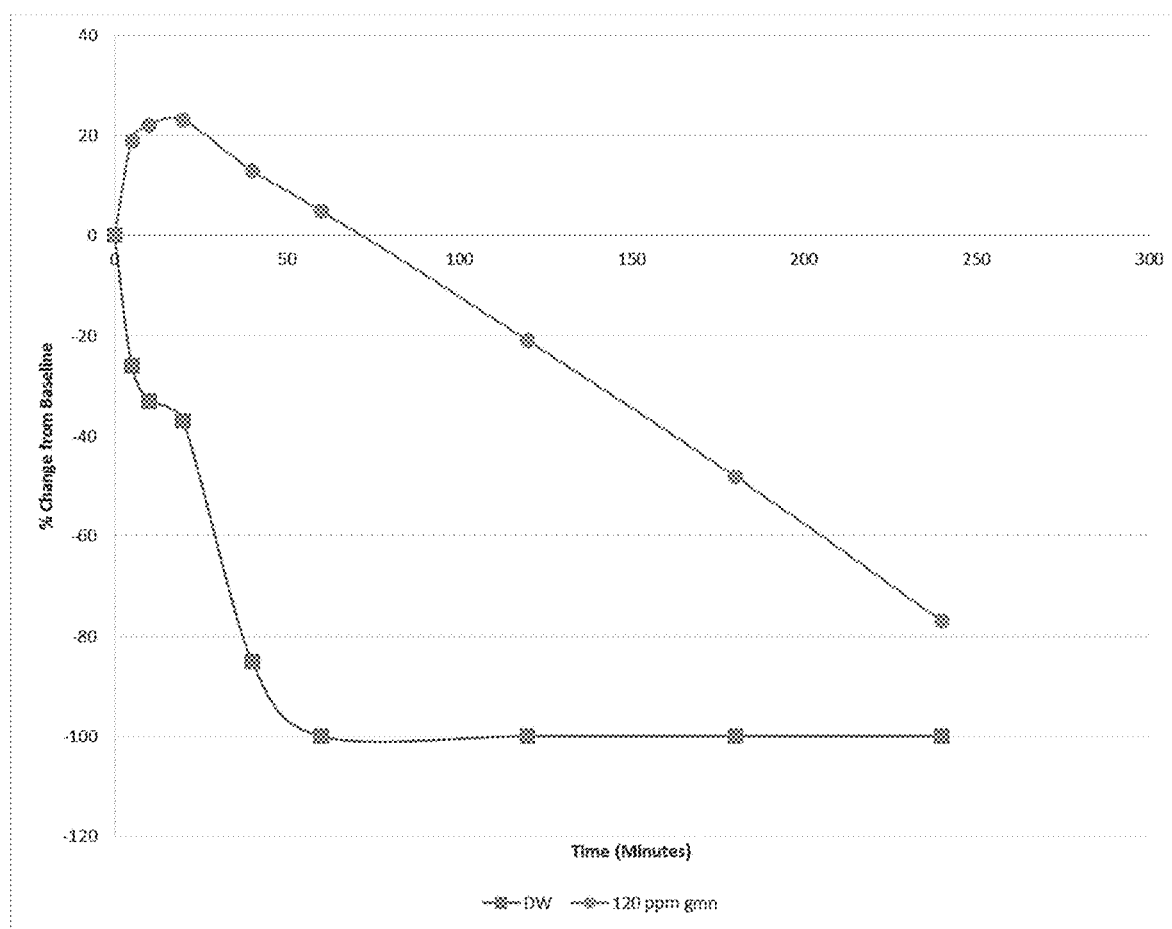
FIG. 2 indicates the time course of hydrogen generation by distilled water electrolysis in the presence and absence of glucomannan.

Abbreviations
gmn—120 ppm glucomannan (0.012%)
ppb—parts per billion $H_2$
min.—minutes after starting $H_2$ measurements with the Trustlex Meter.
$H_2$—Molecular hydrogen
DW—Distilled water
N—Number of repeats The results presented in Column 4 and FIG. 2 show the ppb of $H_2$ generated at each time point after completion of 6 minutes of electrolysis of distilled water containing 120 ppm glucomannan. Immediately after completion of electrolysis, 197 ppb of $H_2$ is detected in the electrolyzed solution. $H_2$ then rises to 243 ppb at 20 minutes after completion of electrolysis. This increase—relative to electrolysis, without gmn, is attributed to an interaction of $H_2$ with gmn that helps retain $H_2$ in solution. Glucomannan, a polymer of glucose and mannose, is not charged and should not directly affect electrolysis. At one-hour after completion of electrolysis, 207 ppb (85%) $H_2$ remains in the electrolyzed solution. $H_2$ persists at 45 ppb at 4-hours after completion of electrolysis.

14. Discussion

FIG. 2 contains a plot of the results that clearly shows the effect that a low dose (120 ppm) of glucomannan has on retaining $H_2$ in solution—without the presence of magnesium metal powder. Thus, glucomannan:

enhances the retention of $H_2$ in water that has been electrolyzed;

affects a rise in $H_2$ for at least 20 minutes after generation of $H_2$ in solution;

stabilizes $H_2$ in the solution—relative to generation of $H_2$ in DW.

Any method of making $H_2$ available to gmn should stabilize $H_2$ in aqueous solution.

These results point to a strong interaction of $H_2$ with gmn, without the presence of magnesium metal powder. Generation and subsequent infusion of molecular hydrogen from a canister or electrolysis of water device into an aqueous solution containing glucomannan is another means by which glucomannan can interact with $H_2$ and stabilize $H_2$ in solution.

Electrolysis devices have been discussed previously. From the results presented here, these devices could be used to deliver $H_2$ to solutions containing gmn. Longer times of electrolysis and higher concentrations of gmn would increase the stability of $H_2$ in aqueous solutions.

Using a commercial source of $H_2$ to deliver $H_2$ to glucomannan solutions is another method to consider. Canisters containing pressurized $H_2$ are commercially available from Restek (34453-PI-Hydrogen; $724.94). $H_2$ generators such as Zen Earth (HX300 Hydrogen Machine—around $2,500) and Parker Hydrogen Generator ($10,000-17,000) are also commercially available. These devices can readily be located on the interne. These canisters and devices can be used to diffuse or pressurize $H_2$ into glucomannan solutions. They provide another reliable source of $H_2$. The disadvantages are cost and a safety issue—if the level of $H_2$ in the surrounding atmosphere reaches 4% v/v or higher.

Another application of the Invention is the sequestration and storage of $H_2$ from environmental sources. This application would be particularly important in third world countries in need of an inexpensive source of energy. $H_2$ is a well-known source of energy as well as administered for improving health. $H_2$ is produced, in quantity, mostly by microbial anaerobic metabolism: in wastewater; wastewater plants; parts of the ocean—by sea life including cyanobacteria; swamps; the gastrointestinal tracts of animals and humans. Passing hydrogen or solutions containing $H_2$ through gmn solutions or filters containing gmn—will result in sequestration of $H_2$ that can be recovered for energy use.

Example 27: Electrolysis of Water in the Presence of 0.05% K Bicarbonate and Glucomannan It is well known that addition of sodium or potassium bicarbonate to 'pure' water such as distilled water, will increase the output of $H_2$ due to electrolysis. However, keeping the concentration of bicarbonate low is desirable due to its 'off taste', as well as keeping sodium or potassium from reaching a level that is detrimental to health of individuals as well as the electrodes.

Since it has been shown that 120 ppm glucomannan (gmn) enhances $H_2$ generation and sustainability in electrolyzed distilled water (See Table 15), an electrolysis experiment was designed to determine if there is such an effect on generation of $H_2$ when 120 ppm gmn is added to 0.05% potassium bicarbonate.

The results are shown in Table 16. The first column lists the time course of the Study. Column 2 shows the change in $H_2$ generated by electrolysis of the K bicarbonate solution as time progresses. In the first 10 minutes, $H_2$ rises by 4% and then progressively falls to losing 52% of $H_2$ at 3 hours and 95% of $H_2$ at 7-hours.

TABLE 16

Effect of Glucomannan (gmn) on Molecular Hydrogen ($H_2$) Generation by Electrolysis of K bicarbonate in Distilled Water (DW)

| Time min. | 0.05% K bicarbonate in DW ppb | % Chg | 0.05% K bicarbonate, 120 ppm gmn in DW* ppb | % Chg |
|---|---|---|---|---|
| 0 | 575 | −4 | 541 | −7 |
| 5 | 591 | −1 | 580 | xxx |
| 10 | 596 | xxx | 565 | −3 |
| 20 | 575 | −4 | 566 | −3 |
| 40 | 554 | −7 | 546 | −6 |
| 60 | 518 | −13 | 528 | −9 |
| 120 | 395 | −34 | 461 | −21 |
| 180 | 289 | −52 | 406 | −30 |
| 240 | 214 | −64 | 347 | −40 |
| 420 | 32 | −95 | 133 | −77 |
| pH | 8.78 | | 7.90 | |

Abbreviations:
gmn—120 ppm glucomannan (0.012%)
Ch—Change in $H_2$ in solution
ppb—parts per billion $H_2$
min. minutes after starting $H_2$ measurements with the Trustlex Meter.
$H_2$—Molecular hydrogen
DW—Distilled water Column 4 shows the time course of $H_2$ changes after 6 minutes (3 minutes×2) of electrolysis of 120 ppm gmn+ 0.05% K bicarbonate in DW. The results were normalized for differences in pH—to those of Column 2—using the Nernst equation. Comparing the results in Column 4 with those in Column 2, it is observed that a similar pattern of $H_2$ increasing from 0 to 5-minutes, followed by a progressive decrease of $H_2$ in solution. However, there is a marked stabilization of $H_2$, in the electrolyzed solution containing gmn with 0.05% K bicarbonate—relative to the electrolysis of 0.05% K bicarbonate solution. After 60 minutes, this effect becomes more obvious. For example, at 2-hours after the start of the study, there is a 16.1% increase in $H_2$ in the electrolytic solution containing 120 ppm gmn while at 7 hours after the start of the study, there is a 416% increase. These results point to microbubbles being present in the electrolysis solution containing 120 ppm glucomannan.

Example 28: Optical Microscopy Detection of $H_2$ Microbubbles

Due to the unexpected enhanced sustainability of $H_2$ in both aqueous magnesium metal powder and electrolysis systems containing glucomannan (gmn), a study was carried out to determine if significant amounts of microbubbles are present in a solution showing enhanced $H_2$ stability. The formulation investigated contained 44 mg Mg*, 120 ppm gmn, 1.9 g Crystal Light® Natural Lemonade powder mixed into 100 mL distilled water. After mixing for 60 seconds in an 8 oz. cup, the formulation was allowed to stand at 23 C for 4.5-hours before filtration and testing. The formulation was filtered through a 400-mesh filter (ATPWONZ Food Strainer) which provides for a larger than 37-micron particle size retention in the filter. Therefore, all microbubbles passing through the 400 Mesh filter were 37 microns or smaller. Thereafter, 20 μL of the filtered solution was injected onto the sintered glass space adjacent to the glass coverslip covering the grid on a hemocytometer. The grid was observed under the 40/0.065 magnification on the OMAX® Binocular Compound Microscope Model: M83EZ.

Figure 3:
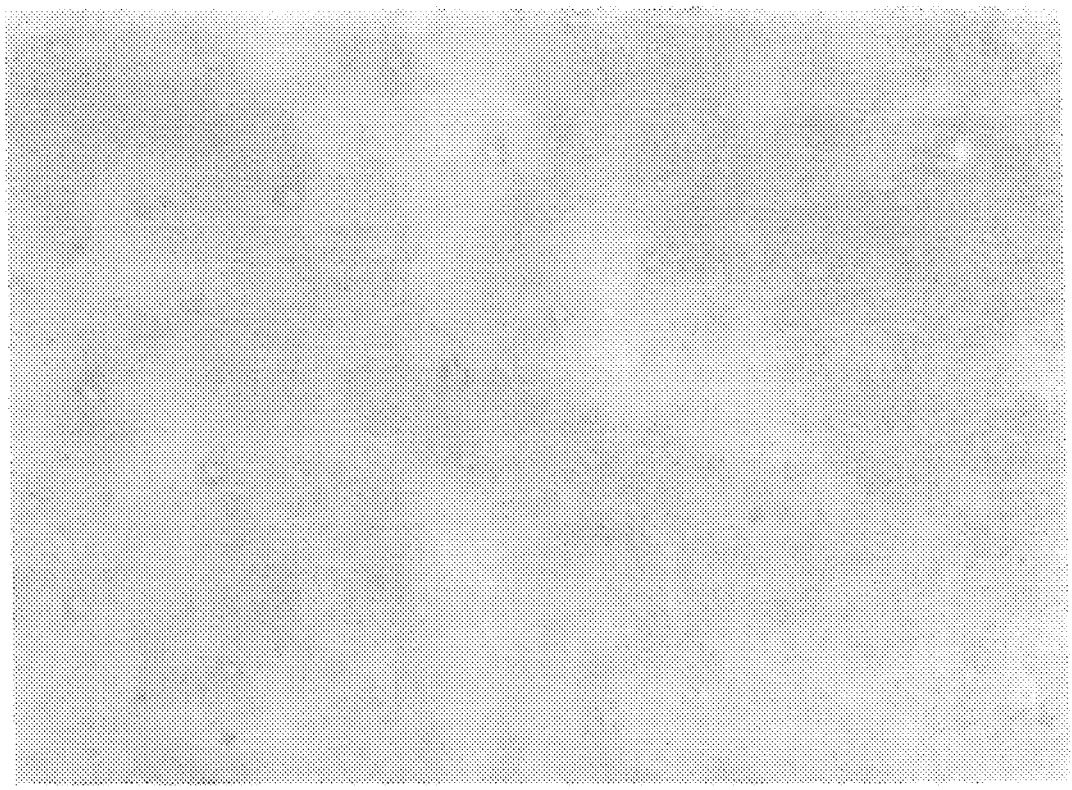
FIG. 3 shows microbubbles observed in a solution 4.5 hours after preparation.

At the 4.5-hour observation, numerous microbubbles were observed, as shown in FIG. 3. Here a wide range of sizes (diameters) are observed. Since the largest size is 37 microns, then the smaller size ranges observed must range between 2-10 microns.

At 8.5-hours, the filtered formulation was refreshed by cleaning and drying the hemocytometer and injecting 20 μL of the solution onto the sintered glass space adjacent to the glass coverslip—covering the grid on the hemocytometer. A wide range of microbubbles of assorted sizes is observed. Thus, the microbubbles observed, have a sustainability of at least 8.5 hours in the 44 mg Mg*, 120 ppm glucomannan, Crystal Light® formula. These results are in accord with the results shown in Columns 9 and 10 of Table 15—where it is seen that 309 ppm $H_2$ (38.2%) is present 6-hours after preparation of a 40 mg Mg*, 120 ppm glucomannan, Crystal Light® solution.

Figure 4:
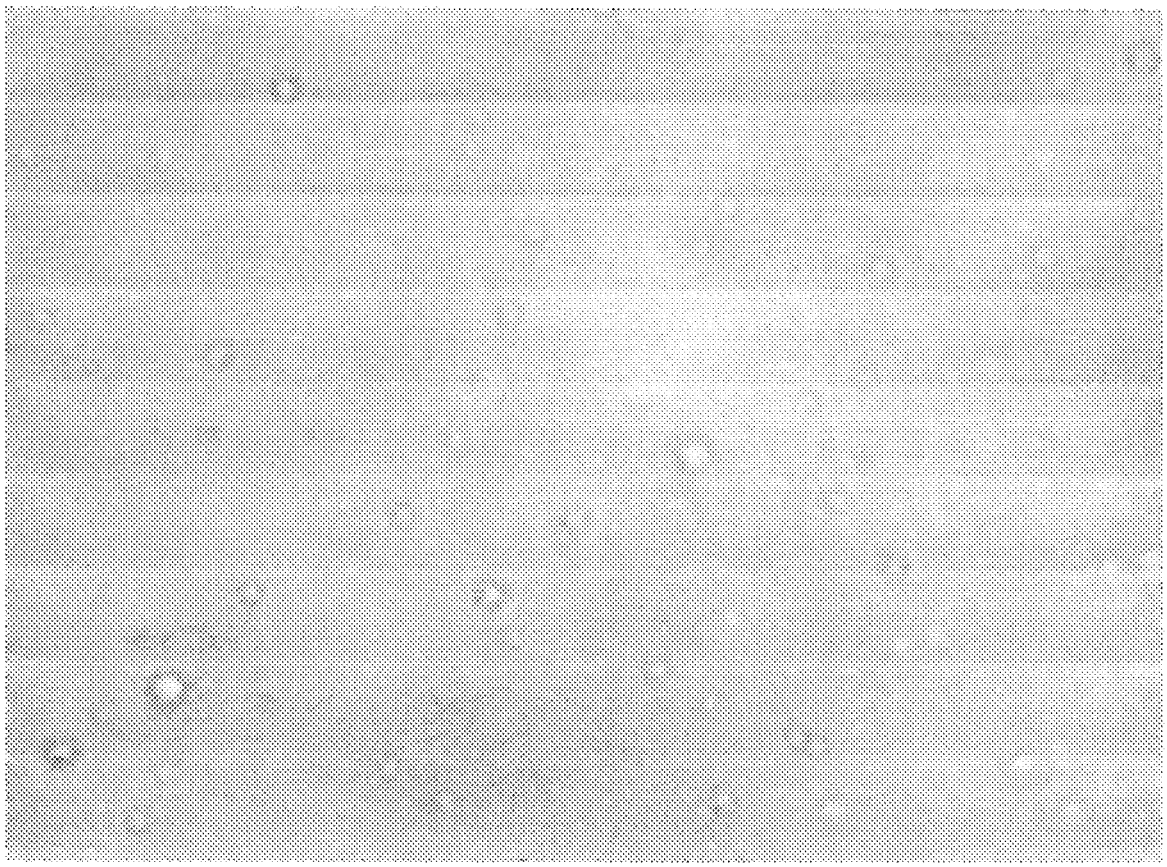
FIG. 4 shows microbubbles observed in a solution 8.5 hours after preparation.

From the results presented in FIGS. 3-4 and Tables 15-17, there is convincing evidence that the persistence of $H_2$ in non-viscous solutions containing glucomannan is due to the stabilization of microbubbles by aqueous glucomannan.

Variable quantities of $H_2$ bubbles in non-viscous glucomannan (gmn) solutions can be generated and controlled by:
  Electrolysis of aqueous 0.5 ppm-1,000 ppm gmn solutions: Extending the electrolysis time and/or voltage, and the presence of bicarbonate electrolytes will increase bubble formation, including microbubbles. Other electrolytes are not recommended due to their adverse effects on the lifetime of the electrodes.
  Reaction of magnesium metal powder (Mg) with water in acidic 0.5 ppm-1,000 ppm gmn solutions. Increasing the concentration of Mg, e.g., 1 mg-1000 mg per 100 mL, will increase the generation of $H_2$ bubbles stabilized by glucomannan.
  Using a hydrogen canister for diffusing or pressurizing $H_2$ into aqueous 0.5 ppm-1,000 ppm gmn solutions. This method requires a source of $H_2$, such as a canister, to be available for use.
  Using a hydrogen generator (e.g., Parker Hannifin 20h hydrogen generator capable of 160 mL $H_2$/min.
  Direct water splitting through vibrating piezoelectric zinc oxide microfibers in aqueous 0.5 ppm-1,000 ppm gmn solutions.

The size of the $H_2$ microbubbles in $H_2$-generating systems can be selected by:
  Molecular sieving, e.g., passing a solution through a 1250 Mesh filter will allow 10 micron or smaller microbubbles to pass.
  Centrifugation where larger bubbles are removed before the microbubbles. The time and speed of centrifugation is contingent on the bubble size cut-off desired.
  Size exclusion chromatography where the microbubbles readily pass through the column while the larger bubbles are held back.

The ability to generate sufficient quantities of stable $H_2$ microbubbles in aqueous solution has important health benefits regarding enhancing ultrasonic biotechnology:

ultrasonic imaging of organs and the circulatory system of humans and lower life forms;
ultrasonic drug delivery, including chemotherapy, to specific organs, including crossing the blood-brain barrier;
treatment of prostate cancer, histotripsy (mechanical tissue fractionation using high frequency ultrasound) and sonothrombolysis (removal of blood clots using sound waves);
ultrasonic delivery of macromolecules including DNA, RNA and proteins to specific tissues, including enhancement of CRSPR biotechnology.
vascular permeability enhancement;
lithotripsy, the disintegration of kidney and bladder stones; or
the benefits listed above, plus the delivery of antioxidant and anti-inflammatory efficacy due to $H_2$.

Example 29: Sequestration of Molecular Hydrogen ($H_2$) from Water Flowing through a Filter Containing a Glucomannan Gel 15. Introduction There is a need for an inexpensive source of clean energy in poor, third world environments. These environments usually have an abundance of wastewater. Anaerobic fermentation of wastewater generates copious amounts of both $H_2$ and $CO_2$ as well as methane. A method has been devised by which an aqueous glucomannan gel can be used to sequester $H_2$ from flowing waste-water and simultaneously-separate it from carbon dioxide. It is noted the konjac plant that contains glucomannan is often farmed in some third-world countries. In such places, it would be cost effective to use glucomannan for sequestering $H_2$ from wastewater.

16. Results

Figure 5A:
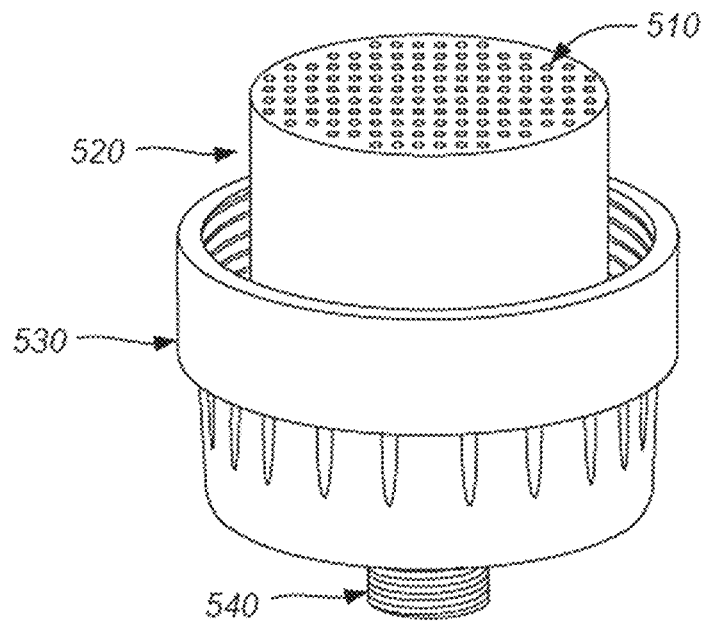
FIG. 5A shows an exemplary housing, comprising a glucomannan gel, comprising preformed pores to allow for increased surface area of contact with a solution.

The drawing in FIG. 5A depicts a preformed aqueous 3-10% glucomannan gel (520) placed in a filter casing (530) that allows 20-50% expansion of the gel in the casing. The gel is preformed around 20-100 plastic or metal rods, 2-4-cm in diameter, so that pores (510) extend from one end of the gel to the other after the gel forms and the rods are withdrawn. Filter casings can be 'off the shelf' products. Gels can be sized according to the needs for sequestering of $H_2$.

Figure 5B:
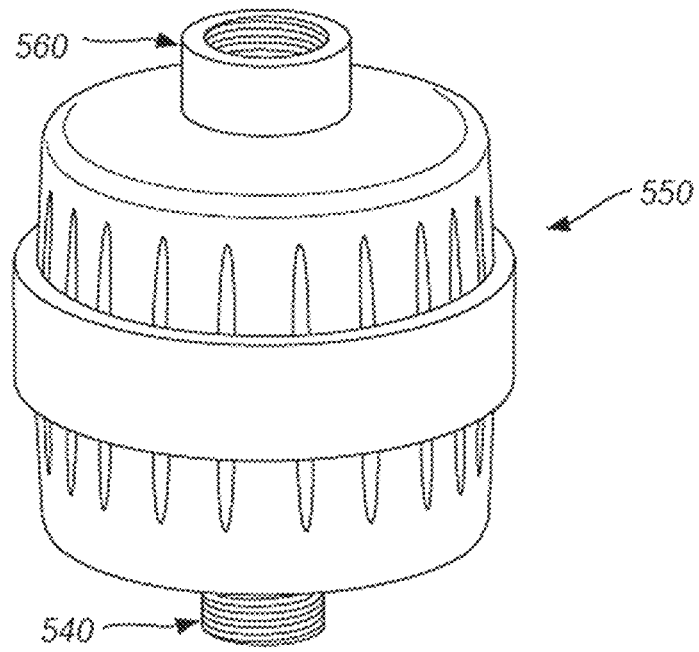
FIG. 5B shows an exemplary housing for a glucomannan gel, with inlet and outlet ports to allow flow of liquid through the housing and in contact with the glucomannan gel.
Figure 6:
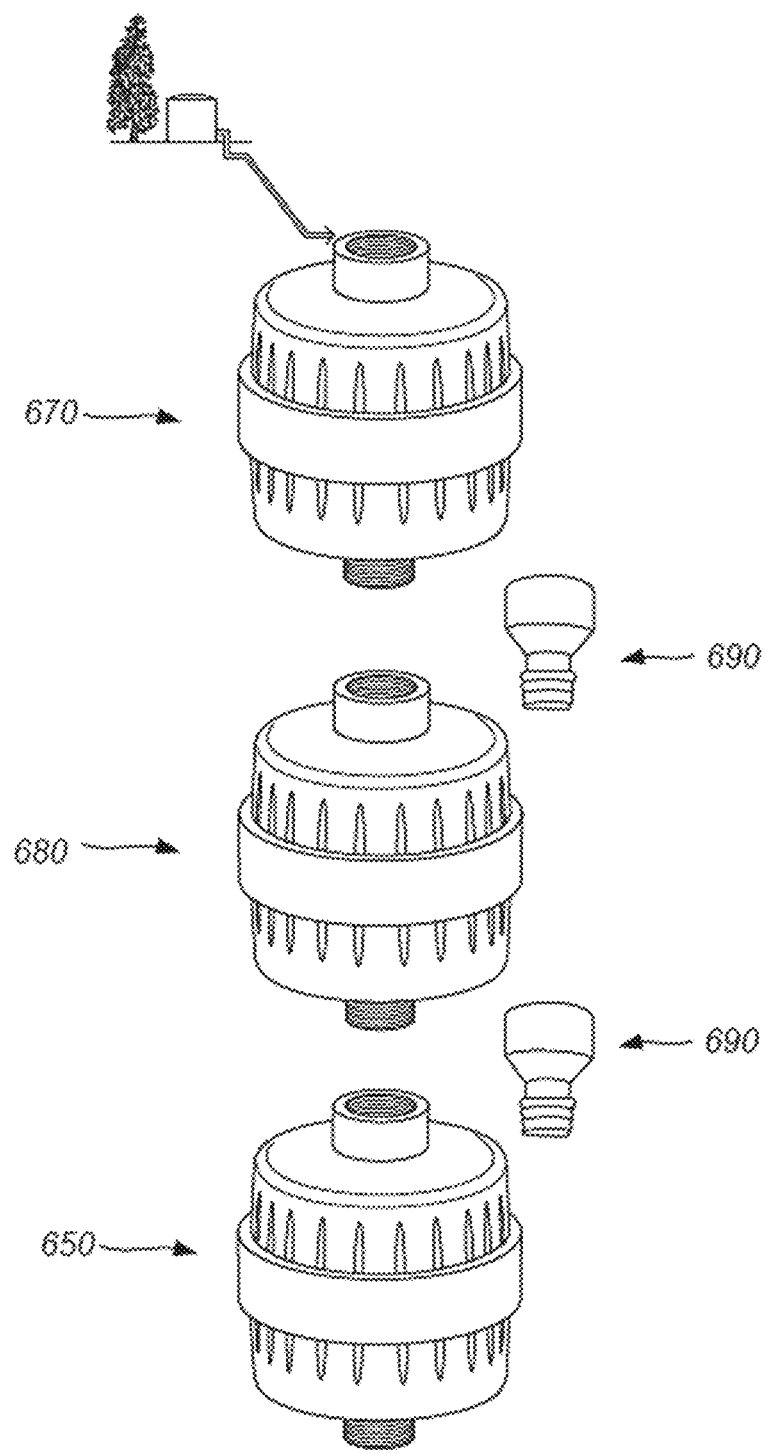
FIG. 6 shows an exemplary system comprising a device as described in FIGS. 5A and 5B and a series of pre-filters to remove particles or other compounds.

FIG. 5B depicts the filter casing (550) comprising the aqueous glucomannan gel for sequestering $H_2$ from a stream of water flowing into the canister through an intake port (560). Water is exposed to the glucomannan gel and within the canister and flows out through the output port (540). The diagram in FIG. 6 is descriptive: 1) waste water is pressurized into the system by gravity or a pump; 2) large particles and/or sludge is removed from the water stream by Prefilter #1 (670) which can comprise inexpensive and reversibly cleaned sand; 3) small particles, metals and organic compounds are removed from the stream by Prefilter #2 (680) which can comprise zeolites as well as other such sequestering materials; and 4) water flows into Filter #3 (650), comprising the aqueous glucomannan gel, water flows into the gel through the pores and around the gel until the gel expands due to its sequestration of $H_2$, hereafter, the water flows through the gel, $H_2$ is removed, sequestered and stored in the expanded aqueous glucomannan gel; 5) the $H_2$-glucomannan gel can be degassed by heating, or otherwise to produce $H_2$ gas for energy or health use; and 6) the aqueous glucomannan gel can be recycled to the filter casing, to collect additional cycles of $H_2$. Filters are connected in series, by non-limiting example, with connectors (690).

17. Discussion

As shown in Example 6 (above), aqueous glucomannan gels sequester $H_2$ but not carbon dioxide. Therefore, the $H_2$ sequestered by the aqueous glucomannan gel will not be 'poisoned' by carbon dioxide. That is, carbon dioxide will not be present to extinguish the flammability of the sequestered $H_2$. On the other hand, if the aqueous glucomannan gel sequesters some methane, it will not present a problem since methane, like $H_2$, can be burned for energy.

Example 30: Effect of Varying Magnesium Metal Powder on the Physical-Chemical Properties of a Weight Loss Product 18. Introduction Volume and viscosity are two properties of a gel formulation that can impart a feeling of fullness when residing in the stomach. Increases in both volume and viscosity will enhance the experience of satiety.

A study was carried out to determine the effect of increasing the concentration of magnesium metal powder (Mg*) on the viscosity, volume, molecular hydrogen content and related physical-chemical properties of a lemon-flavored weight loss formulation.

19. Experimental

Table 17 contains a list of ingredients in the formulations. As shown, the Mg* concentration was varied from 0, 0.12, 0.24 to 0.48 g in the respective formulations. Gels were prepared by adding 4.0 grams of each formulation to 400 mL of distilled water and mixing with a utensil for 120 seconds. The resultant gels were allowed to stand at 70 deg. F for 1-hour.

TABLE 17

Effect of Varying Magnesium Metal Powder on the Physical - Chemical Properties of a Weight Loss Product

| Grams | Formula Ingredients/400 mL Distilled Water Ingredient | Purpose |
|---|---|---|
| 8.00 | Erythritol | Sweetener/Filler |
| 7.00 | L-citric acid - anhydrous | Lemon Flavor |
| 5.20 | Konjac glucomannan | Viscosity Builder |
| 2.00 | Xanthan gum | Thickener |
| 1.20 | sodium ascorbate | antioxidant/preserve |
| 0.92 | Magnesium sulfate | Anti-caking |
| 0.72 | sucralose | sweetener |
| Variable | 230 Mesh Magnesium metal powder (MMP) | Generate $H_2$ |
| 0.16 | Vitamin E Powder | antioxidant/preserve |
| 0.02 | Riboflavin | Color |

| MMP | Dens. (g/mL) | Vol (mL) | Viscosity | $H_2$ | pH |
|---|---|---|---|---|---|
| 0 | 1.050 | 405 | 17,400 | 0 | 2.62 |
| 0.12 | 0.859 | 495 | 34,200 | 629 | 2.93 |
| 0.24 | 0.810 | 525 | 90,500 | 715 | 3.00 |
| 0.48 | 0.709 | 600 | 78,500 | 585 | 3.14 |

Abbreviations
MMP Magnesium metal powder passing through a 230 Mesh sieve.
Dens. Density
g grams
mL milliliters
Vol. Volume
$H_2$ molecular hydrogen measured with the Trustlex Meter.

Volumes were determined by the height of gel attained in the 600 mL beaker. Viscosities were measured with an NDJ-1 rotary type viscometer. For the control gel, not containing Mg*, which had the lowest viscosity, Rotor #3 at a rotation rate of 6 rpm was used. For the three formulations containing Mg*, Rotor #4 and at a rotation rate of 12 rpm was used. The dissolved molecular hydrogen persisting in the gels, after standing for 1-hour, was measured with the Trustlex® $H_2$ Meter. pH was measured with a calibrated ExStick II pH meter. Gel density was calculated by dividing the total weight of each gel by its volume—as listed in Column 14.

20. Results and Discussion

Increasing the concentration of Mg* in the weight loss formulation, depicted in Column 1 of Table 17, results in a concomitant increase in gel volume (see Column 3 of Table 17). This increase in gel volume is due to the generation of molecular hydrogen ($H_2$). This increase in volume results in a decrease in gel density as shown in Column 2 of Table 17.

Viscosity measurements indicate a more complex picture, where the presence of Mg* markedly increases the viscosity—relative to the Control—without Mg* (Column 4 of Table 17). However, a maximum viscosity is reached at an intermediate concentration, i.e., at a concentration of 0.24 g Mg*. Also, this is the gel that retains the highest concentration of dissolved $H_2$. In contrast, the pH of the gels increases as the concentration of Mg* in the gels increases—due to the formation of magnesium hydroxide due to the reaction of Mg* with water.

The results are best explained by: As $H_2$ is generated in the gels containing Mg*, the gels retain $H_2$ bubbles by a strong interaction with glucomannan in the gels. As the density is decreased to 0.810 g/mL, there is a parallel increase in viscosity due to the interaction of $H_2$ bubbles with the gel matrix. This effect is conducive to retaining dissolved $H_2$, as well. As the volume increases beyond 525 mL, the gel becomes more porous, allowing a greater escape of dissolved $H_2$ as well as a relative decrease in gel viscosity.

In summary, the optimal gel for affecting satiety—is the gel containing 0.24 g of Mg*/400 mL distilled water. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A powder composition comprising glucomannan, and a base metal powder, wherein the base metal powder comprises magnesium metal powder.

2. The powder composition of claim 1, wherein, upon mixing the powder composition with a composition comprising an aqueous solvent having an acidic pH, the resulting composition forms a hydrogel or a flowable liquid or a cream or a lotion.

3. The powder composition of claim 1, wherein the glucomannan comprises from about 0.01% to about 99.00% w/w of the powder composition.

4. The powder composition of claim 2, wherein the resulting composition comprises gaseous $H_2$ and dissolved $H_2$.

5. The powder composition of claim 1, wherein the base metal powder comprises: one or more additional base metals selected from the group consisting of lithium, potassium, strontium, calcium, sodium, aluminum, zinc, chromium, manganese, and iron.

6. The powder composition of claim 1, further comprising an organic acid.

7. The powder composition of claim 1, further comprising an organic acid, wherein the resulting composition has an acidic pH.

8. The composition of claim 7 wherein the organic acid is selected from the list consisting of citric acid, malic acid, lactic acid, acetic acid, tartaric acid, succinic acid, phosphoric acid, formic acid, oxalic acid, uric acid, ascorbic acid and any combination thereof.

9. The powder composition of claim 1, wherein the composition further comprising one or more excipients selected from the list consisting of sweeteners, antioxidants, anticaking agents, flavoring agents, coloring agents, and any combination thereof.

10. The powder composition of claim 1, wherein the powder composition is enclosed in a capsule to form an encapsulated composition.

11. The encapsulated composition of claim 10, wherein the encapsulated composition is enclosed in the capsule that is 000 in size.

12. The encapsulated composition of claim 10, wherein the encapsulated composition is enclosed in the capsule comprising cellulose.

13. The composition of claim 1, wherein the composition is contained in a single dose for addition to a composition comprising an aqueous composition to generate a molecular hydrogen containing cream or lotion.

14. The composition of claim 13, wherein the aqueous composition comprises at least 100 ppb molecular hydrogen at standard temperature and pressure.

15. The composition of claim 1, wherein the composition comprises vitamins or minerals, alone or in combination.

16. The composition of claim 15, wherein the vitamins or minerals alone or in combination are in an amount of about 5% to about 15% of RDI (required Daily Intake) for a healthy adult human.

17. The composition of claim 16, wherein the vitamins or minerals, alone or in combination are in an amount of about 5% to about 100% of the RDI.

18. The composition of claim 2, wherein the composition provides a moisturizing effect to the skin of a subject.

* * * * *